United States Patent
Carmi et al.

(10) Patent No.: US 12,077,569 B2
(45) Date of Patent: Sep. 3, 2024

(54) MULTI SUBUNIT PROTEIN MODULES, CELLS EXPRESSING SAME AND USES THEREOF

(71) Applicant: Ramot at Tel-Aviv University Ltd., Tel-Aviv (IL)

(72) Inventors: Yaron Carmi, Tel Aviv (IL); Peleg Rider, Tel Aviv (IL); Diana Rasoulouniriana, Tel Aviv (IL); Lior Tal, Tel Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 18/085,632

(22) Filed: Dec. 21, 2022

(65) Prior Publication Data

US 2023/0340070 A1    Oct. 26, 2023

Related U.S. Application Data

(63) Continuation-in-part of application No. PCT/IL2021/050763, filed on Jun. 22, 2021.

(60) Provisional application No. 63/042,080, filed on Jun. 22, 2020.

(51) Int. Cl.
| | |
|---|---|
| C07K 14/735 | (2006.01) |
| A61K 38/00 | (2006.01) |
| A61K 39/00 | (2006.01) |
| A61P 37/04 | (2006.01) |
| C07K 16/32 | (2006.01) |
| C12N 5/0783 | (2010.01) |

(52) U.S. Cl.
CPC ........ C07K 14/70535 (2013.01); A61P 37/04 (2018.01); C12N 5/0636 (2013.01); C07K 2319/03 (2013.01); C07K 2319/30 (2013.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | McConnell et al. |
| 3,850,752 A | 11/1974 | Schuurs et al. |
| 3,853,987 A | 12/1974 | Dreyer et al. |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles et al. |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,816,567 A | 3/1989 | Cabilly et al. |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,464,764 A | 11/1995 | Capecchi et al. |
| 5,487,992 A | 1/1996 | Capecchi et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 6,111,166 A | 8/2000 | Van de Winkel |
| 6,489,458 B2 | 12/2002 | Hackett et al. |
| 8,313,943 B2 | 11/2012 | Campbell |
| 10,144,770 B2 | 12/2018 | Campana et al. |
| 10,577,417 B2 | 3/2020 | Beatty et al. |
| 2012/0149108 A1 | 6/2012 | Tanabe et al. |

(Continued)

FOREIGN PATENT DOCUMENTS

| | | |
|---|---|---|
| EP | 0340793 | 8/1995 |
| JP | H09506073 A | 6/1997 |

(Continued)

OTHER PUBLICATIONS

Li et al. Genes and Immunity (2009) 10, 380-389.*
Patel et al. (2019) Frontiers in Immunology 10: 223, p. 1-17.*
Junker et al. (2020) Frontiers in Immunology 11: 1393, p. 1-13.*
Barb A.W. (2021) J. Biol. Chem. 296: 100057, p. 1-11.*
English Summary Dated Oct. 26, 2023 of Notification of Office Action Dated Sep. 29, 2023 From the State Intellectual Property Office of the People's Republic of China Re. Application No. 202080037294.9. (4 Pages).
Supplementary European Search Report and the European Search Opinion Dated Apr. 5, 2023 From the European Patent Office Re. Application No. 20774261.0. (15 Pages).
Chauhan et al. "Immune Complexes and Late Complement Proteins Trigger Activation of Syk Tyrosine Kinase in Human CD4+ T cells.", Clinical and Experimental Immunology, 167(2): 235-245, Jan. 11, 2012.

(Continued)

*Primary Examiner* — Ilia I Ouspenski
(74) *Attorney, Agent, or Firm* — Wilson Sonsini Goodrich & Rosati

(57) ABSTRACT

Multi subunit protein modules are provided. Accordingly, there is provided a multi subunit protein module comprising at least three cell membrane polypeptides each comprising an amino acid sequence of an Fc receptor common gamma chain (FcRgamma), said amino acid sequence is capable of transmitting an activating signal; wherein at least one but not all of said at least three polypeptides comprises an extracellular binding domain capable of binding a target that is presented on a cell surface of a target cell of an immune cell, such that upon binding of said extracellular binding domain to said target said activating signal is transmitted in an immune cell expressing said multi subunit protein module. Also provided are cells expressing the multi subunit protein modules and uses thereof.

26 Claims, 14 Drawing Sheets
(14 of 14 Drawing Sheet(s) Filed in Color)
Specification includes a Sequence Listing.

(56) References Cited

U.S. PATENT DOCUMENTS

| | | |
|---|---|---|
| 2015/0139943 A1 | 5/2015 | Campana et al. |
| 2016/0355566 A1 | 12/2016 | Li et al. |
| 2017/0151283 A1 | 6/2017 | Powell |
| 2018/0008638 A1 | 1/2018 | Campana et al. |
| 2021/0401893 A1 | 12/2021 | Carmi et al. |

FOREIGN PATENT DOCUMENTS

| | | |
|---|---|---|
| JP | 2017527310 A | 9/2017 |
| JP | 2018507703 A | 3/2018 |
| WO | WO 95/09011 | 4/1995 |
| WO | WO-0139594 A2 | 6/2001 |
| WO | WO 2006/023148 | 3/2006 |
| WO | WO-2007054160 A2 | 5/2007 |
| WO | WO 2014/039523 | 3/2014 |
| WO | WO 2015/121454 | 8/2015 |
| WO | WO 2015/179833 | 11/2015 |
| WO | WO 2016/149109 | 9/2016 |
| WO | WO 2017/161333 | 9/2017 |
| WO | WO 2017/205254 | 11/2017 |
| WO | WO 2018/017649 | 1/2018 |
| WO | WO 2018/027135 | 2/2018 |
| WO | WO 2018/140960 | 8/2018 |
| WO | WO 2018/151817 | 8/2018 |
| WO | WO 2020/188570 | 9/2020 |
| WO | WO 2021/260696 | 12/2021 |

OTHER PUBLICATIONS

Gilham "International Conference on Lymphocyte Engineering Sep. 13-15, 2019 London, United Kingdom", Human Gene Therapy, 30:A2-A22, Dec. 2019.

Wilson et al. "An Fc[gamma] Receptor-Dependent Mechanism Drives Antibody-Mediated Target-Receptor Signaling in Cancer Cells", Cancer Cell, 19(1): 101-113, Jan. 18, 2011.

Notification of Office Action and Search Report Dated Sep. 29, 2023 From the State Intellectual Property Office of the People's Republic of China Re. Application No. 202080037294.9. (7 Pages).

Translation Dated Oct. 30, 2023 of Notification of Office Action Dated Sep. 29, 2023 From the State Intellectual Property Office of the People's Republic of China Re. Application No. 202080037294. 9. (4 Pages).

International Preliminary Report on Patentability Dated Jan. 5, 2023 From the International Bureau of WIPO Re Application No. PCT/IL2021/050763. (10 Pages).

International Preliminary Report on Patentability Dated Sep. 30, 2021 From the International Bureau of WIPO Re. Application No. PCT/IL2020/050327. (8 Pages).

International Search Report and the Written Opinion Dated Jun. 10, 2020 From the International Searching Authority Re. Application No. PCT/IL2020/050327. (13 Pages).

International Search Report and Written Opinion Dated Aug. 23, 2021 From the International Searching Authority Re Application No. PCT/IL2021/050763. (23 pages).

Chauhan "Human CD4+ T-Cells: A Role for Low-Affinity Fc Receptors", Frontiers in Immunology, 7: 1-8, Published Online Jun. 1, 2016.

Chauhan et al. "Induced Expression of Fc[Gamma]RIIIa (CD16a) on CD4+ T Cells Triggers Generation of IFN-Gamma[High] Subset", The Journal of Biological Chemistry, 290(8): 5127-5140, Feb. 20, 2015.

Clémenceau et al. "Antibody-Dependent Cellular Cytotoxicity (ADCC) Is Mediated by Genetically Modified Antigen-Specific Human T Lymphocytes", Blood, 107(12): 4669-4677, Published Online Mar. 2, 2006.

Hamerman et al. "The Expanding Roles of ITAM Adapters FcRγ and DAP12 in Myeloid Cells", Immunological Reviews, 232(1): 42-58, ublished Oct. 23, 2009.

Kudo et al. "T Lymphocytes Expressing a CD16 Signaling Receptor Exert Antibody-Dependent Cancer Cell Killing", Cancer Research, 74(1): 93-103, Published Online Nov. 6, 2013.

Lanier "DAP10- and DAP12-Associated Receptors in Innate Immunity", Immunological Reviews, 227(1):150-160, Published Dec. 19, 2008.

Rasoulouniriana et al. "A Distinct Subset pf FcGammaRI-Expressing Th1 Cells Exert Antibody-Mediated Cytotoxic Activity", The Journal of Clinical Investigation, 129(10): 4151-4164, Published Online Aug. 26, 2019.

Snyder et al. "Expression of a Recombinant High Affinity IgG Fc Receptor by Engineered NK Cells as a Docking Platform for Therapeutic mAbs to Target Cancer Cells", Frontiers in Immunology, 9: 2873-1-2873-11, Dec. 6, 2018.

Urbanska et al. "Overcoming Resistance to Antibody Targeted Therapy in Cancer Using Gene-Modified T Cells", Molecular Therapy, 22(Suppl.1): S297-S298 , #771, May 1, 2014.

Aqaqe, Nasma, et al., An ERG Enhancer-Based Reporter Identifies Leukemia Cells with Elevated Leukemogenic Potential Driven by ERG-USP9X Feed-Forward Regulation. Cancer research 79(15):3862-3876 (2019).

Berman, Jules J, et al., Classifying the precancers: a metadata approach. BMC Medical Informatics and Decision Making 3(1):1-9 (2003).

Blair, G.E., et al., Enhancers and eukaryotic gene expression. Current communications in molecular biology 13(3):149 (1985).

Boerner et al. Production of antigen-specific human monoclonal antibodies from in vitro-primed human splenocytes. J Immunol. 147(1):86-95 (Jul. 1, 1991).

Burns et al., Vesicular Stomatitis Virus G Glycoprotein Pseudotyped Retroviral Vectors: Concentration to Very High Titer and Efficient Gene Transfer into Mammalian and Nonmammalian Cells, Proc. Natl. Acad. Sci. USA 90(17):8033-8037 (1993).

Calame et al. Transcriptional Controlling Elements In The Immunoglobulin And T Cell Receptor Loci. Adv Immunol 43:235-275 (1988).

Chen et al. Fusion protein linkers: Property, design and functionality. Advanced Drug Delivery Reviews 65:1357-1369 (2013).

Chichili et al. Linkers in the structural biology of protein-protein interactions. Protein science : a publication of the Protein Society 22(2):153-167 (2013).

Chugai et al.: Proprietary Innovative Antibody Engineering Technologies in Chugai Pharmaceutical. Chugai Pharmatical's Unique and Innovative Antibody Technology, pp. 1-77 (2012).

Cole S, et al., The EBV-Hybridoma Technique and Its Application to Human Lung Cancer. Monoclonal Antibodies and Cancer Therapy 27:77-96 (1985).

Coussens, Lisa M, et al., Neutralizing tumor-promoting chronic inflammation: a magic bullet?. Science 339(6117):286-91 (2013).

Crasto, C.J. Linker: a program to generate linker sequences for fusion proteins. Protein Engineering, 13(5): 309-312 (2000).

Davila et al. How do CARs work? Early insights from recent clinical studies targeting CD19. Oncoimmunology 1(9):1577-1583 (2012).

D.M. Fishwild et al., High-avidity human IgG kappa monoclonal antibodies from a novel strain of minilocus transgenic mice. Nat Biotechnol. Jul. 1996; 14(7):845-51. doi: 10.1038/nbt0796-845. PMID: 9631008.

Dunn et al. Cancer immunoediting: from immunosurveillance to tumor escape. Nature Immunology 3:991-998 (2002).

Fingl et al. Chapter 1: General Principles. In: The Pharmacological basis of therapeutics (pp. 1-46) (1975).

Freshney et al.: Animal Cell Culture: A Practical Approach. Oxford University Press 53 (1986).

Gabrilovich et al. Myeloid-derived-suppressor cells as regulators of the immune system Nat Rev Immunol 9(3):162-174 (2009).

Gajewski, et al. Innate and adaptive immune cells in the tumor microenvironment. Nature Immunology, vol. 14, No. 10, Oct. 2013, pp. 1014-1022.

Ghosh et al. Design of Liposomes for circumventing the reticuloendothelial cells. Glycobiology 5:505-510 (1991).

Globerson-Levin, A, et al., Elimination of progressive mammary cancer by repeated administrations of chimeric antigen receptor-modified T cells. Molecular Therapy 22(5):1029-38 (2014).

(56) References Cited

OTHER PUBLICATIONS

Gross et al. Generation of effector T cells expressing chimeric T cell receptor with antibody type-specificity. Transplant Proc. 21(1 Pt 1):127-130 (1989).
Gross, Gideon, et al., Therapeutic Potential of T Cell Chimeric Antigen Receptors (CARs) in Cancer Treatment: Counteracting Off-Tumor Toxicities for Safe Car T Cell Therapy. Annual Review of Pharmacology and Toxicology 56(1):59-83 (2016).
Harrison, P.T, et al., The interaction between human Fc gamma RI and the gamma-chain is mediated solely via the 21 amino acid transmembrane domain of Fc gamma RI. Molecular Membrane Biology 12(4):309-12 (1995).
Hodi et al. Improved survival with ipilimumab in patients with metastatic melanoma. N Engl J Med 363(8):711-723 (2010).
Hoogenboom, et al. By-passing immunisation. Human antibodies from synthetic repertoires of germline VH gene segments rearranged in vitro. J Mol Biol. Sep. 20, 1992;227(2):381-8.
Jackson et al. Driving CAR T-cells forward. Nat Rev Clin Oncol 13(6):370-383 (2016).
Jones et al., Replacing The Complementarity-determining Regions In A Human Antibody With Those From A Mouse. Nature 321(6069):522-525 (1986).
Joyce, Johanna A, et al., T cell exclusion, immune privilege, and the tumor microenvironment. Science 348(6230):74-80 (2015).
Kalos, et al., T Cells with Chimeric Antigen Receptors Have Potent Antitumor Effects and Can Establish Memory in Patients with Advanced Leukemia. Science Translation Medicine 3:95ra73 (2011).
Khong, Hung T, et al., Natural Selection of Tumor Variants in the Generation of tumor escape Phenotypes. Nature Immunology 3(11):999-1005 (2002).
Kim, M.K, et al., Fcgamma receptor transmembrane domains: role in cell surface expression, gamma chain interaction, and phagocytosis. Blood 101(11):4479-84 (2003).
Lamers, C H, et al., Protocol for gene transduction and expansion of human T lymphocytes for clinical immunogene therapy of cancer. Cancer Gene Therapy 9(7):613-23 (2002).
Lonberg et al. Human antibodies from transgenic mice. Int Rev Immunol. 13(1):65-93 (1995).
Mantovani, Alberto, et al., Macrophages, innate immunity and cancer: balance, tolerance, and diversity. Current Opinion in Immunology 22(2):231-7 (2010).
Marks et al.: By-passing Immunization: Building High Affinity Human Antibodies by Chain Shuffling. Biotechnology (NY) 10(7):779-783 (1992).
Marks et al., By-Passing Immunization Human Antibodies from V-gene Libraries Displayed on Phage. J. Mol. Biol., 222 (1991): 581-597.
Maus, M V, et al., Antibody-modified T cells: CARs take the front seat for hematologic malignancies. Blood 123(17):2625-35 (2014).
Morrison. Immunology. Success in specification. Nature 368(6474):812-3 (1994).
N. Lonberg et al., Antigen-specific human antibodies from mice comprising four distinct genetic modifications. Nature. Apr. 28, 1994;368(6474):856-9. doi: 10.1038/368856a0. PMID: 8159246.
Neuberger. Generating high-avidity human Mabs in mice. Nat Biotechnol. 14(7):826 (1996).
Nicholson, Emma, et al., Improving TCR Gene Therapy for Treatment of Haematological Malignancies. Advances in Hematology 2012:1-11 (2012).
Nicolas et al. Chapter 25: Retroviral Vectors. In Vectors: A survey of molecular cloning vectors and their uses Rodriguez and Denhardt eds. Stoneham: Butterworth (pp. 494-513) (1988).

Notice of Reason(s) for Rejection Dated Feb. 20, 2024 From the Japan Patent Office Re. Application No. 2021-556491 and Its Translation Into English. (21 Pages).
Okayama et al.: Role of High-Affinity IgE Receptor β Chain in Human Mast Cells. Chemistry and Biology. 53(4):222-227 (2015).
Pardoll. The blockade of immune checkpoints in cancer immunotherapy. Nat Rev Cancer. 12(4):252-264 (2012).
Porter et al. Chimeric antigen receptor-modified T cells in chronic lymphoid leukemia. NEJM 365:725-733 (2011).
Presta: Antibody Engineering. Curr Op Struct Biol 2:593-596 (1992).
Restifo et al., Adoptive immunotherapy for cancer: harnessing the T cell response. Nat Rev Immunol 12:269-281 (2012).
Riechmann et al., Reshaping human antibodies for therapy. Nature 332(6162):323-327 (1988).
Rosenberg, Steven A, et al., Decade in review-cancer immunotherapy: entering the mainstream of cancer treatment. Nature Reviews Clinical Oncology 11(11):630-632 (2014).
Rudensky et al. FOXP3 and NFAT: partners in tolerance. Cell 126(2):253-256 (2006).
Sambrook et al., Molecular Cloning: A Laboratory Manual, 2nd edition, Cold Spring Harbor Laboratory Press (1989): 29 pages.
Sharma et al. The future of immune checkpoint therapy. Science 348:56-61 (2015).
Sioud, Mouldy, et al., Generation of new peptide-Fc fusion proteins that mediate antibody-dependent cellular cytotoxicity against different types of cancer cells. Molecular Therapy Methods & Clinical Development 2(15043):1-10 (2015).
Spitzer et al. Systemic Immunity Is Required for Effective Cancer Immunotherapy. Cell 168:487-502 (2017).
Steinman, RM. The dendritic cell system and its role in immunogenicity. Annu Rev Immunol. 1991;9:271-96.
Tonkinson et al., New Drugs: Antisense Oligodeoxynucleotides as Clinical Therapeutic Agents, Cancer Investigation, (1996) 14:1, 54-65, DOI: 10.3109/07357909609018436.
Ui-Tei et al: Sensitive assay of RNA interference in Drosophila and Chinese hamster cultured cells using firefly luciferase gene as target; FEBS Lett, 479:79-82 (2000).
U.S. Appl. No. 18/085,632 Office Action dated Oct. 13, 2023.
Verhoeyen et al.: Reshaping human antibodies: Grafting an antilysozyme activity. Science 239:1534-1536 (1988).
Wang et al. Manufacture of tumor-and virus-specific T lymphocytes for adoptive cell therapies. Cancer Gene Therapy 22(2):85-94 (2015).
Weidle, U.H. et al. Genetically Engineered Fusion Proteins for Treatment of Cancer. Cancer Genomics & Proteomics 9:357-372 (2012).
Whiteside. The tumor microenvironment and its role in promoting tumor growth. Oncogene 27:5904-5912 (2008).
Winoto et al. A novel, inducible and T cell-specific enhancer located at the 3' end of the T cell receptor alpha locus. EMBO J 8(3):729-733 (1989).
Wu et al., Adoptive T-cell therapy using autologous tumor-infiltrating lymphocytes for metastatic melanoma: current status and future outlook. The Cancer Journal 18(2):160-175 (2012).
Chinese Application No. 202080037294.9 Second Examination Opinion dated Jun. 29, 2024.
Krishnan et al.: The FcRγ Subunit and Syk Kinase Replace the CD3ζ-Chain and ZAP-70 Kinase in the TCR Signaling Complex of Human Effector CD4 T Cells1. Journal Of Immunolgy, 170(8):4189-4195 (2003).

* cited by examiner

| Receptor | FcγRI EC | FcγRI TM | FcR-γ intracellular | Signaling A | 2A peptide | FcR-γ | Signaling B |
|---|---|---|---|---|---|---|---|
|  | OX40 | 41BB | TNFR2 | IL-12R |  | IL-23 | IFNgR | IL-2R | IL-1R |
| Signaling A | OX40 | 41BB | TNFR2 | IL-12Rb1 |  | IL-12Rb1 | IFNgR1 | IL-2Rb | IL-2R2 |
| Signaling B | OX40 | 41BB | TNFR2 | IL-12Rb2 |  | IL-23R | IFNgR2 | IL-2RγC | IL-1RacP |

Alpha-gamma-SignalA-2A-Gamma-SignalB

MULTI SUBUNIT PROTEIN MODULES, CELLS EXPRESSING SAME AND USES THEREOF

RELATED APPLICATIONS

This application is a Continuation-in-Part (CIP) of PCT Patent Application No. PCT/IL2021/050763 having International filing date of Jun. 22, 2021, which claims the benefit of priority of U.S. Provisional Patent Application No. 63/042,080 filed on Jun. 22, 2020. The contents of the above applications are all incorporated by reference as if fully set forth herein in their entirety.

SEQUENCE LISTING STATEMENT

The XML file, entitled 94673ReplacementSequence-Listing.xml, created on Apr. 26, 2023, comprising 110,982 bytes, submitted concurrently with the filing of this application is incorporated herein by reference.

FIELD AND BACKGROUND OF THE INVENTION

The present invention, in some embodiments thereof, relates to multi subunit protein modules, cells expressing same and uses thereof.

Cancer immunotherapy, including cell-based therapy, antibody therapy and cytokine therapy, has emerged in the last couple of years as a promising strategy for treating various types of cancer owing to its potential to evade genetic and cellular mechanisms of drug resistance and to target tumor cells while sparing healthy tissues.

Antibody-based cancer immunotherapies, such as monoclonal antibodies, antibody-fusion proteins, and antibody drug conjugates (ADCs) depend on recognition of cell surface molecules that are differentially expressed on cancer cells relative to non-cancerous cells and/or immune-checkpoint blockade. Binding of an antibody-based immunotherapy to a cancer cell can lead to cancer cell death via various mechanisms, e.g., antibody-dependent cell-mediated cytotoxicity (ADCC), complement-dependent cytotoxicity (CDC), direct cytotoxic activity of the payload from an antibody-drug conjugate (ADC) or suppressive checkpoint blockade. Many of these mechanisms initiate through the binding of the Fc domain of cell-bound antibodies to specialized cell surface receptors (Fc receptors) on hematopoietic cells.

Cell-based therapy using e.g. T cells having a T cell receptor (TCR) specific for an antigen differentially expressed in association with an MHC class I molecule on cancer cells relative to non-cancerous cells were shown to exert anti-tumor effects in several types of cancers, e.g. hematologic malignancies. However, antigen-specific effector lymphocytes, are very rare, individual-specific, limited in their recognition spectrum and difficult to obtain against most malignancies.

Strategies combining principles of antibody-based cancer immunotherapy and cell based therapy, such as CAR T cells and combined treatment with antibodies and T cells expressing Fc receptors have been disclosed (see e.g. EP Patent No: EP0340793; International Patent Application Publication No: WO2017205254 and WO2015179833; US Patent Application Publication Nos: US20150139943, US20180008638 and US20160355566; Clemenceau et al. Blood. 2006; 107:4669-4677; and Urbanska et al. Molecular Therapy. 2014; 22(Supplement 1): S297-S298). However, attempts made to date to harness these cells against solid tumors were disappointing. Thus, an urgent need to develop treatments capable of eradicating solid tumors, which feature a higher safety profile and do not depend exclusively on the host T-cell repertoire, still remains.

Additional background art includes Rasoulouniriana et al. J Clin Invest. (2019) 129(10): 4151-4164; U.S. Pat. Nos. 8,313,943 and 6,111,166; and International Patent Application Publication No: WO2015121454.

SUMMARY OF THE INVENTION

According to an aspect of some embodiments of the present invention there is provided a multi subunit protein module comprising at least three cell membrane polypeptides each comprising an amino acid sequence of an Fc receptor common γ chain (FcRγ), the amino acid sequence is capable of transmitting an activating signal; wherein at least one but not all of the at least three polypeptides comprises an extracellular binding domain capable of binding a target that is presented on a cell surface of a target cell of an immune cell, such that upon binding of the extracellular binding domain to the target the activating signal is transmitted in an immune cell expressing the multi subunit protein module.

According to some embodiments of the invention, the binding domain is of a receptor and the target is a ligand of the receptor.

According to some embodiments of the invention, the binding domain is of an Fcγ receptor and the target is an Fc ligand.

According to some embodiments of the invention, the binding domain is of a ligand and the target is a receptor of the ligand.

According to some embodiments of the invention, the multi subunit protein module is devoid of an antibody binding domain.

According to some embodiments of the invention, the multi subunit protein module is devoid of an scFv.

According to some embodiments of the invention, the binding domain is of an antibody and the target is an antigen.

According to some embodiments of the invention, the binding domain comprises a scFv.

According to some embodiments of the invention, the at least one polypeptide comprising the binding domain comprises an amino acid sequence capable of recruiting polypeptides of the at least three polypeptides comprising the amino acid sequence of FcRγ comprised in the multi subunit protein module upon binding of the binding domain to the target.

According to some embodiments of the invention, the amino acid sequence capable of recruiting the other polypeptides comprises the transmembrane domain of an Fc receptor.

According to some embodiments of the invention, the Fc receptor is Fcγ receptor.

According to some embodiments of the invention, the Fcγ receptor is CD64.

According to some embodiments of the invention, at least two of the at least three cell membrane polypeptides comprise a dimerizing moiety.

According to some embodiments of the invention, the polypeptides comprising the amino acid sequence of FcRγ and not comprising the binding domain comprise a dimerizing moiety.

According to an aspect of some embodiments of the present invention there is provided a dimerizing moiety comprises an amino acid sequence of a transmembrane domain of the FcRγ.

According to some embodiments of the invention, the binding domain is of CD64 and the target is an Fc ligand; the at least one polypeptide comprising the binding domain comprises a transmembrane domain of CD64; and the polypeptides comprising the amino acid sequence of FcRγ and not comprising the binding domain comprise as a dimerizing moiety an amino acid sequence of a transmembrane domain of the FcRγ.

According to some embodiments of the invention, the target cell of the immune cell is a pathologic cell.

According to an aspect of some embodiments of the present invention there is provided at least one polynucleotide encoding the multi subunit protein module.

According to some embodiments of the invention, the at least one polynucleotide comprises a nucleic acid sequence encoding a first polypeptide comprising an extracellular and a transmembrane domain of CD64 and an intracellular domain of FcRγ; and a nucleic acid sequence encoding a second polypeptide comprising an extracellular, a transmembrane and an intracellular domain of FcRγ.

According to some embodiments of the invention, the multi subunit protein module is encoded by a single polynucleotide.

According to some embodiments of the invention, the polynucleotide comprises a nucleic acid sequence encoding a 2A skipping peptide between the nucleic acid sequence encoding the first polypeptide and the nucleic acid sequence encoding the second polypeptide.

According to an aspect of some embodiments of the present invention there is provided an immune cell genetically engineered to express the at least one polynucleotide.

According to an aspect of some embodiments of the present invention there is provided an immune cell expressing the at least one polynucleotide.

According to an aspect of some embodiments of the present invention there is provided an immune cell expressing the multi subunit protein module.

According to an aspect of some embodiments of the present invention there is provided a method of expressing a multi subunit protein module in an immune cell, the method comprising introducing into an immune cell the at least one polynucleotide, under conditions which allow expression of the multi subunit protein module.

According to some embodiments of the invention, the introducing is effected in-vitro or ex-vivo.

According to some embodiments of the invention, the immune cell is a T cell.

According to some embodiments of the invention, the immune cell is a NK cell.

According to an aspect of some embodiments of the present invention there is provided a T cell expressing a polypeptide complex, wherein the polypeptide complex comprises at least a first polypeptide and a second polypeptide, wherein the first and second polypeptides are not translationally fused, wherein the first polypeptide comprises an amino acid sequence of an Fc receptor common γ chain (FcRγ), the amino acid sequence is capable of transmitting an activating signal and forming a homodimer; and the second polypeptide comprising:
  (i) an extracellular ligand-binding domain of an Fcγ receptor capable of binding an Fc ligand,
  (ii) an amino acid FcRγ capable of transmitting an activating signal and
  (iii) an amino acid sequence capable of recruiting the first polypeptide,
such that upon binding of the Fc ligand to the extracellular ligand-binding domain of the Fcγ receptor the activating signal is transmitted.

According to an aspect of some embodiments of the present invention there is provided a method of treating a disease associated with a pathologic cell in a subject in need thereof, the method comprising administering to the subject a therapeutically effective amount of the immune cell, wherein the pathologic cell presents the target on its cell surface, thereby treating the disease in the subject.

According to an aspect of some embodiments of the present invention there is provided the immune cell, for use in treating a disease associated with a pathologic cell in a subject in need thereof, wherein the pathologic cell presents the target on its cell surface.

According to some embodiments of the invention, the subject is treated with a therapeutic composition comprising the target, the therapeutic composition being specific for the pathologic cell.

According to some embodiments of the invention, the method comprises administering to the subject a therapeutically effective amount of a therapeutic composition comprising the target, the therapeutic composition being specific for the pathologic cell.

According to an aspect of some embodiments of the present invention there is provided the immune cell and a therapeutic composition comprising the target, for use in treating a disease associated with a pathologic cell in a subject in need thereof, wherein the therapeutic composition being specific for the pathologic cell.

According to an aspect of some embodiments of the present invention there is provided an article of manufacture comprising a packaging material packaging the immune cells and a therapeutic composition comprising the target.

According to some embodiments of the invention, the therapeutic composition is specific for a pathologic cell.

According to some embodiments of the invention, wherein when the target is an Fc ligand, the therapeutic composition is an Fc-fusion protein.

According to some embodiments of the invention, wherein when the target is an Fc ligand, the therapeutic composition is an antibody.

According to some embodiments of the invention, the immune cell is a T cell; the binding domain is of CD64 and the target is an Fc ligand; and the therapeutic composition is an antibody specific for the pathologic cell.

According to an aspect of some embodiments of the present invention there is provided a method of increasing the killing capacity of an antibody against a pathologic cell in a subject in need thereof, the method comprising administering to the subject a therapeutically effective amount of:
  (i) an antibody specific for the pathologic cell; and
  (ii) the immune cell, wherein the immune cell is a T cell; wherein the binding domain is of CD64 and the target is an Fc ligand,
  thereby increasing the killing capacity of the antibody against the pathologic cell.

According to some embodiments of the invention, the antibody is an IgG.

According to some embodiments of the invention, the pathologic cell is a cancerous cell and wherein the disease is cancer.

According to some embodiments of the invention, the cancer is selected from the group consisting of melanoma, lymphoma, colon cancer, lung cancer, breast cancer and pancreatic cancer.

According to some embodiments of the invention, the cancer is melanoma or lymphoma.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
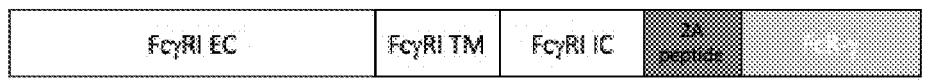
Figure 1A:
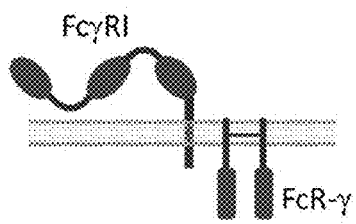
Figure 1B:
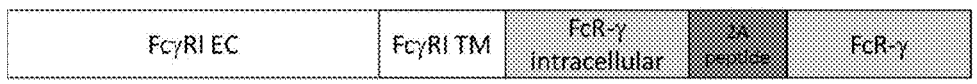
Figure 1B:
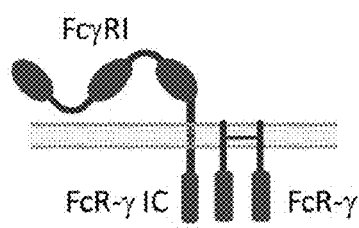

FIGS. 1A-B show schematic representations of the constructs used and illustrations of the receptors as expressed proteins. FIG. 1A demonstrates a construct encoding the extracellular, transmembrane and intracellular domains of FcγRI, T2A skipping peptide and FcRγ (SEQ ID NOs: 1-2), denoted herein as Alpha-2A-gamma. FIG. 1B demonstrates a construct encoding the extracellular and transmembrane domains of FcγRI fused to the intracellular domain of FcRγ, T2A skipping peptide and FcRγ (SEQ ID NOs: 3-4), denoted herein as Alpha-gamma 2A-gamma.

Figure 2A:
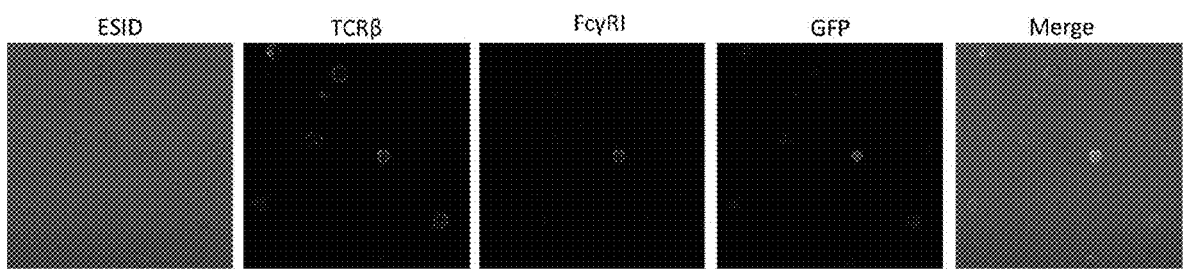
Figure 2B:
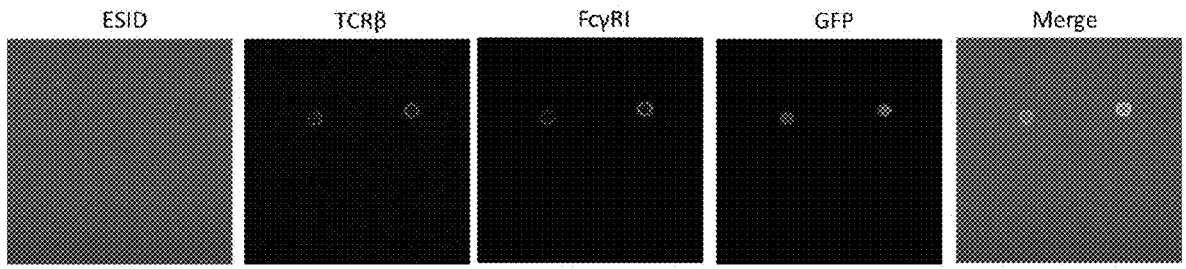

FIG. 2A-B show confocal microscopy of cells expressing the Alpha-2A-Gamma (FIG. 2A) or Alpha-gamma-2a-Gamma (FIG. 2B) construct and stained for TCRβ, FcγRI and GFP. ×200 magnitude.

Figure 3:
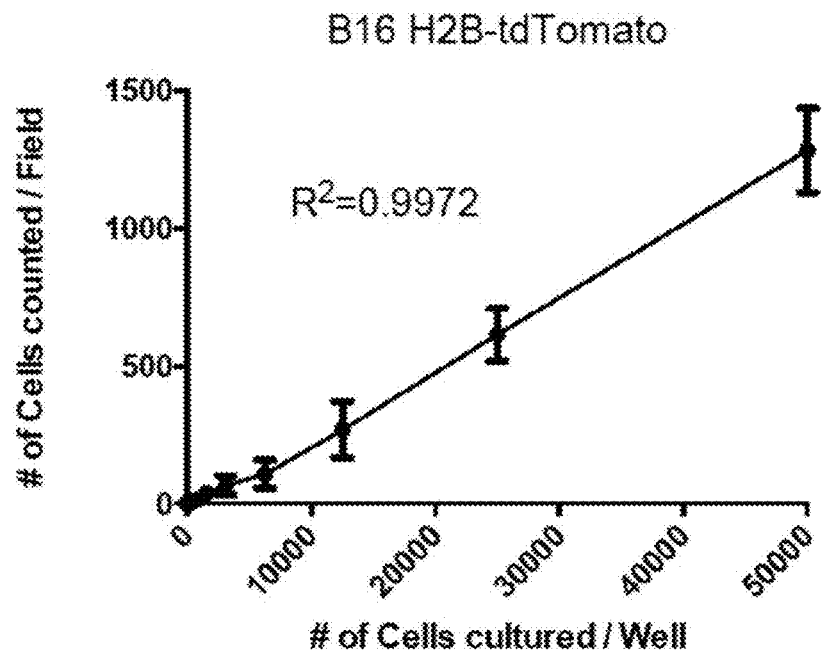

FIG. 3 is a graph demonstrating the correlation between the number of cells counted by incuCyte imager in a field and the number of B16-H2B-tdTomato cells cultured in a well of 96 wells plate.

Figure 4A:
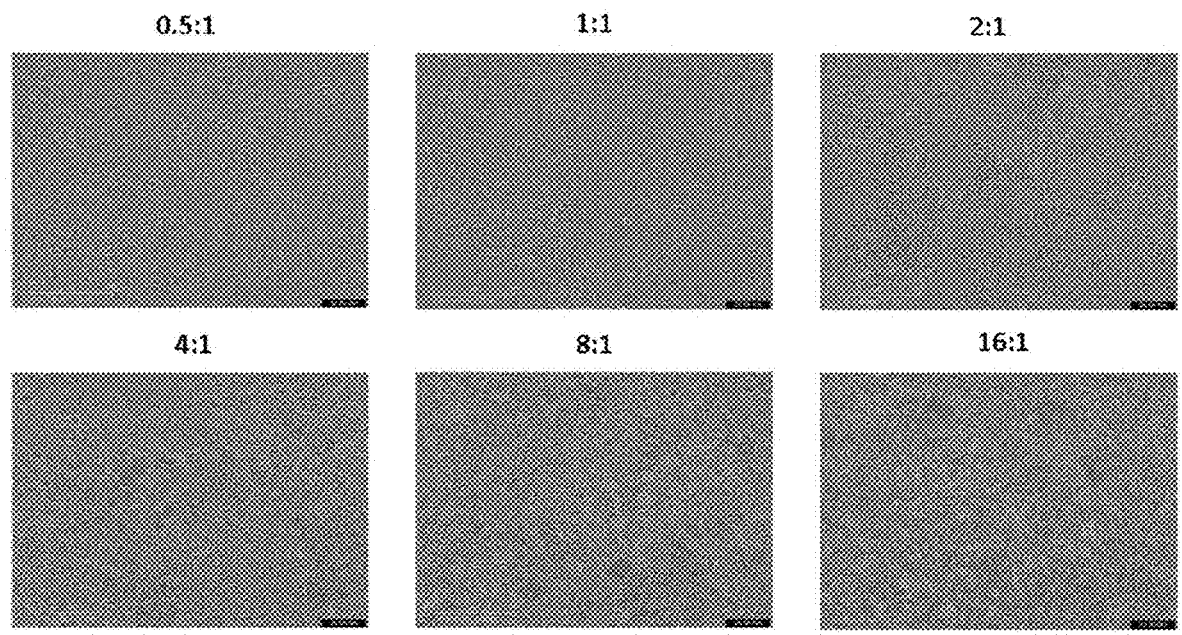
Figure 4B:
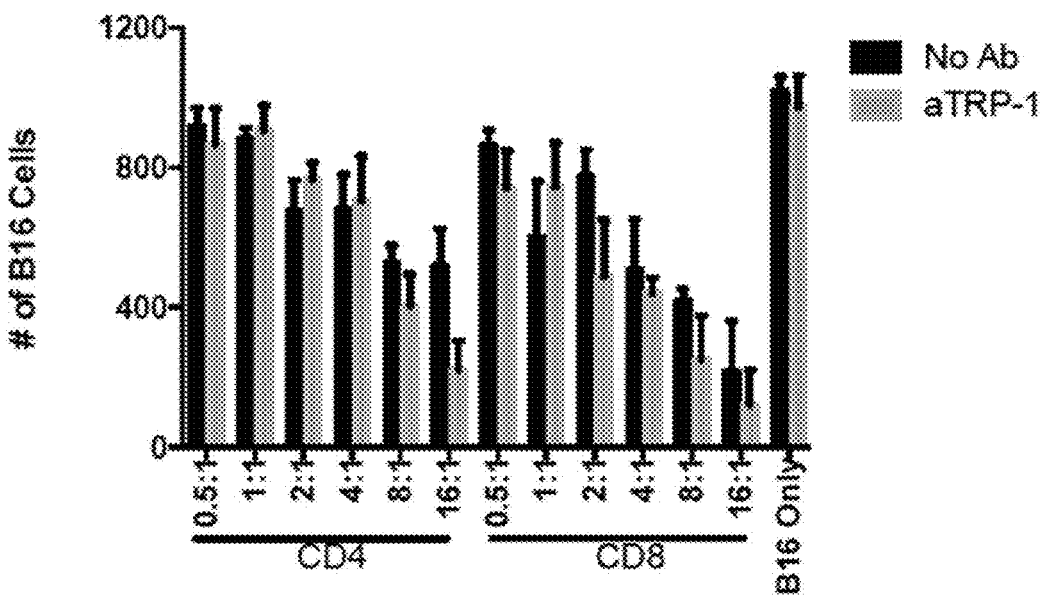

FIGS. 4A-B demonstrate killing of B16 target cells by Alpha-2A-Gamma infected cells in different ratios. FIG. 4A shows representative images taken by incuCyte imager following 2 days of co-culturing CD8+ T cells infected with Alpha-2A-Gamma and B16-H2B-tdTomato at the indicated effector:target ratios ranging from 0.5:1 to 16:1, in the presence of an anti-TRP-1 antibody. ×100 magnitude. FIG. 4B is a graph demonstrating the number of target cells counted by the incuCyte imager, following 2 days of co-culturing CD4+ or CD8+ T cells infected with Alpha-2A-Gamma and B16-H2B-tdTomato in different effector:target ratios with or without an anti-TRP-1 antibody.

Figure 5A:
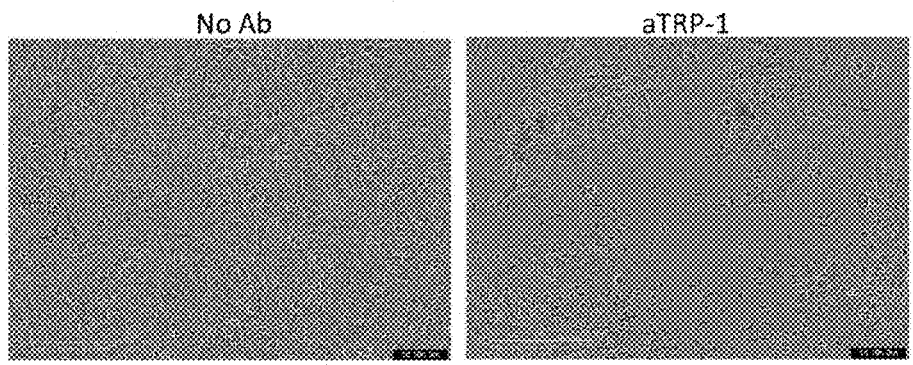
Figure 5B:
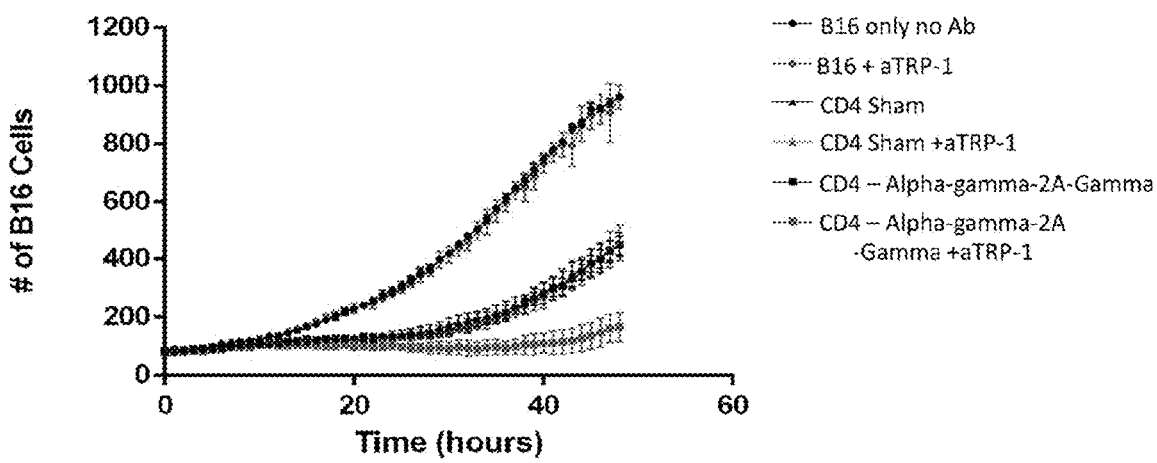
Figure 5C:
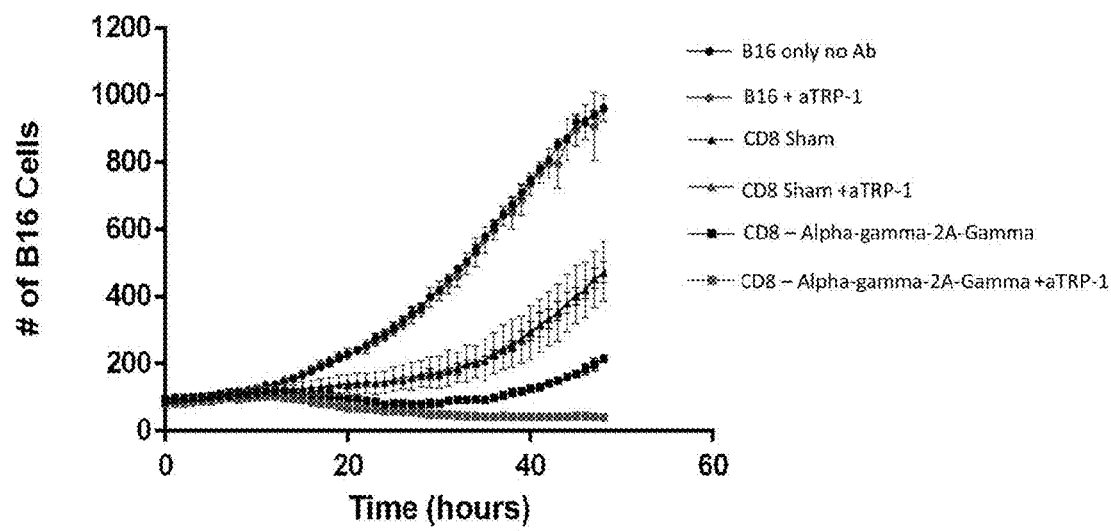

FIGS. 5A, 5B and 5C demonstrate killing of B16 target cells by Alpha-gamma-2a-Gamma infected cells. FIG. 5A shows representative images taken by incuCyte imager following 2 days of co-culturing CD8+ T cells infected with Alpha-Gamma-2A-Gamma and B16-H2B-tdTomato at an effector:target ratio 2:1, in the presence or absence of an anti-TRP-1 antibody. ×100 magnitude. FIGS. 5B-C show graphs demonstrating the number of target cells counted by the incuCyte imager, following 2 days of co-culturing CD4+ (FIG. 5B) or CD8+ (FIG. 5C) T cells infected with Alpha-gamma-2A-Gamma at an effector:target ratio 2:1, in the presence or absence of an anti-TRP-1 antibody. Shown are also the following controls: B16 H2B-tdTomato target cells cultured alone, cultured with anti-TRP-1 antibody, co-cultured with non-infected CD4+ or CD8+ T cells (Sham), co-cultured with non-infected CD4+ or CD8+ T cells (Sham) and anti-TRP-1 antibody.

Figure 6A:
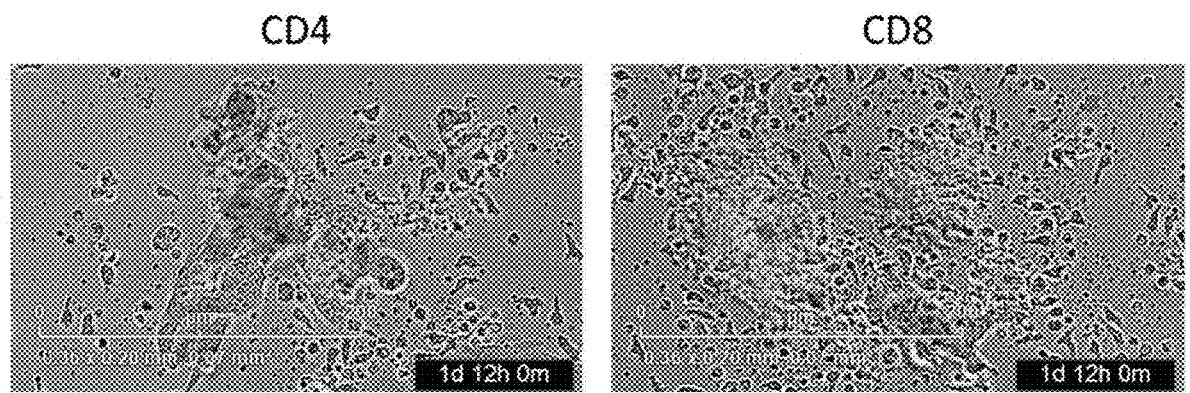
Figure 6B:
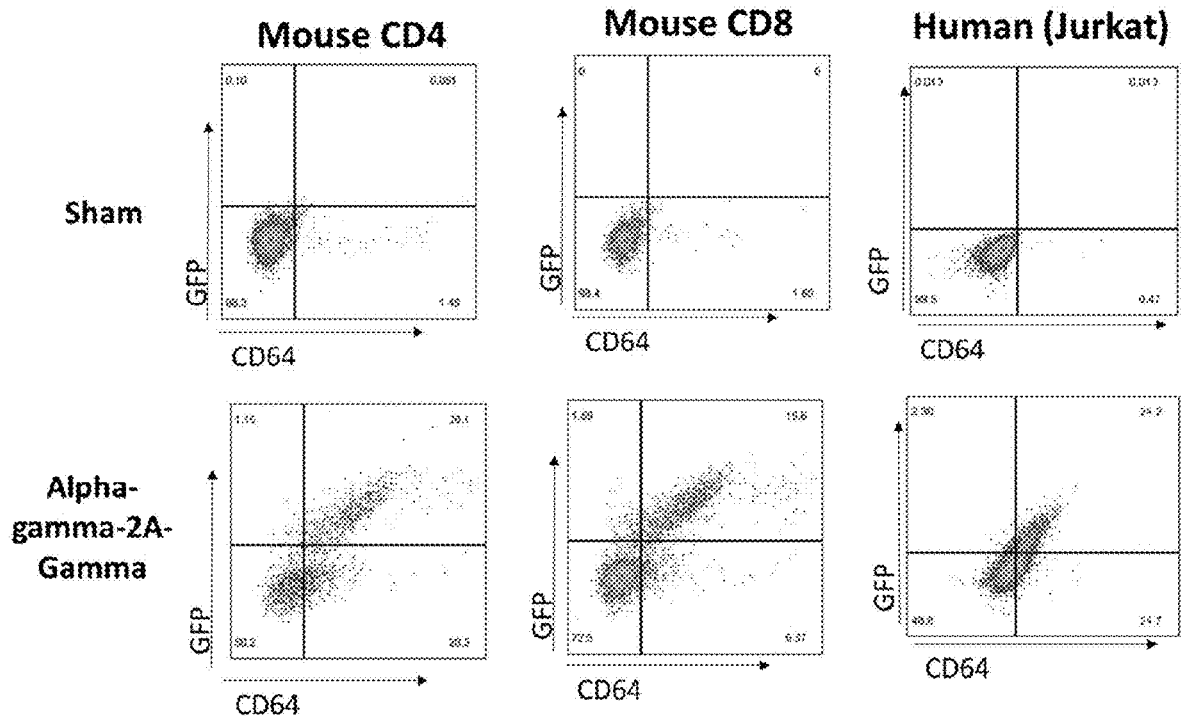

FIG. 6A-B show GFP and FcγRI (CD64) expression in infected effector T cells. FIG. 6A shows images taken following co-culturing B16-H2B-tdTomato with CD4+ or CD8+ T cells infected with Alpha-gamma-2A-Gamma and an anti-TRP-1 antibody, with bright light, red and green filters in incuCyte imager. ×200 magnitude. FIG. 6B shows flow cytometry analysis of non-infected (sham) or Alpha-gamma-2A-Gamma infected mouse CD4+ T cells, mouse CD8+ T cells or human Jurkat T cells. Cells were analyzed for FcγRI (CD64) staining and GFP expression.

Figure 7:
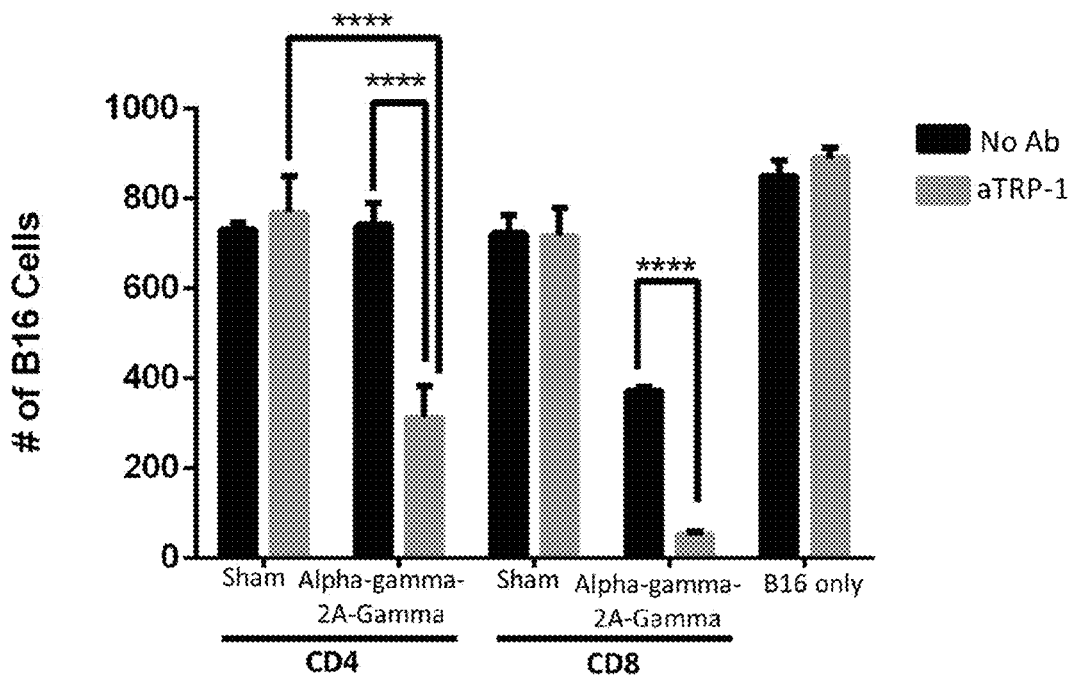

FIG. 7 demonstrates killing of B16 target cells by Alpha-gamma-2a-Gamma infected cells. Shown are the number of B16-H2B-tdTomato target cells counted by the incuCyte imager, following 60 hours of co-culturing with CD4+ or CD8+ T cells infected with Alpha-gamma-2A-Gamma in the presence or absence of an anti-TRP-1 antibody, as compared to non-infected cells (sham). Also shown is a control of B16 H2B-tdTomato target cells cultured alone.

Figure 8A:
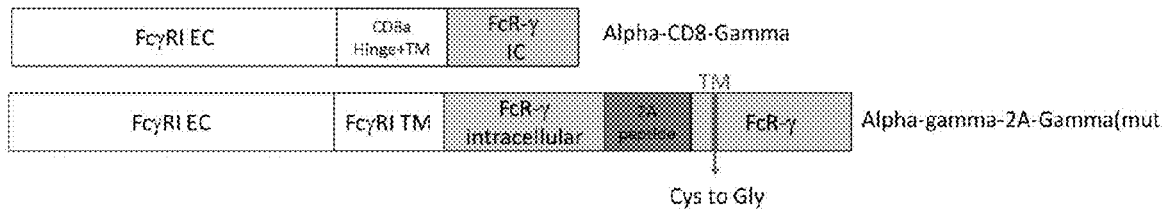
Figure 8B:
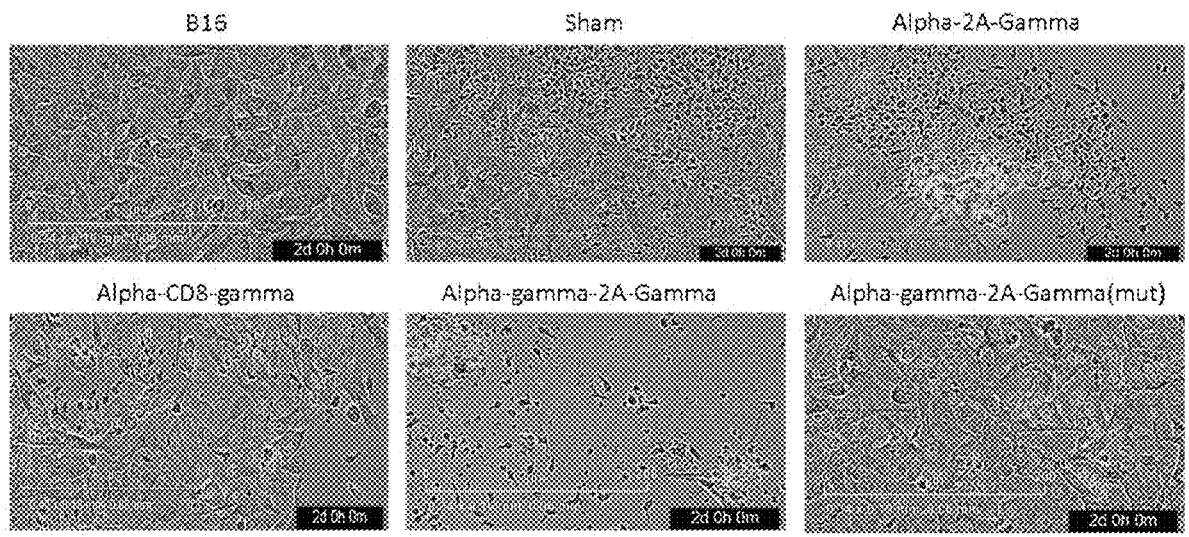
Figure 8C:
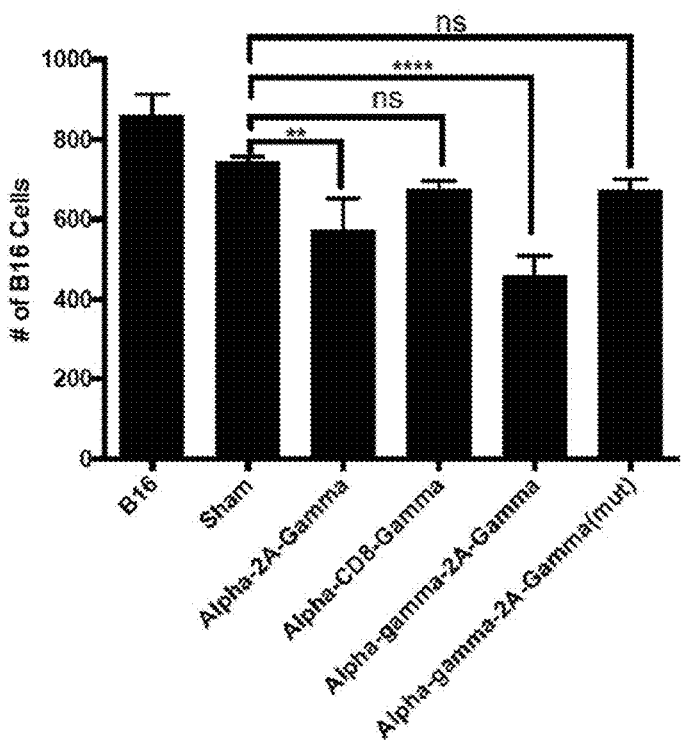

FIGS. 8A, 8B and 8C demonstrate the necessity of FcγRI receptor to signal through the dimer of the co-receptor FcRγ chain. FIG. 8A shows schematic representations of a construct composed of FcRI alpha chain extracellular D1-D3 domains fused to the hinge and transmembrane domains of CD8a together with signaling intracellular gamma (SEQ ID NOs: 5-6), denoted herein as Alpha-CD8-gamma; and a construct composed of the same sequence of Alpha-gamma-2A-Gamma construct, but with two cysteine residues in the transmembrane domain (Cysteine 25 and 44), mutated to glycine in order to prevent S—S bonds which facilitates dimerization (SEQ ID NOs: 7-8), denoted herein as Alpha-gamma-2A-Gamma(mut). FIG. 8B shows representative images of B16-H2B-tdTomato target cells treated with an anti-TRP-1 antibody either alone or following 48 hours co-culturing with uninfected CD8+ T cells (Sham), CD8+ T cells infected with Alpha-2A-Gamma, Alpha-CD8-gamma, Alpha-gamma-2A-Gamma or Alpha-gamma-2A-Gamma (mut). Images were taken with bright light, red and green filters, ×200 magnitude. FIG. 8C is a graph showing target cell count following co-culturing with the CD8+ T cells described in FIG. 8B.

Figure 9:
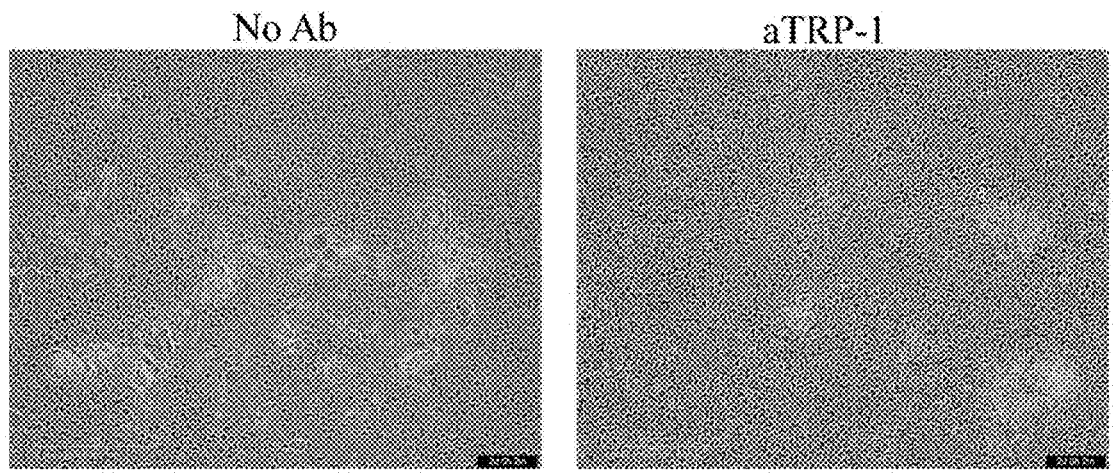

FIG. 9 demonstrates killing of YUMM1.7-H2B-tdTomato target cells by Alpha-gamma-2a-Gamma infected cells. Shown are representative images of YUMM1.7-H2B-tdTomato co-cultured for 2 days with Alpha-gamma-2A-Gamma infected CD8 T cells at an effector:target ratio 2:1, with or without an anti-TRP-1 antibody. Images were taken with bright light, red and green filters, showing target cells nuclear tdTomato and GFP in the infected T cells population.

Figure 10A:
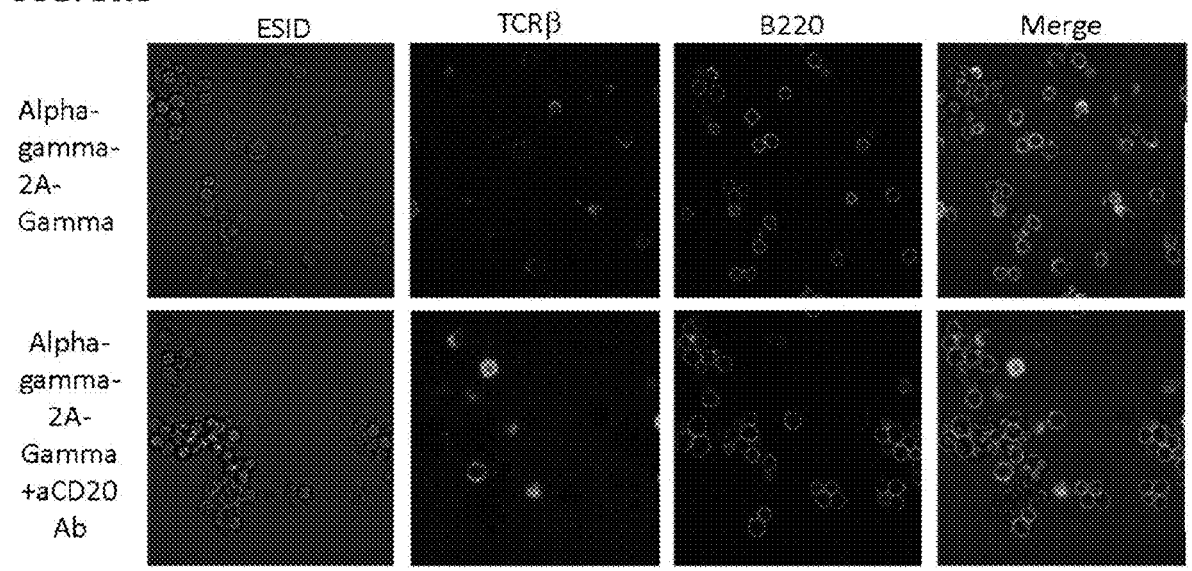
Figure 10B:
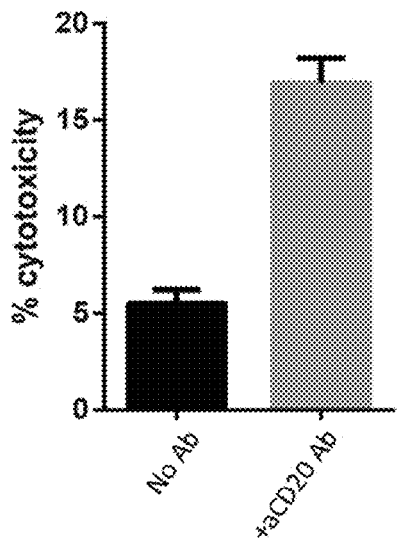

FIG. 10A-B demonstrate killing of A20 B-cell lymphoma target cells by Alpha-gamma-2a-Gamma infected cells. FIG. 10A shows representative confocal images of A20 cells co-cultured with CD8+ T cells infected with Alpha-gamma-2A-Gamma cells at an effector:target ratio 2:1, with or without an anti-CD20 antibody. The cells were stained for T cell marker TCRβ and B cell marker B220. ×200 magnitude. FIG. 10B shows flow cytometry analysis of A20 B-lymphoma cells AnnexinV staining following 24 hours of co-culturing with Alpha-gamma-2A-Gamma CD8+ T cells, with or without an anti-CD20 antibody.

Figure 11:
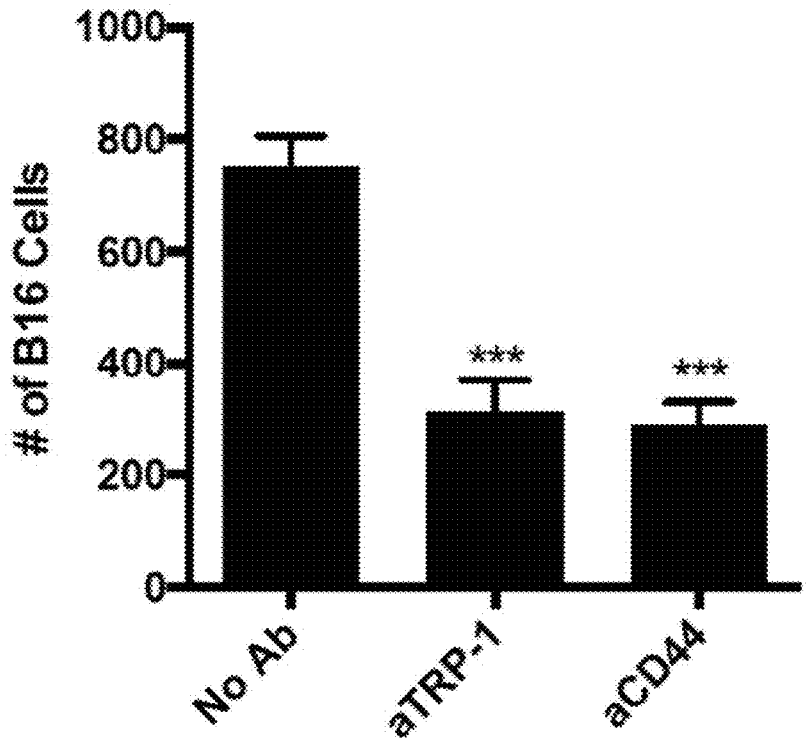

FIG. 11 demonstrates killing of B16 target cells by Alpha-gamma-2a-Gamma infected CD8+ T cells in combination with an anti-TRP-1 or with anti-CD44 antibody, following 24 hours of co-culturing.

Figure 12:
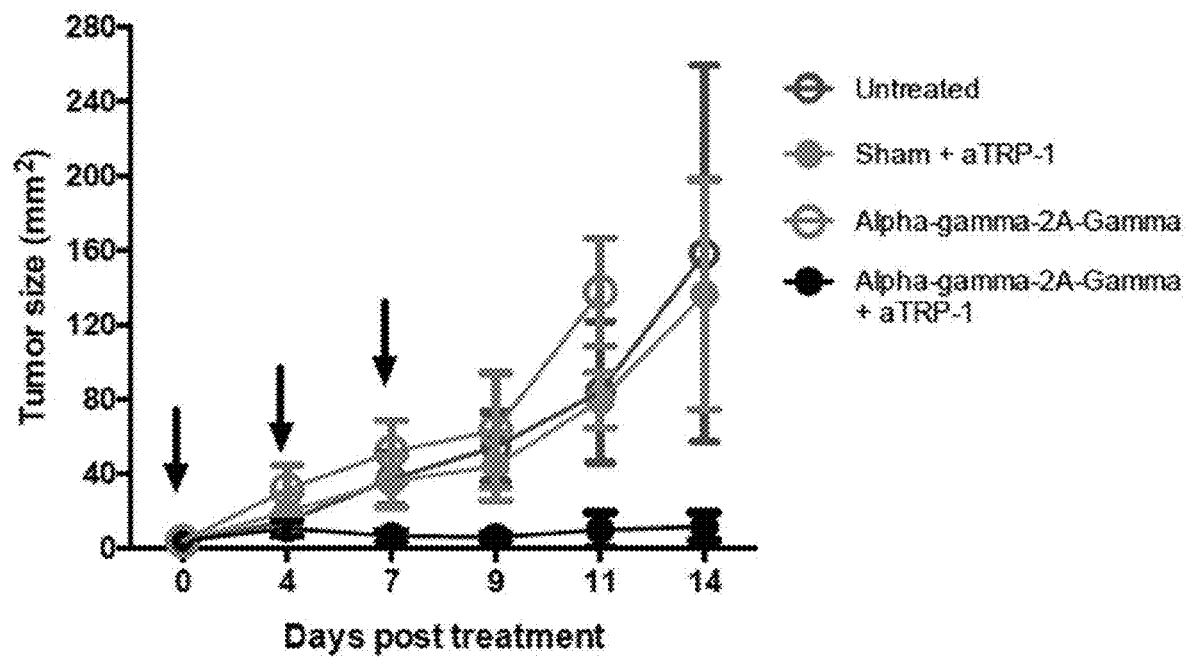

FIG. 12 demonstrates the in-vivo anti-tumor effect of Alpha-gamma-2a-Gamma infected T cells. Shown is the tumor size in mice injected sub-cutaneously with B16 cells ($2\times10^5$) and treated with alpha-gamma-2A-Gamma infected CD3+ T cells with or without an anti-TRP-1 antibody (n=4 in each group), as compared to untreated (n=3) or treatment with non-infected (sham) CD3+ T cells and an anti-TRP-1 antibody (n=3) controls. Mice treatment started 7 days following tumor cell injection and comprised 3 injections on days 7, 11, 14. CD3+ T cells were injected i.v. while anti-TRP-1 was injected sub-cutaneously.

Figure 13:
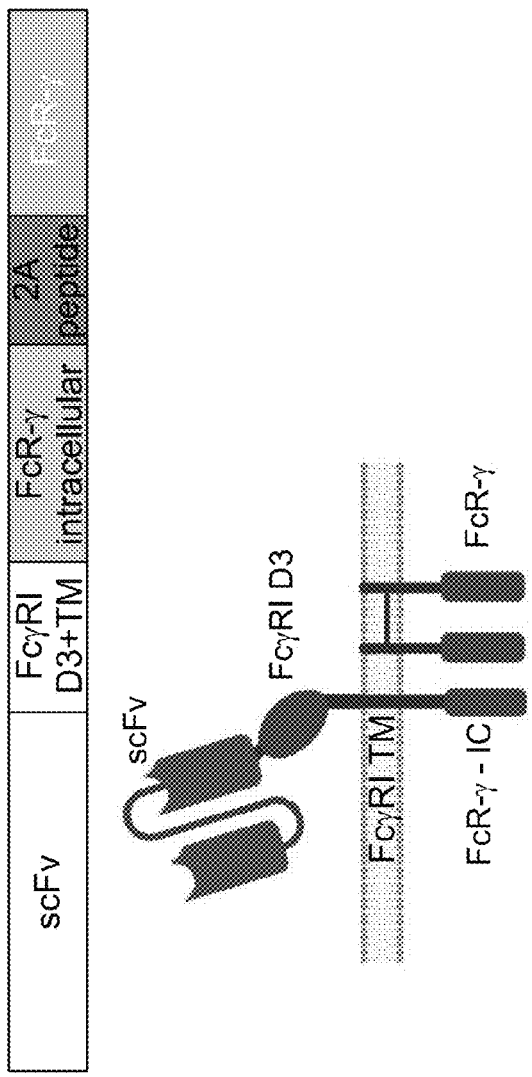

FIG. 13 shows a schematic representations of a construct encoding an anti-EGFR scFv fused to the extracellular D3 domain and transmembrane domain of FcγRI fused to the intracellular domain of FcRγ, T2A skipping peptide and FcRγ SEQ ID NOs: 37-38), denoted herein as scFv-alpha-gamma-2A-gamma.

Figure 14B:
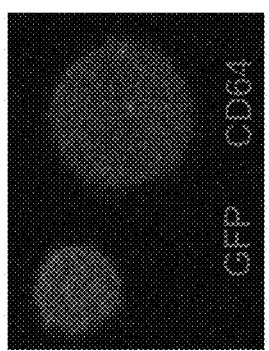
Figure 14C:
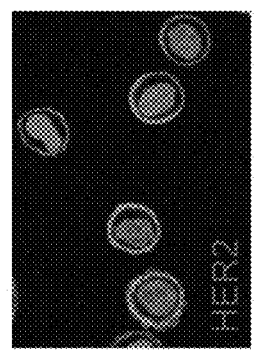
Figure 14D:
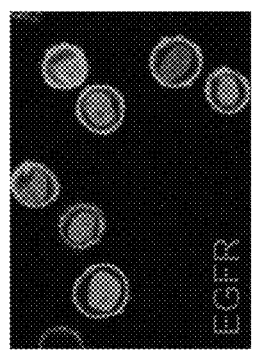
Figure 14A:
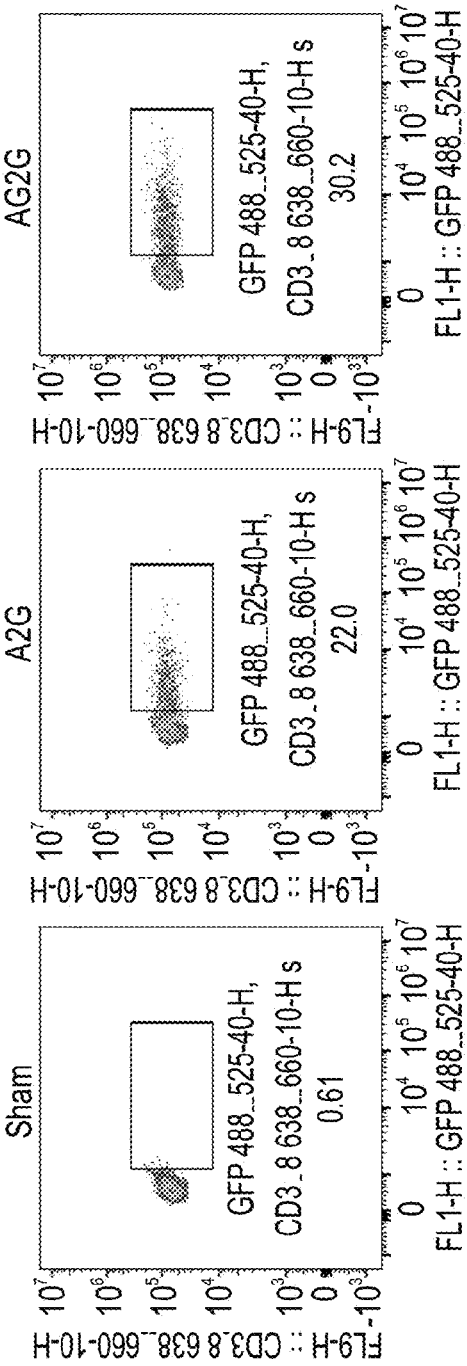
Figure 14E:
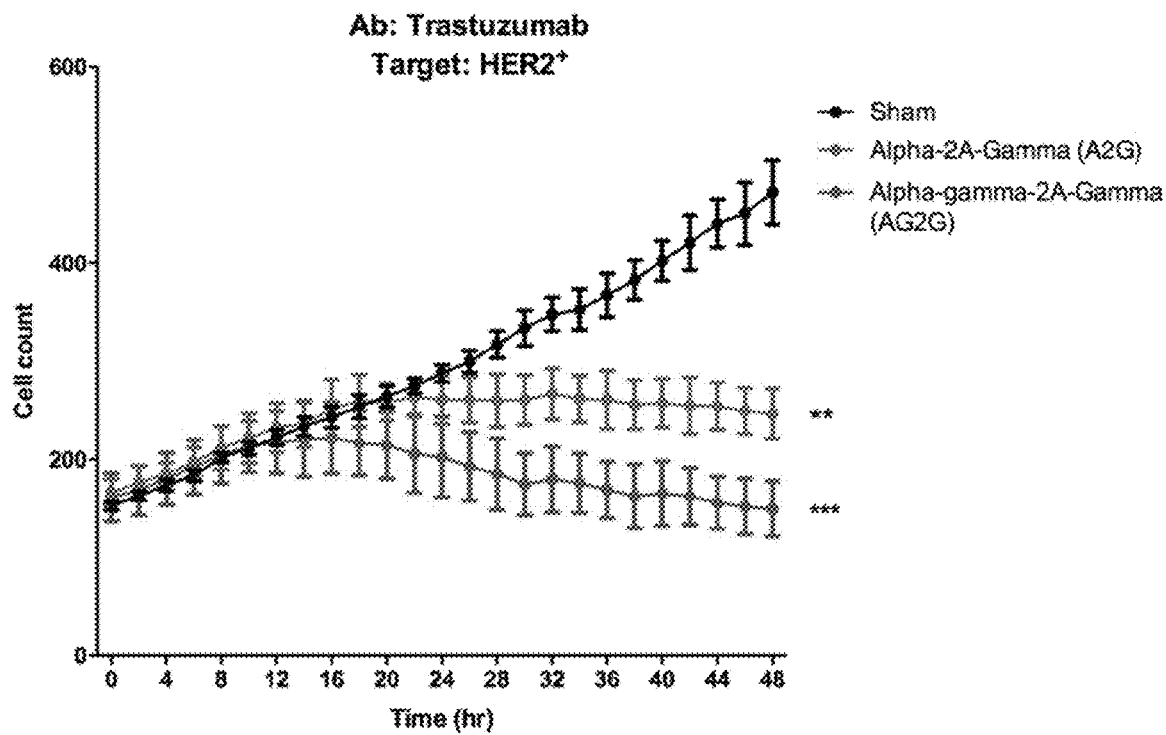
Figure 14F:
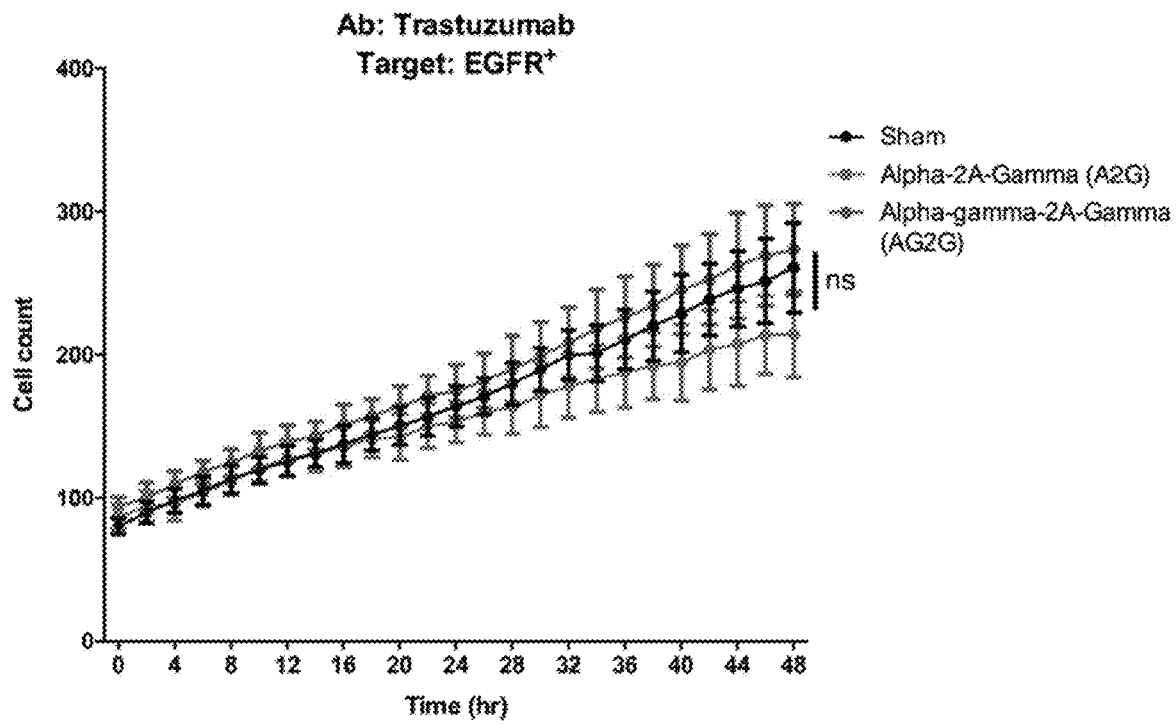

FIGS. 14A, 14B, 14C, 14D, 14E, and 14F demonstrate killing of HER2 target cells by Alpha-gamma-2a-Gamma (AG2G) infected T cells as compared to Alpha-2A-Gamma (A2G) infected T cells. FIG. 14A shows representative flow cytometry plots of human T cells infected with AG2G-IRES-GFP retrovirus, 10 days following infection. FIG. 14B shows a representative confocal microscopy image of human T cells infected with AG2G-IRES-GFP and stained for FcγRI (CD64). FIG. 14C shows a representative confocal microscopy image of human HT29 colon cancer cell line infected with HER2 and H2b-tdTomato, and stained for HER2. FIG. 14D shows a representative confocal microscopy image of human HT29 colon cancer cell line infected with EGFR and H2b-tdTomato, and stained for EGFR. FIG. 14E is a graph demonstrating the number of target cells counted by the incuCyte imager of HT29-H2b-tdTomato HER2 cells co-cultured with uninfected (sham) or A2G-IRES-GFP or AG2G-IRES-GFP-infected human T cells and treated with the relevant anti-HER2 antibody Trastuzumab (n=4). FIG. 14F is a graph demonstrating the number of target cells counted by the incuCyte imager of HT29-H2b-tdTomato EGFR HT29 cells co-cultured with sham or A2G or AG2G-IRES-GFP-infected human T cells and treated with the irrelevant anti-HER2 antibody Trastuzumab (n=4).

Figure 15A:
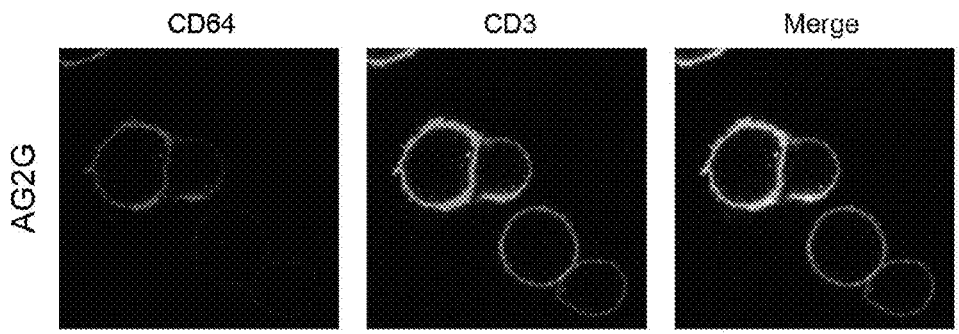
Figure 15B:
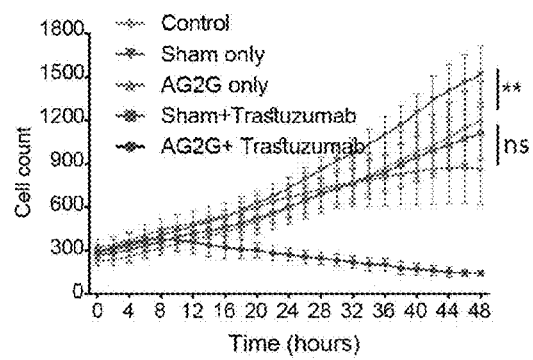
Figure 15C:
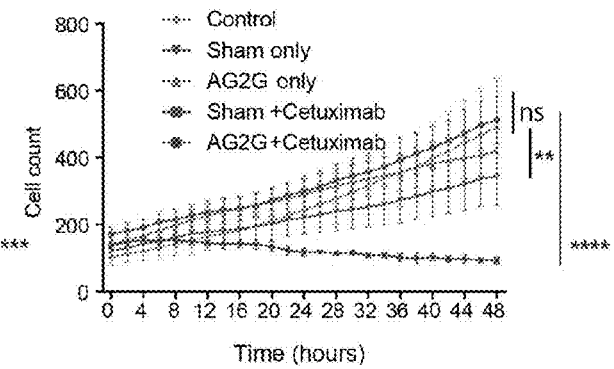
Figure 15D:
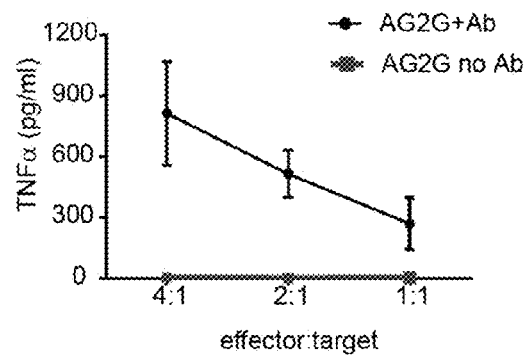
Figure 15E:
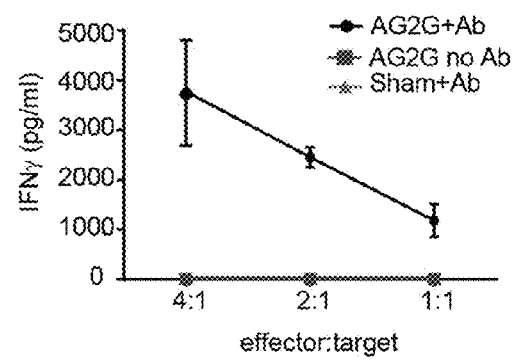
Figure 15F:
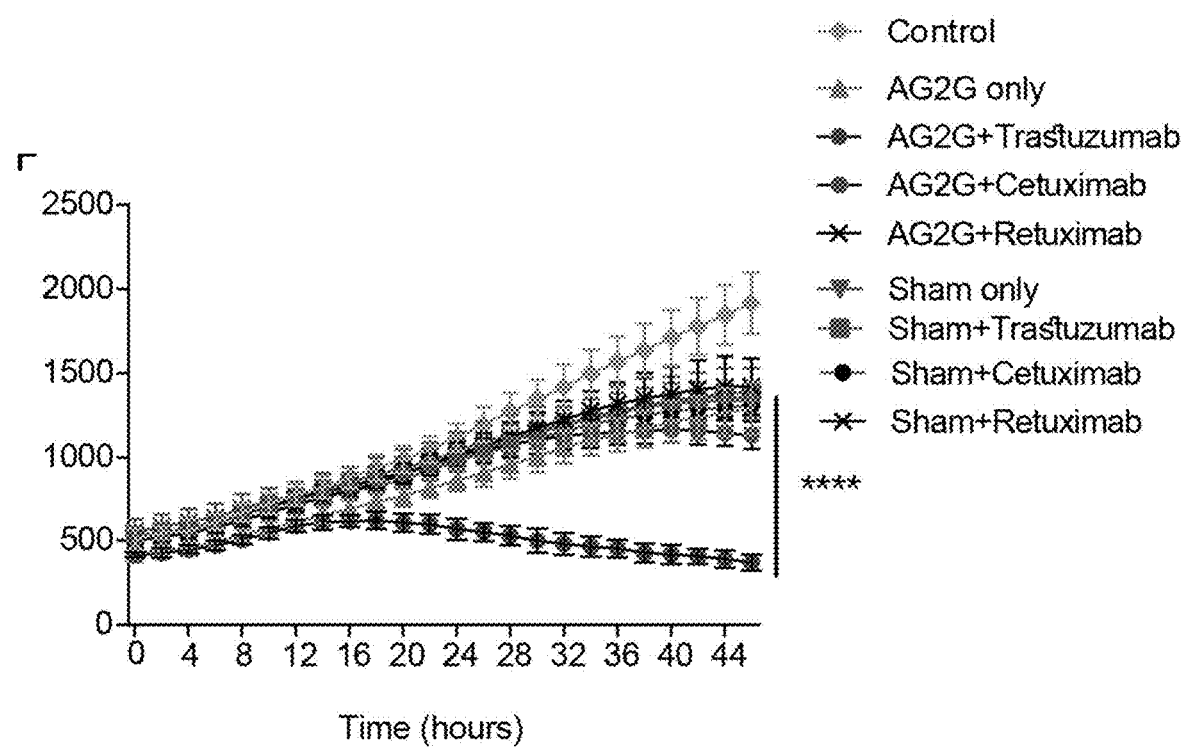

FIGS. 15A, 15B, 15C, 15D, 15E and 15F demonstrate killing of HER2 target cells and EGFR target cells by T cells infected with Alpha-gamma-2a-Gamma (AG2G) pMSVG.1 vector in combination with the relevant antibody. FIG. 15A shows representative confocal microscopy images of T cells infected with the pMSVG.1-AG2G construct and stained for CD64. FIG. 15B is a graph demonstrating the number of target cells counted by the incuCyte imager of H2b-tdTomato HER2+ HT29 cells co-cultured with sham or AG2G-infected human T cells with or without treatment with the relevant anti-HER2 antibody Trastuzumab (n=4). FIG. 15C is a graph demonstrating the number of target cells counted by the incuCyte imager of H2b-tdTomato HER2+ HT29 cells co-cultured with sham or AG2G-infected human T cells with or without treatment with the irrelevant anti-EGFR antibody Cetuximab (n=4). FIGS. 15D-E show graphs demonstrating TNFα (FIG. 15D) and IFNγ (FIG. 15E) concentration in supernatants of H2b-tdTomato HER2+ HT29 human colon carcinoma co-cultured with sham or AG2G-infected human T cells at effector:target ratio of 4:1, 2:1 or 1:1 with or without treatment with the relevant anti-HER2 antibody Trastuzumab, as determined by ELISA. FIG. 15F is a graph demonstrating the number of target cells counted by the incuCyte imager of H2b-tdTomato HER2+ HT29 cells co-cultured with sham or AG2G-infected human T cells with or without treatment with the relevant anti-HER2 antibody Trastuzuman or the irrelevant antibodies, Cetuximab or Retuximab.

Figure 16:
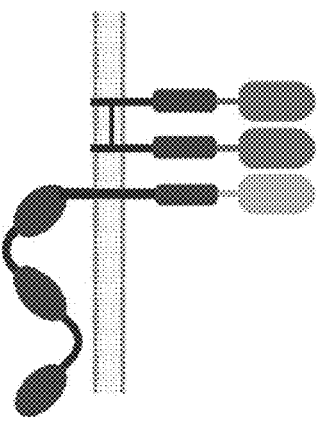

FIG. 16 shows schematic representations of costimulatory and cytokine receptor signaling domains that can be added to the polypeptide of some embodiments of the invention.

Figure 17:
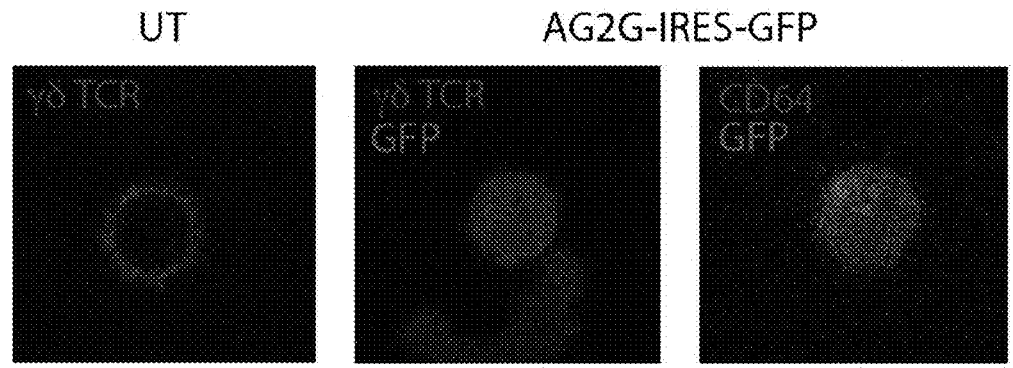

FIG. 17 shows GFP and FcγRI (CD64) expression in human 76T cells infected with the Alpha-gamma-2a-Gamma (AG2G)-IRES-GFP vector, 9 days following infection. Human PBMC from healthy donor were collected and γδ T cells isolated following expansion using Zoledronate and IL-2 were transduced with retrovirus for AG2G cloned in pMIGII vector, and were imaged for GFP expression and for γδ-TCR-APC or CD64-APC staining.

Figure 18A:
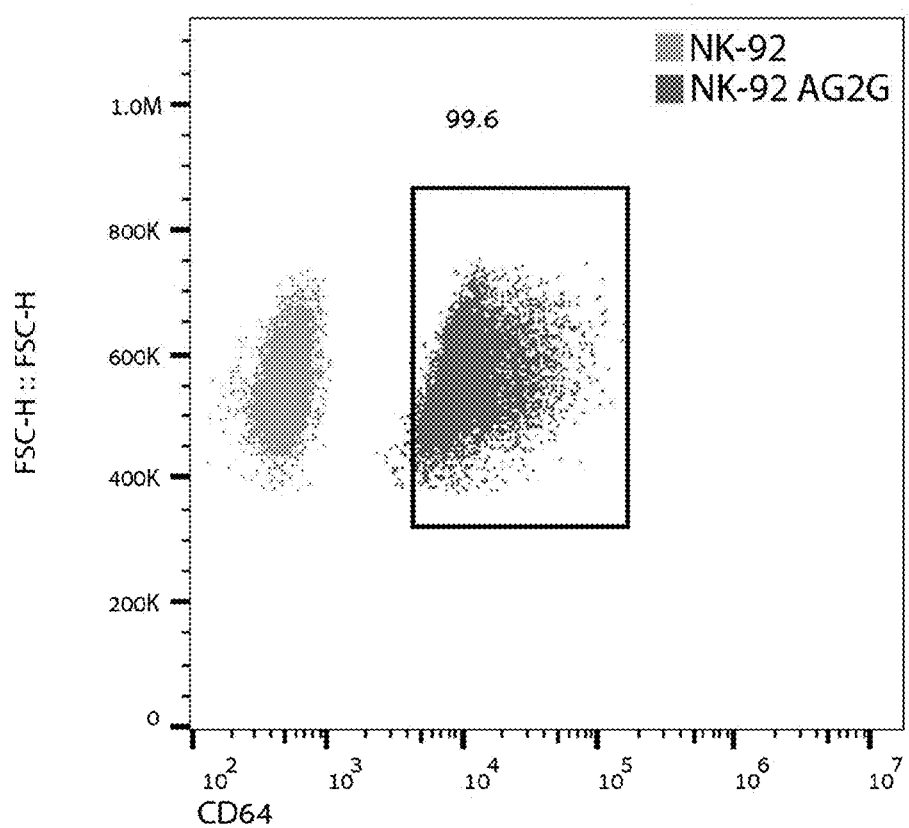
Figure 18B:
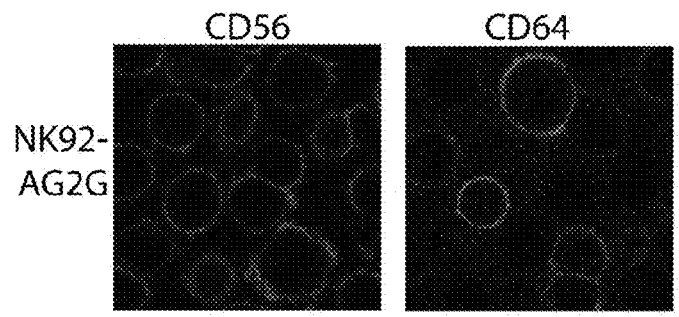

FIGS. 18A-B show CD56 and FcγRI (CD64) expression in NK-92 cell line infected with Alpha-gamma-2a-Gamma (AG2G) pMSVG.1 vector. FIG. 18A shows representative flow cytometry plot demonstrating expression of AG2G using an anti-CD64-APC antibody. FIG. 18B shows representative immunostaining images demonstrating expression of the NK marker CD56 using an anti-CD56-APC antibody and expression of AG2G using an anti-CD64-APC antibody.

DESCRIPTION OF SPECIFIC EMBODIMENTS OF THE INVENTION

The present invention, in some embodiments thereof, relates to multi subunit protein modules, cells expressing same and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Cancer immunotherapy, including cell-based therapy, antibody therapy and cytokine therapy, has emerged in the last couple of years as a promising strategy for treating various types of cancer. Antibody-based cancer immunotherapies depend on recognition of cell surface molecules that are differentially expressed on cancer cells relative to non-cancerous cells and/or immune-checkpoint blockade. On the other hand, cell-based therapy using e.g. T cells having a T cell receptor (TCR) specific for an antigen differentially expressed in association with an MHC class I molecule on cancer cells relative to non-cancerous cells were shown to exert anti-tumor effects in several types of cancers, e.g. hematologic malignancies. Strategies combining principles of antibody-based cancer immunotherapy and cell based therapy have been suggested.

Specific embodiments of the present teachings suggest that the formation of a three polypeptide structure each comprising an Fcγ chain activating domain, is surprisingly advantageous in comparison to a single polypeptide comprising an Fcγ chain activating domain or two polypeptides comprising an Fcγ chain activating domain (e.g. created by the dimerizing properties of the transmembrane domain of Fcγ chain).

As shown in the Examples section which follows, the present inventors have exogenously expressed in T cells a first polypeptide comprising the binding domain of the high affinity Fcγ receptor FcγRI (CD64) and a second distinct polypeptide comprising the Fcγ chain which is capable of forming a homodimer. These engineered T cells exerted in-vitro killing capabilities of tumor cells in combination with anti-tumor antibodies, which were advantageous to T cells exogenously expressing a single polypeptide comprising both the binding domain of FcγRI and the activating domain of Fcγ chain (Example 1 of the Examples section which follows). However, the present inventors discovered that by combining the two approaches and exogenously expressing a first polypeptide comprising both the binding domain of FcγRI and the activating domain of Fcγ chain and a second distinct polypeptide comprising Fcγ chain which is capable of forming a homodimer, the engineered T cells exerted more robust and in lower concentrations in-vitro killing capabilities (Example 1 of the Examples section which follows). Importantly, these cells also had a remarkable anti-tumor effect in an in-vivo mouse tumor model (Example 2 of the Examples section which follows).

Thus, according to an aspect of the present invention, there is provided a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain capable of binding a target that is presented on a cell surface of a target cell of an immune cell, such that upon binding of said extracellular binding domain to said target said activating signal is transmitted in an immune cell expressing said multi subunit protein module.

As used herein, the phrase "multi subunit protein module" refers to a plurality of at least three polypeptides which together have the activity of transmitting an activating signal in an immune cell expressing the multi subunit protein module upon binding of the extracellular domain to its target presented on a cell surface of a target cell.

According to specific embodiments, the multi subunit protein module comprises 3, 4, 5, 6 or more polypeptides.

According to a specific embodiment, the multi subunit protein module comprises 3 polypeptides.

According to specific embodiments, the plurality of polypeptides are complexed (or assembled) together (e.g. following binding of the extracellular binding domain to its target).

According to specific embodiments, wherein said at least one polypeptide is one polypeptide.

According to specific embodiments, wherein said at least two polypeptides is two polypeptides.

According to specific embodiments, wherein said at least three polypeptides is three polypeptides.

As used herein the phrase "Fc receptor common γ chain" abbreviated as "FcRγ" refers to the polypeptide expression product of the FCER1G gene (Gene ID 2207). According to specific embodiments, FcRγ is human FcRγ. According to a specific embodiment, the FcRγ protein refers to the human protein, such as provided in the following GenBank Number NP_004097 (SEQ ID NO: 11).

As used herein, the phrase "amino acid sequence of an Fc receptor common γ chain (FcRγ) capable of transmitting an activating signal" refers to full length FcRγ or a fragment thereof or a homolog thereof which comprises an intracellular domain and maintains at least the capability of transmitting an activating signal in a cell expressing an Fcγ receptor upon binding of the Fcγ receptor to a Fc ligand.

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodemosine, nor-valine, nor-leucine and ornithine. Furthermore, the term "amino acid" includes both D- and L-amino acids.

According to specific embodiments, the amino acid sequence of an Fc receptor common γ chain (FcRγ) capable of transmitting an activating signal comprises an ITAM motif.

As used herein the terms "activating" or "activation" refer to the process of stimulating a T cell that results in cellular proliferation, maturation, cytokine production, chemotaxis and/or induction of effector functions.

Methods of determining signaling of an activating signal are well known in the art, and include, but are not limited to, enzymatic activity assays such as kinase activity assays, and expression of molecules involved in the signaling cascade using e.g. PCR, Western blot, immunoprecipitation and immunohistochemistry. Additionally or alternatively, determining transmission of an activating signal can be effected by evaluating T cell activation or function. Methods of evaluating T cell activation or function are well known in the art and include, but are not limited to, proliferation assays such as CFSE staining, MTT, Alamar blue, BRDU and thymidine incorporation, cytotoxicity assays such as CFSE staining, chromium release, Calcin AM, cytokine secretion assays such as intracellular cytokine staining, ELISPOT and ELISA, expression of activation markers such as CD25, CD69, CD137, CD107a, PD1, and CD62L using flow cytometry.

According to specific embodiments, the amino acid sequence of FcRγ comprises full length FcRγ.

Thus, the polypeptide of some embodiments of the invention comprises full length FcRγ.

According to specific embodiments, the amino acid sequence of FcRγ comprises a fragment thereof or a homolog thereof which comprises an intracellular domain and maintains at least the capability of transmitting an activating signal in a cell expressing an Fcγ receptor upon binding of the Fcγ receptor to a Fc ligand.

The polypeptide of some embodiments of the invention comprises the intracellular domain of FcRγ capable of transmitting an activating signal and are devoid of the membranal and extracellular domains of FcRγ.

According to specific embodiments, the multi subunit protein module comprises at least one polypeptide comprising the intracellular domain of FcRγ capable of transmitting an activating signal and is devoid of the membranal and extracellular domains of FcRγ; and at least two polypeptides comprising full length FcRγ.

According to specific embodiments, the multi subunit protein module comprises a single polypeptide comprising the intracellular domain of FcRγ capable of transmitting an activating signal and is devoid of the membranal and extracellular domains of FcRγ; and two polypeptides comprising full length FcRγ.

According to specific embodiments, the amino acid sequence of FcRγ capable of transmitting an activating signal comprises SEQ ID NO: 12 or 39.

According to specific embodiments, the amino acid sequence of FcRγ capable of transmitting an activating signal consists of SEQ ID NO: 12 or 39.

The homolog (naturally occurring or synthetically/recombinantly produced) can be, for example, at least 50%, at least 55%, at least 60%, at least 65%, at least 70%, at least 75%, at least 80%, at least 85%, at least 90%, at least 95%, at least 96%, at least 97%, at least 98%, at least 99% or 100% identical or homologous to the polypeptide provided in SEQ ID NO: 11, 12 or 39 or a functional fragment thereof which exhibit the desired activity (i.e., comprises an intracellular domain and maintains at least the capability of transmitting an activating signal in a cell expressing an Fcγ receptor upon binding of the Fcγ receptor to a Fc ligand); or at least 50%, at least 55%, at least 60%, at least 65%, at least 70%, at least 75%, at least 80%, at least 85%, at least 90%, at least 95%, at least 96%, at least 97%, at least 98%, at least 99% or 100% identical to the polynucleotide sequence encoding same.

The homolog (naturally occurring or synthetically/recombinantly produced) can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide provided in SEQ ID NO: 11, 12 or 39 or a functional fragment thereof which exhibit the desired activity (i.e., comprises an intracellular domain and maintains at least the capability of transmitting an activating signal in a cell expressing an Fcγ receptor upon binding of the Fcγ receptor to a Fc ligand); or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

Sequence identity or homology can be determined using any protein or nucleic acid sequence alignment algorithm such as Blast, ClustalW, and MUSCLE.

The homolog may also refer to an ortholog, a deletion, insertion, or substitution variant, including a conservative and non-conservative amino acid substitution, as further described hereinbelow.

According to specific embodiments, the amino acid sequence of FcRγ may comprise conservative and/or non-conservative amino acid substitutions.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute an amino acid sequence capable of binding α4β7 integrin.

At least one but not all of the at least three cell membrane polypeptides comprised in the multi subunit protein module disclosed herein comprises an extracellular binding domain capable of binding a target that is presented on a cell surface of a target cell of an immune cell.

According to specific embodiments, one of the at least three cell membrane polypeptides comprised in the multi subunit protein module disclosed herein comprises an extracellular binding domain capable of binding a target that is presented on a cell surface of a target cell of an immune cell.

Thus, according to specific embodiments, the cell membrane polypeptide comprises an extracellular binding domain capable of binding a target that is presented on a cell surface of a target cell of an immune cell.

According to other specific embodiments, the cell membrane polypeptide is devoid of an extracellular binding domain capable of binding a target that is presented on a cell surface of a target cell of an immune cell.

According to a specific embodiment, the multi subunit protein module comprises three cell membrane polypeptides each comprising an amino acid sequence of an FcRγ, wherein one of the cell membrane polypeptides further comprises an extracellular binding domain capable of binding a target that is presented on a cell surface of a target cell of an immune cell and the other two cell membrane polypeptides are devoid of such an extracellular binding domain.

As used herein, the phrase "extracellular binding domain capable of binding a target" refers to a proteinaceous moiety having a binding affinity (e.g., below $10^{-4}$ nM) to a target of interest being presented on a target cell. Non-limiting examples of binding domains include the binding domain of a receptor, the binding domain of a ligand, the binding domain of a hormone (e.g. leptin) and an antigen binding moiety such an antibody, as further described hereinbelow.

Assays for testing binding are well known in the art and include, but not limited to flow cytometry, bio-layer interferometry Blitz® assay, HPLC, surface plasmon resonance (e.g. Biacore).

According to specific embodiments, the extracellular binding domain of binds the target presented on the cell with a Kd $>10^{-6}$ M, $>10^{-7}$ M, $>10^{-8}$ M or $>10^{-9}$ M, each possibility represents a separate embodiment of the present invention.

According to specific embodiments, the extracellular binding domain binds the target presented on the cell with a Kd >$10^{-9}$ M.

As used herein, the phrase "target cell of an immune cell" refers to a cell which upon recognition by an immune cell causes activation of the immune cell via the multi subunit protein module described herein.

According to specific embodiments, the target cell is a pathologic (diseased) cell.

According to specific embodiments, the target cell is a cancerous cell.

As used herein, the term "presented" refers to a target expressed by the target cell (e.g. an antigen) or bound to (yet not expressed by it) the target cell (e.g. an antibody which binds an antigen expressed by the target cell).

According to specific embodiments, the target is over-presented or only presented on the cell surface of the target cells as compared to other cells (e.g. healthy cells).

Methods of determining cell surface presentation are well known in the art and include, but not limited to flow cytometry and immuno-cytochemistry.

According to specific embodiments, the binding domain is of an antibody and the target is an antigen.

According to other specific embodiments, the extracellular binding domain is not an antibody binding domain.

According to specific embodiments, the multi subunit protein module is devoid of an antibody binding domain.

The term "antibody" as used in this invention includes intact molecules as well as functional fragments thereof (that are capable of binding to an epitope of an antigen).

As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

According to specific embodiments, the antibody is a whole or intact antibody.

According to specific embodiments, the antibody comprises an Fc domain.

According to specific embodiments, the antibody is an antibody fragment.

According to a specific embodiment, the antibody fragments include, but are not limited to, single chain, Fab, Fab' and F(ab')$_2$ fragments, Fd, Fcab, Fv, dsFv, scFvs, diabodies, minibodies, nanobodies, Fab expression library or single domain molecules such as VH and VL that are capable of binding to an epitope of the antigen in an HLA restricted manner.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv (scFv), a disulfide-stabilized Fv (dsFv), an Fab, an Fab', and an F(ab')2, or antibody fragments comprising the Fc region of an antibody.

According to specific embodiments, the identity of the amino acid residues in the antibody that make up the variable region and/or the CDRs is determined by the method of Kabat et al. (See, e.g., Kabat et al., 1992, Sequences of Proteins of Immunological Interest, 5th ed., Public Health Service, NIH, Washington D.C.).

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds);

(vii) Single domain antibodies or nanobodies are composed of a single VH or VL domains which exhibit sufficient affinity to the antigen; and (viii) Fcab, a fragment of an antibody molecule containing the Fc portion of an antibody developed as an antigen-binding domain by introducing antigen-binding ability into the Fc region of the antibody.

According to specific embodiments, the extracellular binding domain capable of binding the target comprises a scFv.

According to other specific embodiments, the extracellular binding domain is not an scFv.

According to specific embodiments, the multi subunit protein module is devoid of an scFv.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

It will be appreciated that for human therapy, humanized antibodies are preferably used.

According to specific embodiments, the antibody is a humanized antibody. Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

According to specific embodiments, the antibody is a human antibody.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to specific embodiments, the antibody binds an antigen overexpressed or only expressed by a pathologic cell e.g. cancerous cell.

Non-limiting examples for known cancer antigens include MAGE-AI, MAGE-A2, MAGE-A3, MAGE-A4, MAGE-AS, MAGE-A6, MAGE-A7, MAGE-AS, MAGE-A9, MAGE-AIO, MAGE-All, MAGE-A12, GAGE-I, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), MAGE-Cl/CT7, MAGE-C2, NY-ES0-1, LAGE-1, SSX-1, SSX-2(HOM-MEL-40), SSX-3, SSX-4, SSX-5, SCP-1 and XAGE, melanocyte differentiation antigens, p53, ras, CEA, MUCI, PMSA, PSA, tyrosinase, Melan-A, MART-I, gplOO, gp75, alphaactinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-All, hsp70-2, KIAA0205, Mart2, Mum-2, and 3, neo-PAP, myosin class I, OS-9, pml-RAR alpha fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, plSOerbB-3, c-met, nm-23H1, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, C0-029, FGF-5, 0250, Ga733 (EpCAM), HTgp-175, M344, MA-50, MG7-Ag, MOV18, NB\170K, NYCO-I, RCASI, SDCCAG16, TA-90 (Mac-2 binding protein\cyclophilin C-associated protein), TAAL6, TAG72, TLP, TPS, tyrosinase related proteins, TRP-1, or TRP-2.

According to specific embodiments, the antibody binds EGFR, TRP-1, CD44, PDL-1, HER-2, MUC-1, MUC-16, CEA or EpCAM.

According to specific embodiments, the antibody binds EGFR.

According to specific embodiments, the antibody is an anti-EGFR comprising a variable heavy chain comprising SEQ ID NO: 41 and/or variable light chain comprising SEQ ID NO: 42.

According to a specific embodiment, the extracellular binding domain capable of binding the target comprises an anti-EGFR scFv comprising SEQ ID NO: 43.

According to other specific embodiments, the extracellular binding domain is of a ligand and the target is a receptor of the ligand. Non-limiting examples of such ligand-receptor pairs that can be used for targeting cancerous cells include a ligand of a tyrosine kinase receptor-tyrosine kinase receptor, EGF-EGFR, CD19 ligand-CD19, hyaluronic acid-CD44.

According to other specific embodiments, the extracellular binding domain is of a receptor and said target is a ligand of the receptor. Non-limiting examples of such receptor-ligand pairs that can be used for targeting cancerous cells include PD-1-PDL-1, CD137-CD137L, integrin alpha2beta1-E-Cadherin.

According to specific embodiments, the target is bound to the target cell. Thus, for example, the target may be an antibody or an Fc-fusion which is capable of binding an antigen expressed by a target cell.

Thus, according to specific embodiments, the extracellular binding domain is of an Fcγ receptor and the target is an Fc ligand bound to a target cell.

As used herein the phrase "extracellular binding domain of Fcγ receptor" refers to at least a fragment of an Fcγ receptor which comprises an extracellular domain capable of binding an Fc ligand.

As used herein, the term "Fc ligand" refers to an Fc domain such as of an antibody.

According to specific embodiments, the Fc ligand is an IgG Fc domain.

As used herein, the term "Fcγ receptor" refers to a cell surface receptor which exhibits binding specificity to the Fc domain of an IgG antibody. Examples of Fcγ receptors include, without limitation, CD64A, CD64B, CD64C, CD32A, CD32B, CD16A, and CD16B. The term "Fcγ receptor" also encompasses functional homologues (naturally occurring or synthetically/recombinantly produced) and/or Fc receptors comprising conservative and non-conservative amino acid substitutions, which exhibit the desired activity (i.e., capability of binding an IgG Fc binding domain).

According to specific embodiments, the Fcγ receptor is CD64.

As used herein, the term "CD64", also known as FcγRI, refers to the polypeptide expression product of the FCGR1A, FCGR1B or FCGR1C gene (Gene ID 2209, 2210, 2211, respectively), and includes CD64A, CD64B and CD64C. Full length CD64 comprises an extracellular, transmembrane and an intracellular domain and is capable of at least binding an IgG (IgG1 and IgG3) Fe domain and recruiting an FcRγ. Methods of determining binding and recruitment of an FcRγ are well known in the art and are also described hereinabove and below.

According to specific embodiments, CD64 is human CD64. According to a specific embodiment, the CD64 protein refers to the human CD64A protein, such as provided in the following UniProt Number P12314.

According to a specific embodiment, the CD64 protein refers to the human CD64B protein, such as provided in the following UniProt Number Q92637.

According to a specific embodiment, the CD64 protein refers to the human CD64C protein, such as provided in the following GenBank Number XM_001133198.

The extracellular domain of full length CD64 comprises three immunoglobulin (Ig) domains referred to as D1-D3 from N to C.

According to specific embodiments, the extracellular binding domain of CD64 comprises all Ig domains D1-D3.

According to specific embodiments, the extracellular binding domain of CD64 comprises SEQ ID NO: 14, 44 or 64.

According to specific embodiments, the extracellular binding domain of CD64 consists of SEQ ID NO: 14, 44 or 64.

According to specific embodiments, the extracellular binding domain of CD64 comprises SEQ ID NO: 14 or 44.

According to specific embodiments, the extracellular binding domain of CD64 consists of SEQ ID NO: 14 or 44.

According to specific embodiments, the extracellular binding domain of CD64 comprises the two Ig domains D1-D2.

According to specific embodiments, the extracellular binding domain of CD64 comprises SEQ ID NO: 45 or 46.

According to specific embodiments, the extracellular binding domain of CD64 consists of SEQ ID NO: 45 or 46.

The term "extracellular binding domain of CD64" also encompasses functional homologues (naturally occurring or synthetically/recombinantly produced), which exhibit the desired activity (i.e., binding an IgG Fc domain). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID No: 14, 44, 64, 45 or 46; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

According to specific embodiments, the extracellular binding domain of CD64 may comprise conservative and non-conservative amino acid substitutions.

According to specific embodiments, the at least one polypeptide comprising the extracellular binding domain comprises an amino acid sequence capable of recruiting other polypeptides comprising the amino acid sequence of FcRγ being part of the multi subunit protein module upon binding of the binding domain to the target.

Such recruitment will form a complex upon binding of the extracellular binding domain to the target, enabling transmission of an activating signal by the amino acid sequence of an FcRγ in an immune cell expressing the multi subunit protein module.

According to a specific embodiment, the recruitment refers to oligomerization e.g., trimerization of the at least three polypeptides being part of the multi subunit protein module.

According to specific embodiments, the amino acid sequence capable of recruiting the other polypeptides directly recruits the other polypeptide (i.e. without an intermediate polypeptide).

Such amino acid sequences are well known to the skilled in the art and include for example the transmembrane and/or the cytoplasmic domains of several Fc receptors such as, but not limited to CD64, CD16A, CD16B, FcεRIβ, FcαRI (CD89).

According to specific embodiments, the amino acid sequence capable of recruiting the other polypeptides is not of an Fcε receptor (FcεR).

Methods of determining recruitment of the polypeptides are well known in the art, and include, but are not limited to, enzymatic activity assays such as kinase activity assays, and expression of molecules involved in the signaling cascade using e.g. PCR, Western blot, immunoprecipitation and immunohistochemistry. Additionally or alternatively, determining recruitment of the polypeptides can be effected by evaluating cell activation or function by methods well known in the art such as, but not limited to proliferation assays such as CFSE staining, MTT, Alamar blue, BRDU and thymidine incorporation, cytotoxicity assays such as CFSE staining, chromium release, Calcin AM, and the like. Exemplary methods for determining recruitment are disclosed in e.g. in Kim, M. K., et al. (2003) Blood 101(11): 4479-4484; and Harrison, P. T., et al. (1995) Mol Membr Biol 12(4): 309-312, the contents of which are fully incorporated herein by reference.

According to specific embodiments, the amino acid sequence capable of recruiting the other polypeptides comprising the amino acid sequence of FcRγ comprises the transmembrane domain of an Fc receptor.

According to specific embodiments, the amino acid sequence capable of recruiting the other polypeptides comprising the amino acid sequence of FcRγ comprises the transmembrane domain of an Fcγ receptor.

According to specific embodiments, the amino acid sequence capable of recruiting the other polypeptides comprising the amino acid sequence of FcRγ comprises the transmembrane domain of CD64.

According to specific embodiments, the amino acid sequence capable of recruiting the other polypeptides comprising the amino acid sequence of FcRγ consists of the transmembrane domain of CD64.

According to specific embodiments, the amino acid sequence capable of recruiting the other polypeptides comprises an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 16 or 47.

According to specific embodiments, the amino acid sequence capable of recruiting the other polypeptides comprises SEQ ID NO: 16 or 47.

According to specific embodiments, the amino acid sequence capable of recruiting the other polypeptides consists of SEQ ID NO: 16 or 47.

According to specific embodiments, both the extracellular binding domain and the amino acid sequence capable of recruiting the other polypeptides are of CD64.

Hence, according to specific embodiments, the at least one polypeptide which comprises the extracellular binding domain comprises the extracellular and the transmembrane domains of CD64.

According to specific embodiments, the at least one polypeptide which comprises the extracellular binding domain comprises an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18 or 48.

According to specific embodiments, the at least one polypeptide which comprises the extracellular binding domain comprises SEQ ID NO: 18 or 48.

According to specific embodiments, the at least one polypeptide which comprises the extracellular binding domain comprises an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 19 or 49.

According to specific embodiments, the at least one polypeptide which comprises the extracellular binding domain comprises SEQ ID NO: 19 or 49.

According to specific embodiments, the at least one polypeptide which comprises the extracellular binding domain consists of SEQ ID NO: 19 or 49.

According to specific embodiments, at least two of the polypeptides in the multi subunit module are capable of forming a dimer.

The dimer may be a homodimer or a heterodimer.

According to specific embodiments, the dimer is a homodimer.

Thus, according to specific embodiments, at least two of the at least three cell membrane polypeptides comprising the amino acid sequence of FcRγ comprise a dimerizing moiety.

According to specific embodiments, the polypeptides devoid of the extracellular the binding domain are capable of forming a dimer.

Hence, according to specific embodiments, the polypeptides comprising the amino acid sequence of FcRγ and not comprising the binding domain comprise a dimerizing moiety.

As used herein, the term "dimerizing moiety" refers to an amino acid sequence capable of forming a polypeptide dimer. Such an amino acid may include for example an amino acid sequence comprising at least two cysteine residues enabling the formation of a disulfide bond between the thiol groups. Methods of determining dimerization are known in the art, including but not limited to immunoprecipitation, size exclusion chromatography, fast protein liquid chromatography (FPLC), multi-angle light scattering (SEC-MALS) analysis, SDS-PAGE analysis, nano-DSF, yeast two-hybrid system (e.g. RRS) and flow cytometry.

It will be appreciated that the dimerizing moiety of some embodiments of the invention is also capable of forming multimers (e.g., at least three).

Any known dimerizing moiety known in the art can be used with specific embodiments of the invention. A non-limiting example of such a dimerizing moiety which can be used with specific embodiments of the invention include an amino acid sequence of a transmembrane domain of FcRγ.

Thus, for example, according to specific embodiments, the dimerizing moiety comprises an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 21 or 50.

According to specific embodiments, the dimerizing moiety comprises SEQ ID NO: 21 or 50.

According to specific embodiments, the dimerizing moiety consists of SEQ ID NO: 21 or 50.

The multi subunit protein module of some embodiments of the invention comprises the following combination of elements: the binding domain is of an Fcγ receptor (e.g. CD64) and the target is an Fc ligand; the at least one polypeptide comprising said binding domain comprises a transmembrane domain of an Fcγ receptor (e.g. CD64); and the polypeptides comprising said amino acid sequence of FcRγ and not comprising said binding domain comprise as a dimerizing moiety an amino acid sequence of a transmembrane domain of said FcRγ.

Hence, according to an aspect of the present invention, there is provided a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises a transmembrane domain of CD64 and an extracellular binding domain of CD64 capable of binding an Fc ligand; and wherein said polypeptides comprising said amino acid sequence of FcRγ and not comprising said binding domain comprise as a dimerizing moiety an amino acid sequence of a transmembrane domain of said FcRγ, such that upon binding of said extracellular binding domain to said Fc ligand said activating signal is transmitted in an immune cell expressing said multi subunit protein module.

According to specific embodiments, at least one of the polypeptides in the multi subunit protein module comprises an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 23, 51 or 71.

According to specific embodiments, at least one of the polypeptides in the multi subunit protein module comprises SEQ ID NO: 23, 51 or 71.

According to specific embodiments, at least one of the at least three cell membrane polypeptides in the multi subunit protein module consists of SEQ ID NO: 23, 51 or 71.

According to specific embodiments, at least two of the polypeptides in the multi subunit protein module comprise an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 23, 51 or 71.

According to specific embodiments, at least two of the polypeptides in the multi subunit protein module comprise SEQ ID NO: 23, 51 or 71.

According to specific embodiments, at least two of the at least three cell membrane polypeptides in the multi subunit protein module consist of SEQ ID NO: 23, 51 or 71.

A specific example of a multi subunit protein module encompassed by specific embodiments of the present invention comprises:
(i) A polypeptide dimer wherein each of the polypeptides in the dimer comprises an amino acid sequence of FcRγ capable of transmitting an activating signal (e.g. FcRγ intracellular domain) and a dimerizing moiety (e.g. FcRγ transmembrane domain); and
(ii) A polypeptide comprising an extracellular binding domain capable of binding a target presented by a target cell of an immune cell (e.g. CD64 extracellular domain, scFv), an amino acid sequence capable of recruiting the polypeptide dimer following binding of the binding domain the target (e.g. CD64 transmembrane domain) and an amino acid sequence of FcRγ capable of transmitting an activating signal (e.g. FcRγ intracellular domain),
such that upon binding of the extracellular binding domain to the target the activating signal is transmitted in an immune cell expressing the multi subunit protein module.

According to specific embodiments, the multi subunit protein module comprises:
(i) A polypeptide dimer wherein each of the polypeptides in the dimer comprises an FcRγ intracellular domain and a FcRγ transmembrane domain; and
(ii) A polypeptide comprising a CD64 extracellular domain, a CD64 transmembrane domain and an FcRγ intracellular domain.

A non-limiting example of such a multi subunit protein module is schematically demonstrated in FIG. 2B.

According to specific embodiments, each of the polypeptides in the polypeptide dimer of (i) comprises SEQ ID NO: 23, 51 or 71 and the polypeptide of (ii) comprises SEQ ID NO: 19 or 49.

According to specific embodiments, each of the polypeptides in the polypeptide dimer of (i) consists of SEQ ID NO: 23, 51 or 71 and the polypeptide of (ii) consists of SEQ ID NO: 19 or 49.

According to specific embodiments, the multi subunit protein module comprises:
(i) A polypeptide dimer wherein each of the polypeptides in the dimer comprises an FcRγ intracellular domain and a FcRγ transmembrane domain; and
(ii) A polypeptide comprising a scFv, a CD64 transmembrane domain and an FcRγ intracellular domain.

A non-limiting example of such a multi subunit protein module is schematically demonstrated in FIG. 13.

According to specific embodiments, each of the polypeptides in the polypeptide dimer of (i) comprises SEQ ID NO: 23, 51 or 71 and the polypeptide of (ii) comprises SEQ ID NO: 52.

According to specific embodiments, each of the polypeptides in the polypeptide dimer of (i) consists of SEQ ID NO: 23, 51 or 71 and the polypeptide of (ii) consists of SEQ ID NO: 52.

According to specific embodiments, any of the polypeptides disclosed herein can comprise a co-stimulatory signaling domain.

According to specific embodiments, the at least one polypeptide comprising the extracellular binding domain comprises a co-stimulatory signaling domain.

According to specific embodiments, the polypeptide devoid of the extracellular binding domain comprises a co-stimulatory signaling domain.

According to other specific embodiments, the polypeptides disclosed herein do not comprise a co-stimulatory signaling domain.

According to specific embodiments, the at least one polypeptide comprising the extracellular binding domain does not comprise a co-stimulatory signaling domain.

According to specific embodiments, the polypeptide devoid of the extracellular binding domain does not comprise a co-stimulatory signaling domain.

As used herein, the phrase "co-stimulatory signaling domain" refers to an amino acid sequence of a co-stimulatory molecule capable of transmitting a secondary stimulatory signal resulting in activation of an immune cell (e.g. T cell). Typically, a co-stimulatory signaling domain does not comprise an ITAM domain.

Any known co-stimulatory signaling domain can be used with specific embodiments of the present invention. Non-limiting examples of co-stimulatory signaling domains include 4-1BB, CD28, OX40, ICOS, CD27, GITR, HVEM, TIM1, LFA1(CD11a), CD2. Non-limiting schematic representations of costimulatory domains that can be added to the polypeptide of some embodiments of the invention are provided in FIG. 16.

According to specific embodiments, the co-stimulatory signaling domain is of 4-1BB and/or OX40.

Non-limiting examples of specific sequences of co-stimulatory signaling domains are provided in SEQ ID NOs: 25 (OX40), SEQ ID NO: 26 (4-1BB).

According to specific embodiments, any of the polypeptides disclosed herein can comprise a cytokine receptor signaling domain.

According to specific embodiments, the at least one polypeptide comprising the extracellular binding domain comprises a cytokine receptor signaling domain.

According to specific embodiments, the polypeptide devoid of the extracellular binding domain comprises cytokine receptor signaling domain.

According to other specific embodiments, the polypeptides disclosed herein do not comprise a cytokine receptor signaling domain.

According to specific embodiments, the at least one polypeptide comprising the extracellular binding domain does not comprise a cytokine receptor signaling domain.

According to specific embodiments, the polypeptide devoid of the extracellular binding domain does not comprise a cytokine receptor signaling domain.

As used herein, the phrase "cytokine receptor signaling domain" refers to an amino acid sequence of a cytokine receptor capable of transmitting a stimulatory signal resulting in activation of the T cell.

Any known cytokine receptor signaling domain can be used with specific embodiments of the present invention. Non-limiting examples of cytokine receptor signaling domains include IL2rg that is the IL2 receptor common gamma chain (e.g. such as provided e.g. in SEQ ID NO: 27), the Toll/IL1 receptor homology domain (TIR) that is the signaling domain of the myd88 receptor, TNF receptor intracellular domain (e.g. such as provided in SEQ ID NO: 28), IL12-Rb1 intracellular domain (e.g. such as provided in SEQ ID NO: 29), IL12-Rb1 intracellular domain (e.g. such as provided in SEQ ID NO: 30), IL23 receptor intracellular domain (e.g. such as provided in SEQ ID NO: 31), IFNγ receptor 1 intracellular domain (e.g. such as provided in SEQ ID NO: 32), IFNγ receptor 2 intracellular domain (e.g. such as provided in SEQ ID NO: 33), IL2Rb intracellular domain (e.g. such as provided in SEQ ID NO: 34), IL1 receptor intracellular domain (e.g. such as provided in SEQ ID NO: 35), IL1AcP receptor intracellular domain (e.g. such as provided in SEQ ID NO: 36).

Non-limiting schematic representations of cytokine receptor signaling domains that can be added to the polypeptide of some embodiments of the invention are provided in FIG. 16.

Any of the components comprised in a single polypeptide as described herein may be linked to each other directly of via a linker, each possibility represents a separate embodiment of the present invention.

Any linker known in the art can be used with specific embodiments of the invention.

According to specific embodiments, the linker may be derived from naturally-occurring multi-domain proteins or is an empirical linker as described, for example, in Chichili et al., (2013), Protein Sci. 22(2): 153-167, Chen et al, (2013), Adv Drug Deliv Rev. 65(10): 1357-1369, the entire contents of which are hereby incorporated by reference. In some embodiments, the linker may be designed using linker designing databases and computer programs such as those described in Chen et al., (2013), Adv Drug Deliv Rev. 65(10): 1357-1369 and Crasto et al., (2000), Protein Eng. 13(5):309-312, the entire contents of which are hereby incorporated by reference.

According to specific embodiments, the linker is a synthetic linker.

According to specific embodiments, the linker is a polypeptide.

Non-limiting examples of linkers that can be used include AS, GS, (GGGGS)$_n$ (n=1-4) (SEQ ID NO: 53), GGGGSGGGG (SEQ ID NO: 54), (Gly)$_8$ (SEQ ID NO: 55), (Gly)$_6$ (SEQ ID NO: 56), (EAAAK)$_n$ (n=1-3) (SEQ ID NO: 57), PAPAP (SEQ ID NO: 58).

According to specific embodiments, the linker is a GGGGSGGGGSGGGGS (SEQ ID NO: 59) linker.

According to a specific embodiment, the light chain and the heavy chain of the antibody (e.g. scFv) are linked via a linker, for example SEQ ID NO: 59.

According to specific embodiments, the linker comprises the extracellular Ig D3 domain of CD64 (e.g. SEQ ID NO: 60-61).

According to a specific embodiment, the antibody (e.g. scFv) is fused to the transmembrane domain of the polypeptide via a linker, for example SEQ ID NO: 60 or 61).

According to specific embodiments, the multi subunit protein module is produced by recombinant DNA technology.

Thus, according to an aspect of the present invention, there is provided at least one polynucleotide encoding the multi subunit protein module.

Hence, according to an aspect of the present invention, there is provided at least one polynucleotide encoding a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain capable of binding a target that is presented on a cell surface of a target cell of an immune cell, such that upon binding of said extracellular binding domain to said target said activating signal is transmitted in an immune cell expressing said multi subunit protein module.

According to an additional or an alternative aspect of the present invention, there is provided at least one polynucleotide encoding a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises a transmembrane domain of CD64 and an extracellular binding domain of CD64 capable of binding an Fc ligand; and wherein said polypeptides comprising said amino acid sequence of FcRγ and not comprising said binding domain comprise as a dimerizing moiety an amino acid sequence of a transmembrane domain of said FcRγ, such that upon binding of said extracellular binding domain to said Fc ligand said activating signal is transmitted in an immune cell expressing said multi subunit protein module.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above). This term includes polynucleotides derived from naturally occurring nucleic acids molecules (e.g., RNA or DNA), synthetic polynucleotide molecules composed of naturally occurring bases, sugars, and covalent internucleoside linkages (e.g., backbone), as well as synthetic polynucleotides and/or oligonucleotides having non-naturally occurring portions, which function similarly to the respective naturally occurring portions.

Such a modified polynucleotide may comprise modification in either backbone, internucleoside linkages or bases. Modified polynucleotides may be preferred over native forms according to specific embodiments, because of desirable properties such as, for example, enhanced cellular uptake, enhanced affinity for nucleic acid target and increased stability in the presence of nucleases.

According to specific embodiments, the polynucleotide is a modified polynucleotide e.g. modified RNA.

According to specific embodiments, the at least one polynucleotide comprises a nucleic acid sequence encoding a first polypeptide comprising an extracellular and a transmembrane domain of CD64 and an intracellular domain of FcRγ; and a nucleic acid sequence encoding a second distinct polypeptide comprising an extracellular, a transmembrane and an intracellular domain of FcRγ.

According to specific embodiments, the at least three cell membrane polypeptides described herein are encoded by a single polynucleotide. Further description on expression of multiple polypeptides from a single polynucleotide is provided hereinbelow.

Thus, according to specific embodiments, the at least one polynucleotide is one polynucleotide.

According to other specific embodiments, several polynucleotides are used to encode the polypeptides of the multi subunit protein module.

According to specific embodiments, the at least three cell membrane polypeptides described herein are encoded by different polynucleotides.

According to a specific embodiment, the at least one polypeptide comprising the extracellular binding domain disclosed herein is encoded by a first polynucleotide and the polypeptides not comprising the extracellular binding domain disclosed herein are encoded by a second polynucleotide.

Thus, according to specific embodiments, the at least one polynucleotide is at least two polynucleotides.

According so specific embodiments, the at least one polynucleotide is two polynucleotides.

To express any of the disclosed polypeptides in cells, a polynucleotide sequence encoding the polypeptide(s) is preferably ligated into a nucleic acid construct suitable for cell expression. Such a nucleic acid construct includes at least one cis-acting regulatory element for directing expression of the nucleic acid sequence. Cis-acting regulatory sequences include those that direct constitutive expression of a nucleotide sequence as well as those that direct inducible expression of the nucleotide sequence only under certain conditions. Thus, for example, a promoter sequence for directing transcription of the polynucleotide sequence in the cell in a constitutive or inducible manner is included in the nucleic acid construct. In the case of mRNA, since gene expression from an RNA source does not require transcription, there is no need in a promoter sequence or the additional sequences involved in transcription described hereinbelow.

The nucleic acid construct (also referred to herein as an "expression vector") of some embodiments of the invention includes additional sequences which render this vector suitable for replication and integration (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes or encodes a signal sequence for targeting the polypeptide to the cell surface. According to a specific embodiment, the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed, i.e. T cells. Examples of T cell specific promoters include lymphoid specific promoters [Calame et al., (1988) Adv. Immunol. 43:235-275]; in particular promoters of T-cell receptors [Winoto et al., (1989) EMBO J. 8:729-733].

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

A vector may also include a transcription terminator (e.g., from Bovine Growth Hormone (BGH) gene), an element allowing episomal replication and replication in prokaryotes (e.g. SV40 origin and ColEl or others known in the art) and/or elements to allow selection (e.g., ampicillin resistance gene and/or zeocin marker).

In order to assess the expression of a polypeptide or portions thereof, the expression vector can also contain either a selectable marker gene or a reporter gene or both to facilitate identification and selection of expressing cells from the population of cells sought to be transfected or transduced through viral vectors. Alternatively, the selectable marker may be carried on a separate polynucleotide and used in a co-transfection procedure. Both selectable markers and reporter genes may be flanked with appropriate regulatory sequences to enable expression in the host cells. Useful selectable markers include, for example, antibiotic-resistance genes, such as neo and the like. Reporter genes maybe be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the vector has been introduced into the host cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) or a self-cleavable peptide; and sequences for genomic integration of the promoter-chimeric polypeptide.

According to specific embodiments, the polypeptides of the multi subunit protein module described herein are expressed from distinct constructs.

According to other specific embodiments, the polypeptides of the multi subunit protein module described herein are expressed from a single construct in a multicistronic e.g. bicistronic manner. Such an expression can be achieved by method well known in the art such as, but not limited to, using internal ribosome entry site (IRES) sequence and/or a nucleic acid sequence encoding a self-cleavable peptide e.g. a 2A peptide (e.g. P2A, T2A, E2A).

Hence, according to specific embodiments, the polynucleotide or construct comprises a self-cleavable peptide (e.g. 2A skipping peptide, e.g. such as provided in SEQ ID NOs: 76-77).

According to specific embodiments, the polynucleotide or construct comprises an IRES sequence or a nucleic acid sequence encoding a self-cleavable peptide e.g. a 2A peptide between a nucleic acid sequence encoding a first polypeptide comprising an extracellular and a transmembrane domain of CD64 and an intracellular domain of FcRγ and a nucleic acid sequence encoding a second distinct polypeptide comprising an extracellular, a transmembrane and an intracellular domain of FcRγ.

A specific example of a polynucleotide encompassed by specific embodiments of the present invention comprises sequentially from 5' to 3' nucleic acid sequences encoding an extracellular domain of CD64, a transmembrane domain of CD64, an intracellular domain of FcRγ, a 2A skipping peptide, an extracellular domain of FcRγ, a transmembrane domain of FcRγ and an intracellular domain of FcRγ.

According to specific embodiments, the extracellular domain of CD64 the transmembrane domain of CD64 and the intracellular domain of FcRγ are translationally fused.

According to specific embodiments, the extracellular, transmembrane and intracellular domains of FcRγ are translationally fused.

Non-limiting examples of nucleic acid constructs encoding the multi subunit protein module of some embodiments of the invention are provided in SEQ ID NO: 4, 63 and 38.

It will be appreciated that the individual elements comprised in the expression vector can be arranged in a variety of configurations. For example, enhancer elements, promoters and the like, and even the polynucleotide sequence(s) encoding the polypeptide can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Various methods of producing embodiments of the present invention may be employed. For example, a vector can be directly transduced into a cell, e.g., an immune cell e.g. a T cell or a NK cell. According to specific embodiments, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. According to specific embodiments, the vector is capable of expressing the polynucleotide in mammalian e.g. human T cells. According to specific embodiments, the vector is capable of expressing the polynucleotide in mammalian e.g. human NK cell.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the host cell. The ability to select suitable vectors for transforming T cells is well within the capabilities of the ordinary skilled artisan and as such no general description of selection consideration is provided herein.

The terms "infecting" and "transducing", which are interchangeably used herein, refer to modification of cells through use of a viral vector.

Recombinant viral vectors are useful for expression of the polypeptides of some embodiments of the invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

The constructs described herein are suitable for introduction into cells of interest by various techniques. For example, an expression vector can be readily introduced into a host cell, e.g., mammalian, bacterial, yeast, or insect cell by any method in the art. For example, the expression vector can be transferred into a host cell by physical, chemical, or biological means. Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al, 2012, MOLECULAR CLONING: A LABORATORY MANUAL, volumes 1-4, Cold Spring Harbor Press, NY). An alternative method for the introduction of a polynucleotide into a host cell is lipofection, e.g., using Lipofectamine (Life Technologies). Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system. In the case where a non-viral delivery system is utilized, an exemplary delivery vehicle is a liposome. The use of lipid formulations is contemplated for the introduction of the nucleic acids into a host cell (in vitro, ex vivo or in vivo). According to additional or alternative embodiments, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et ah, 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Methods of the embodiments may concern transfecting the cells with a DNA encoding the multi subunit protein module described herein and, in some cases, a transposase. Such methods of transfecting of cells may also employ highly efficient transfections methods, such as electroporation. For example, nucleic acids may be introduced into cells using a nucleofection apparatus. If such methods are employed, the transfection step preferably does not involve infecting or transducing the cells with virus, which can cause genotoxicity and/or lead to an immune response to cells containing viral sequences in a treated subject. Such methods may involve transfecting cells with an expression vector encoding the multi subunit protein module. A wide range of constructs and expression vectors for the same are known in the art and are further detailed herein. For example, in some embodiments, the expression vector is a DNA expression vector such as a plasmid, linear expression vector or an episome. In some embodiments, the vector comprises additional sequences, such as sequence that facilitate expression of the polynucleotide, such a promoter, enhancer, poly-A signal, and/or one or more introns. In some embodiments, the coding sequence is flanked by transposon sequences, such that the presence of a transposase allows the coding sequence to integrate into the genome of the transfected cell.

Some methods may require that cells are further transfected with a transposase that facilitates integration of a coding sequence into the genome of the transfected cells. In some embodiments, the transposase is provided as DNA expression vector. In others, the transposase is provided as an expressible RNA or a protein such that long-term expression of the transposase does not occur in the transgenic cells. For example, the transposase may be provided as an mRNA (e.g., an mRNA comprising a cap and poly-A tail). Any transposase system may be used in accordance with the embodiments. However, in some aspects, the transposase is salmonid-type Tc1-like transposase (SB). For example, the transposase can be the so called "Sleeping beauty" transposase, see e.g., U.S. Pat. No. 6,489,458, incorporated herein by reference. In certain aspects, the transposase is an engineered enzyme with increased enzymatic activity. Some specific examples of transposases include, without limitation, SB10, SB11 or SB100× transposase (see, e.g., Mates et al., 2009, incorporated herein by reference). For example, a method can involve electroporation of cells with a mRNA encoding a SB10, SB11 or SB100× transposase.

Regardless of the method used to introduce exogenous nucleic acids into a host cell or otherwise expose a cell to embodiments of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Modification of cells to express the multi subunit protein modules may be performed with viral or non-viral constructs, such as adenovirus, lentivirus, Herpes simplex virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)].

Introduction of nucleic acids by viral infection offers several advantages over other methods such as lipofection and electroporation, since higher transduction efficiency can be obtained due to the infectious nature of viruses. For example, preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for targeting the polypeptide to the desired site in a cell. According to specific embodiments the signal sequence comprises a membrane trafficking sequence. Such sequences are known in the art. Non-limiting examples are provided in SEQ ID Nos: 72-73 and 74-75. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Specific embodiments of the present invention also contemplate immune cells expressing the multi subunit protein module described herein and method of generating same.

Thus, according to an aspect of the present invention, there is provided an immune cell genetically engineered to express the at least one polynucleotide.

According to an additional or an alternative aspect of the present invention, there is provided an immune cell expressing the at least one polynucleotide.

According to an additional or an alternative aspect of the present invention, there is provided an immune cell expressing at least one polynucleotide encoding a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain capable of binding a target that is presented on a cell surface of a target cell of an immune cell, such that upon binding of said extracellular binding domain to said target said activating signal is transmitted in the immune cell.

According to an additional or an alternative aspect of the present invention, there is provided an immune cell expressing at least one polynucleotide encoding a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises a transmembrane domain of CD64 and an extracellular binding domain of CD64 capable of binding an Fc ligand; and wherein said polypeptides comprising said amino acid sequence of FcRγ and not comprising said binding domain comprise as a dimerizing moiety an amino acid sequence of a transmembrane domain of said FcRγ, such that upon binding of said extracellular binding domain to said Fc ligand said activating signal is transmitted in the immune cell.

According to an additional or an alternative aspect of the present invention, there is provided an immune cell expressing the multi subunit protein module.

According to an additional or an alternative aspect of the present invention, there is provided an immune cell expressing a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain capable of binding a target that is presented on a cell surface of a target cell of an immune cell, such that upon binding of said extracellular binding domain to said target said activating signal is transmitted in the immune cell.

According to an additional or an alternative aspect of the present invention, there is provided an immune cell expressing a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises a transmembrane domain of CD64 and an extracellular binding domain of CD64 capable of binding an Fc ligand; and wherein said polypeptides comprising said amino acid sequence of FcRγ and not comprising said binding domain comprise as a dimerizing moiety an amino acid sequence of a transmembrane domain of said FcRγ, such that upon binding of said extracellular binding domain to said Fc ligand said activating signal is transmitted in the immune cell.

According to an additional or an alternative aspect of the present invention, there is provided a method of expressing a multi subunit protein module in an immune cell, the method comprising introducing into an immune cell the at least one polynucleotide, under conditions which allow expression of said multi subunit protein module.

Such conditions may be for example an appropriate temperature (e.g., 37° C.), atmosphere (e.g., air plus 5% $CO_2$), pH, light, medium, supplements and the like.

According to other specific embodiments, the introducing is effected in-vivo.

According to specific embodiments, the introducing is effected in-vitro or ex-vivo.

Methods of obtaining immune cells are well known in the art. Thus, for examples, PBMCs can be isolated by drawing whole blood from a subject and collection in a container containing an anti-coagulant (e.g. heparin or citrate); and apheresis. According to other specific embodiments, the immune cells are obtained from a tissue comprising cells associated with a pathology. Methods for obtaining a tissue sample from a subject are well known in the art and include e.g. biopsy, surgery or necropsy and preparing a single cell suspension thereof. Following, according to specific embodiments, at least one type of an immune cell is purified from the peripheral blood or from the single cell suspension. There are several methods and reagents known to those skilled in the art for purifying immune cells such as leukapheresis, sedimentation, density gradient centrifugation (e.g. ficoll), centrifugal elutriation, fractionation, chemical lysis of e.g. red blood cells (e.g. by ACK), selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cell is a human cell.

According to specific embodiments, the immune cell is of a healthy subject.

According to specific embodiments, the immune cell is of a subject suffering from a pathology (e.g. cancer).

Non-limiting examples of immune cells that can be used with specific embodiments of the invention include T cells, NK cells, NKT cells, B cells, macrophages, monocytes, dendritic cells (DCs) and granulocytes.

According to specific embodiments, the immune cell is selected from the group consisting of T cells, NK cells and NKT cells.

According to specific embodiments, the immune cell does not express an endogenous FcRγ, as determined by flow cytometry or western blot.

According to specific embodiments, the immune cell is a T cell.

According to an additional or an alternative aspect of the present invention, there is provided a T cell expressing a polypeptide complex, wherein the polypeptide complex comprises at least a first polypeptide and a second polypeptide, wherein said first and second polypeptides are not translationally fused, wherein the first polypeptide comprises an amino acid sequence of an Fc receptor common γ chain (FcRγ), said amino acid sequence is capable of transmitting an activating signal and forming a homodimer; and said second polypeptide comprising:
  (i) an extracellular ligand-binding domain of an Fcγ receptor (e.g. CD64) capable of binding an Fc ligand,
  (ii) an amino acid FcRγ capable of transmitting an activating signal and
  (iii) an amino acid sequence capable of recruiting said first polypeptide (e.g. the transmembrane domain of an Fc receptor), such that upon binding of said Fc ligand to said extracellular ligand-binding domain of said Fcγ receptor said activating signal is transmitted.

As used herein, the phrase "polypeptide complex" refers to a plurality of at least two distinct (i.e. not translationally fused) polypeptides which together have the activity of transmitting an activating signal in an immune cell expressing the polypeptide complex upon binding of the extracellular domain of the Fcγ receptor to its Fc ligand.

As used herein, the term "T cell" refers to a differentiated lymphocyte with a CD3+, T cell receptor (TCR)+ having either CD4+ or CD8+ phenotype.

According to specific embodiments, the T cell is an effector cell.

As used herein, the term "effector T cell" refers to a T cell that activates or directs other immune cells e.g. by producing cytokines or has a cytotoxic activity e.g., CD4+, Th1/Th2, CD8+ cytotoxic T lymphocyte.

According to specific embodiments, the T cell is a CD4+ T cell.

According to other specific embodiments, the T cell is a CD8+ T cell.

According to specific embodiments, the T cell is a αβ T cell.

According to specific embodiments, the T cell is a γδ T cell.

According to specific embodiments, the T cell is a naïve T cell.

According to specific embodiments, the T cell is a memory T cell. Non-limiting examples of memory T cells include effector memory CD4+ T cells with a CD3+/CD4+/CD45RA−/CCR7− phenotype, central memory CD4+ T cells with a CD3+/CD4+/CD45RA−/CCR7+ phenotype, effector memory CD8+ T cells with a CD3+/CD8+ CD45RA−/CCR7− phenotype and central memory CD8+ T cells with a CD3+/CD8+CD45RA−/CCR7+ phenotype.

According to specific embodiments, the T cell is a proliferating cell.

As used herein, the phrase "proliferating cell" refers to a T cell that proliferated upon stimulation as defined by a cell proliferation assay, such as, but not limited to, CFSE staining, MTS, Alamar blue, BRDU, thymidine incorporation, and the like.

According to specific embodiments, the T cell is a proliferating CD4+ T cell.

According to specific embodiments, the T cell is a proliferating CD8+ T cell.

According to specific embodiments, the T cell is expressing a T cell receptor specific for a pathologic (diseased, e.g. cancerous) cell, i.e. recognizes an antigen presented in the context of MHC which is overexpressed or only expressed by a pathologic cell as compared to a non-pathologic cell. Non-limiting examples of cancer antigens are further described hereinabove.

According to specific embodiments, the T cell is endogenously expressing a T cell receptor specific for a pathologic cell (e.g. cancerous cell).

According to specific embodiments, the T cell is an engineered T cells transduced with a T cell receptor (TCR).

As used herein the phrase "transduced with a TCR" or "genetically engineered to express a TCR" refers to cloning of variable α- and β-chains from T cells with specificity against a desired antigen presented in the context of MHC. Methods of transducing with a TCR are known in the art and are disclosed e.g. in Nicholson et al. Adv Hematol. 2012; 2012:404081; Wang and Rivière Cancer Gene Ther. 2015 March; 22(2):85-94); and Lamers et al, Cancer Gene Therapy (2002) 9, 613-623. According to specific embodiments, the TCR is specific for a pathologic cell.

According to specific embodiments, the T cell is an engineered T cells transduced with a chimeric antigen receptor (CAR).

As used herein, the phrase "transduced with a CAR" or "genetically engineered to express a CAR" refers to cloning of a nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. Method of transducing with a CAR are known in the art and are disclosed e.g. in Davila et al. Oncoimmunology. 2012 Dec. 1; 1(9):1577-1583; Wang and Rivière Cancer Gene Ther. 2015 March; 22(2):85-94); Maus et al. Blood. 2014 Apr. 24; 123(17):2625-35; Porter D L The New England journal of medicine. 2011, 365(8):725-733; Jackson H J, Nat Rev Clin Oncol. 2016; 13(6):370-383; and Globerson-Levin et al. Mol Ther. 2014; 22(5):1029-1038. According to specific embodiments, the antigen recognition moiety is specific for a pathologic cell.

According to other specific embodiments, the T cell is not transduced (i.e. does not express) a CAR.

According to specific embodiments, the immune cells comprise NK cells.

As used herein the term "NK cells" refers to differentiated lymphocytes with a CD16+ CD56+ and/or CD57+ TCR- phenotype. NK are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

According to specific embodiments, the immune cells comprise NKT cells.

As used herein the term "NKT cells" refers to a specialized population of T cells that express a semi-invariant αβ T-cell receptor, but also express a variety of molecular markers that are typically associated with NK cells, such as NK1.1. NKT cells include NK1.1+ and NK1.1-, as well as CD4+, CD4-, CD8+ and CD8- cells. The TCR on NKT cells is unique in that it recognizes glycolipid antigens presented by the MHC I-like molecule CD1d. NKT cells can have either protective or deleterious effects due to their abilities to produce cytokines that promote either inflammation or immune tolerance.

According to specific embodiments, the immune cells comprise B cells.

As used herein the term "B cells" refers to a lymphocyte with a B cell receptor (BCR)+, CD19+ and or B220+ phenotype. B cells are characterized by their ability to bind a specific antigen and elicit a humoral response.

According to specific embodiments, the immune cells comprise phagocytic cells.

As used herein, the term "phagocytic cells" refer to a cell that is capable of phagocytosis and include both professional and non-professional phagocytic cells. Methods of analyzing phagocytosis are well known in the art and include for examples killing assays, flow cytometry and/or microscopic evaluation (live cell imaging, fluorescence microscopy, confocal microscopy, electron microscopy). According to specific embodiments, the phagocytic cells are selected from the group consisting of monocytes, dendritic cells (DCs) and granulocytes.

According to specific embodiments, the immune cells comprise monocytes.

According to specific embodiments, the term "monocytes" refers to both circulating monocytes and to macrophages (also referred to as mononuclear phagocytes) present in a tissue.

According to specific embodiments, the monocytes comprise macrophages. Typically, cell surface phenotype of macrophages include CD14, CD40, CD11b, CD64, F4/80 (mice)/EMR1 (human), lysozyme M, MAC-1/MAC-3 and CD68.

According to specific embodiments, the monocytes comprise circulating monocytes. Typically, cell surface phenotypes of circulating monocytes include CD14 and CD16 (e.g. CD14++ CD16-, CD14+CD16++, CD14++CD16+).

According to specific embodiments, the immune cells comprise DCs.

As used herein the term "dendritic cells (DCs)" refers to any member of a diverse population of morphologically similar cell types found in lymphoid or non-lymphoid tissues. DCs are a class of professional antigen presenting cells, and have a high capacity for sensitizing HLA-restricted T cells. DCs include, for example, plasmacytoid dendritic cells, myeloid dendritic cells (including immature and mature dendritic cells), Langerhans cells, interdigitating cells, follicular dendritic cells. Dendritic cells may be recognized by function, or by phenotype, particularly by cell surface phenotype. These cells are characterized by their distinctive morphology having veil-like projections on the cell surface, intermediate to high levels of surface HLA-class II expression and ability to present antigen to T cells, particularly to naive T cells (See Steinman R, et al., Ann. Rev. Immunol. 1991; 9:271-196). Typically, cell surface phenotype of DCs include CD1a+, CD4+, CD86+, or HLA-DR. The term DCs encompasses both immature and mature DCs.

According to specific embodiments, the immune cells comprise granulocytes.

As used herein, the term "granulocytes" refer to polymorphonuclear leukocytes characterized by the presence of granules in their cytoplasm.

According to specific embodiments, the granulocytes comprise neutrophils.

According to specific embodiments, the granulocytes comprise mast-cells.

According to specific embodiments, the immune cells can be freshly isolated, stored e.g., cryopreserved (i.e. frozen) at e.g. liquid nitrogen temperature at any stage for long periods of time (e.g., months, years) for future use; and cell lines.

Methods of cryopreservation are commonly known by one of ordinary skill in the art and are disclosed e.g. in International Patent Application Publication Nos. WO2007054160 and WO 2001039594 and US Patent Application Publication No. US20120149108.

According to specific embodiments, the immune cells can be stored in a cell bank or a depository or storage facility.

Consequently, specific embodiments of the present teachings further suggest the use of the immune cells (e.g. T cells) and the methods disclosed herein as, but not limited to, a source for adoptive immune cells therapies for diseases that can benefit from activating immune cells against pathologic cells e.g. a hyper-proliferative disease; a disease associated with immune suppression and infections.

Thus, according to an aspect of the present invention, the immune cells disclosed herein are for use in adoptive cell therapy.

The immune cells used according to specific embodiments of the present invention may be autologous or non-autologous; they can be syngeneic or non-syngeneic: allogeneic or xenogeneic to the subject; each possibility represents a separate embodiment of the present invention.

According to specific embodiments, the cells are autologous to said subject.

According to specific embodiments, the cells are non-autologous to said subject.

According to specific embodiments, the immune cells described herein are cultured, expanded and/or activated ex-vivo prior to administration to the subject.

Methods of culturing, expanding and activating immune cells are well known to the skilled in the art. For example, T cells may be activated ex vivo in the presence of one or more molecule such as, but not limited to, an anti-CD3 antibody, an anti-CD28 antibody, anti-CD3 and anti-CD28 coated beads (such as the CD3CD28 MACSiBeads obtained from Miltenyi Biotec), IL-2, phytohemagglutinin, an antigen-loaded antigen presenting cell [APC, e.g. dendritic cell], a peptide loaded recombinant MHC.

Since the immune cells of specific embodiments of the present invention are activated upon binding of the extracellular binding domain to a target presented on a cell surface of a target cell of an immune cell, they may be used for, but not limited to, treating diseases associated with pathologic cells presenting the target on their cell surface.

Thus, according to an aspect of the present invention, there is provided a method of treating a disease associated with a pathologic cell in a subject in need thereof, the method comprising administering to the subject a therapeutically effective amount of the immune cell disclosed herein, wherein said pathologic cell presents said target on its cell surface, thereby treating the disease in the subject.

According to an additional or an alternative aspect of the present invention, there is provided the immune cell disclosed herein, for use in treating a disease associated with a pathologic cell in a subject in need thereof, wherein said pathologic cell presents said target on its cell surface.

According to an additional or an alternative aspect of the present invention, there is provided a method of treating a disease associated with a pathologic cell in a subject in need thereof, the method comprising administering to the subject a therapeutically effective amount of T cells expressing a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain capable of binding a target that is presented on a cell surface said pathologic cell, such that upon binding of said extracellular binding domain to said target said activating signal is transmitted in the T cells, thereby treating the disease in the subject.

According to an additional or an alternative aspect of the present invention, there is provided a therapeutically effective amount of T cells expressing a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain capable of binding a target that is presented on a cell surface a pathologic cell, such that upon binding of said extracellular binding domain to said target said activating signal is transmitted in the T cells, for use in treating a disease associated with said pathologic cell in a subject in need thereof.

Since the immune cells of specific embodiments of the present invention are activated upon binding of the extracellular binding domain to a target bound to a cell surface of a pathologic cell, they may be used for, but not limited to, treating diseases associated with pathologic cells in combination with a therapeutic composition comprising the target which is directed for binding the pathologic cells, i.e. binds an antigen overexpressed or only expressed by a pathologic (e.g. cancerous) cell as compared to a non-pathologic cell. For examples, when the extracellular binding domain is of CD64 and the target is an Fc ligand; the therapeutic composition comprises an Fc domain (e.g. antibody) which is directed for binding an antigen overexpressed or only expressed by the pathologic cells.

Thus, according to specific embodiments, the subject is treated with a therapeutic composition comprising said target, said therapeutic composition being specific for said pathologic cell.

According to specific embodiments, the therapeutic composition comprising the Fc domain is specific for a pathologic cell.

According to specific embodiments, the method comprises administering to said subject a therapeutically effective amount of a therapeutic composition comprising said target, said therapeutic composition being specific for said pathologic cell.

According to an additional or an alternative aspect of the present invention, there is provided a method of treating a disease associated with a pathologic cell in a subject in need thereof, the method comprising administering to the subject a therapeutically effective amount of the immune cell disclosed herein, and a therapeutic composition comprising said target, said therapeutic composition being specific for said pathologic cell, thereby treating the disease in the subject.

According to an additional or an alternative aspect of the present invention, there is provided the immune cell disclosed herein and a therapeutic composition comprising said target, for use in treating a disease associated with a pathologic cell in a subject in need thereof, wherein said therapeutic composition being specific for said pathologic cell.

As used herein, the term "subject" or "subject in need thereof" includes mammals, preferably human beings at any age or gender. The subject may be healthy or showing preliminary signs of a pathology, e.g. cancer. This term also encompasses individuals who are at risk to develop the pathology.

As used herein the term "treating" refers to curing, reversing, attenuating, alleviating, minimizing, suppressing or halting the deleterious effects of a disease or disorder (e.g. cancer). Those of skill in the art will understand that various methodologies and assays can be used to assess the development of a pathology, and similarly, various methodologies and assays may be used to assess the reduction, remission or regression of a pathology (e.g. a malignancy), as discussed below.

As used herein, the term "preventing" refers to keeping a disease, disorder or condition from occurring in a subject who may be at risk for the disease, but has not yet been diagnosed as having the disease.

As used herein the phrase, "disease associated with a pathologic cell" means that pathologic cells drive onset and/or progression of the disease.

According to specific embodiments, the disease can benefit from activating the immune cells of the subject.

As used herein the phrase "a disease that can benefit from activating immune cells" refers to diseases in which the subject's immune response activity may be sufficient to at least ameliorate symptoms of the disease or delay onset of symptoms, however for any reason the activity of the subject's immune response in doing so is less than optimal.

Non-limiting examples of diseases treated by some embodiments of the invention include hyper-proliferative diseases, diseases associated with immune suppression, immunosuppression caused by medication (e.g. mTOR inhibitors, calcineurin inhibitor, steroids) and infections.

According to specific embodiments, the disease comprises an infection.

As used herein, the term "infection" or "infectious disease" refers to a disease induced by a pathogen. Specific examples of pathogens include, viral pathogens, bacterial pathogens e.g., intracellular mycobacterial pathogens (such as, for example, *Mycobacterium tuberculosis*), intracellular bacterial pathogens (such as, for example, *Listeria monocytogenes*), or intracellular protozoan pathogens (such as, for example, *Leishmania* and *Trypanosoma*).

Specific types of viral pathogens causing infectious diseases include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to specific embodiments of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

According to specific embodiments, the disease comprises a hyper-proliferative disease.

According to specific embodiments, the hyper-proliferative disease comprises sclerosis, fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to other specific embodiments, the hyper-proliferative disease comprises cancer.

Thus, according to specific embodiments the pathologic cell is a cancerous cell.

Cancers which may be treated by some embodiments of the invention can be any solid or non-solid tumor (including liquid cancer), cancer metastasis and/or a pre-cancer.

According to specific embodiments, the cancer is a malignant cancer.

Examples of cancer include but are not limited to, carcinoma, blastoma, sarcoma and lymphoma. More particular examples of such cancers include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to specific embodiments, the cancer is a pre-malignant cancer.

Pre-cancers are well characterized and known in the art (refer, for example, to Berman J J. and Henson D E., 2003. Classifying the pre-cancers: a metadata approach. BMC Med Inform Decis Mak. 3:8). Examples of pre-cancers include, but are not limited to, acquired small pre-cancers, acquired large lesions with nuclear atypia, precursor lesions occurring with inherited hyperplastic syndromes that progress to cancer, and acquired diffuse hyperplasias and diffuse metaplasias. Non-limiting examples of small pre-cancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia).

Non-limiting examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Non-limiting examples of precursor lesions occurring with inherited hyperplastic syndromes that progress to cancer include atypical mole syndrome, C cell adenomatosis and MEA. Non-limiting examples of acquired diffuse hyperplasias and diffuse metaplasias include Paget's disease of bone and ulcerative colitis.

Examples of solid tumors that can be treated by the instant methods include tumors and/or metastasis (wherever located) other than lymphatic cancer, for example brain and other central nervous system tumors (including but not limited to tumors of the meninges, brain, spinal cord, cranial nerves and other parts of central nervous system, e.g. glioblastomas or medulla blastomas); head and/or neck cancer; breast tumors; circulatory system tumors (including but not limited to heart, mediastinum and pleura, and other intrathoracic organs, vascular tumors and tumor-associated vascular tissue); excretory system tumors (including but not limited to tumors of kidney, renal pelvis, ureter, bladder, other and unspecified urinary organs); gastrointestinal tract tumors (including but not limited to tumors of oesophagus, stomach, small intestine, colon, colorectal, rectosigmoid junction, rectum, anus and anal canal, tumors involving the liver and intrahepatic bile ducts, gall bladder, other and unspecified parts of biliary tract, pancreas, other and digestive organs); oral cavity tumors (including but not limited to tumors of lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (including but not limited to tumors of vulva, vagina, Cervix uteri, Corpus uteri, uterus, ovary, and other sites associated with female genital organs, placenta, penis, prostate, testis, and other sites associated with male genital organs); respiratory tract tumors (including but not limited to tumors of nasal cavity and middle ear, accessory sinuses, larynx, trachea, bronchus and lung, e.g. small cell lung cancer or non-small cell lung cancer); skeletal system tumors (including but not limited to tumors of bone and articular cartilage of limbs, bone articular cartilage and other sites); skin tumors (including but not limited to malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites.

In some examples, the solid tumor treated by the methods of the instant disclosure is pancreatic cancer, bladder cancer, colon cancer, liver cancer, colorectal cancer (colon cancer or rectal cancer), breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors, bone cancer, skin cancer, ocular tumor, choriocarcinoma (tumor of the placenta), sarcoma or soft tissue cancer.

In some examples, the solid tumor to be treated by the methods of the instant disclosure is selected bladder cancer, bone cancer, breast cancer, cervical cancer, CNS cancer, colon cancer, ocular tumor, renal cancer, liver cancer, lung cancer, pancreatic cancer, choriocarcinoma (tumor of the placenta), prostate cancer, sarcoma, skin cancer, soft tissue cancer or gastric cancer.

In some examples, the solid tumor treated by the methods of the instant disclosure is breast cancer. Non limiting examples of breast cancer that can be treated by the instant methods include ductal carcinoma in situ (DCIS or intraductal carcinoma), lobular carcinoma in situ (LCIS), invasive (or infiltrating) ductal carcinoma, invasive (or infiltrating) lobular carcinoma, inflammatory breast cancer, triple-negative breast cancer, paget disease of the nipple, phyllodes tumor (phylloides tumor or cystosarcoma phyllodes), angiosarcoma, adenoid cystic (or adenocystic) carcinoma, low-grade adenosquamous carcinoma, medullary carcinoma, papillary carcinoma, tubular carcinoma, metaplastic carcinoma, micropapillary carcinoma, and mixed carcinoma.

In some examples, the solid tumor treated by the methods of the instant disclosure is bone cancer. Non limiting examples of bone cancer that can be treated by the instant methods include osteosarcoma, chondrosarcoma, the Ewing Sarcoma Family of Tumors (ESFTs).

In some examples, the solid tumor treated by the methods of the instant disclosure is skin cancer. Non limiting examples of skin cancer that can be treated by the instant methods include melanoma, basal cell skin cancer, and squamous cell skin cancer.

In some examples, the solid tumor treated by the methods of the instant disclosure is ocular tumor. Non limiting examples of ocular tumor that can be treated by the methods of the instant disclosure include ocular tumor is choroidal nevus, choroidal melanoma, choroidal metastasis, choroidal hemangioma, choroidal osteoma, iris melanoma, uveal melanoma, intraocular lymphoma, melanocytoma, metastasis retinal capillary hemangiomas, congenital hypertrophy of the RPE, RPE adenoma or retinoblastoma. In some embodiments, cancers that are treated are liquid cancers. Examples of liquid cancers that can be treated by the methods provided herein include, but are not limited to, leukemias, myelomas, and liquid lymphomas. In specific embodiments, liquid cancers that can be treated in accordance with the methods described include, but are not limited to, liquid lymphomas, leukemias, and myelomas. Exemplary liquid lymphomas and leukemias that can be treated in accordance with the methods described include, but are not limited to, acute myelogenous leukemia (AML), myelodysplastic syndromes (MDS), chronic lymphocytic leukemia/small lymphocytic lymphoma, B-cell prolymphocytic leukemia, lymphoplasmacytic lymphoma (such as waldenström macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical Hodgkin lymphomas (nodular sclerosis, mixed cellularity, lymphocyte-rich, lymphocyte depleted or not depleted), and nodular lymphocyte-predominant Hodgkin lymphoma. In one aspect, myelodysplastic syndromes (MDS) is a heterogenous group of clonal, hematopoietic stem cell disorders characterized by distinct morphological bone marrow changes, abnormal blood counts, common cytogenetic abnormalities, and recurrent mutations. MDS can predominantly occur in the elderly. Treatment of MDS can be based on risk stratification, with the International Prognostic Scoring System (IPSS) or revised IPSS (IPSS-R) being the most common classification systems. Low-risk MDS patients can receive supportive care or hematopoietic growth factors. A subset of patients with 5q deletions can be treated with lenalidomide. High-risk patients can be treated with hypomethylating agents (e.g., azacitidine, decitabine), intensive chemotherapy, and/or allogeneic stem cell transplantation. In some cases, MDS patients can be transformed to AML. Some MDS patients can develop progressive bone marrow failure and/or die of complications related to neutropenia (e.g., infection) or thrombocytopenia (e.g., bleeding). Initial management of MDS can be based on risk stratification. The newer IPSS-R can place patients into 5 categories: very good, good, intermediate, high, and very-high risk groups. Patients in the very good, good, and select intermediate-risk patients can be categorized as "low-risk," whereas high, very high, and certain intermediate-risk patients can be categorized as the "high-risk" group. Azacitidine (5'-azacytidine) and decitabine (5'-aza-2'-deoxycytidine), which both are cytosine analogues, can lead to inhibition of DNA-methyltransferases (DNMTs) and can act as hypomethylating agents.

In another aspect, acute myeloid leukemia (AML) is characterized by the proliferation and accumulation of myeloid cells with accompanying hematopoietic failure. AML can be caused by chemical exposure, prior chemotherapy and radiation, or other environmental toxins.

According to specific embodiments, the cancer is selected from the group consisting of melanoma, lymphoma, colon cancer, lung cancer, breast cancer and pancreatic cancer.

According to specific embodiments, the cancer is melanoma or lymphoma.

According to specific embodiments, the cancer or the cancerous cell expresses a marker selected from the group consisting of PDL-1, E-Cadherin, CD19, MUC1, TRP-1 and TRP-2.

According to specific embodiments, the cancer or the cancerous cell expresses PDL-1.

As mentioned, according to specific embodiments, the immune cells are administered to the subject in combination with a therapeutic composition comprising the target.

Thus, for examples, when the target is an Fc ligand, the therapeutic composition comprises an Fc domain. Therapeutic compositions comprising Fc domains specific for pathologic cells are well known in the art and include, but not limited to, Fc-fusion proteins and antibodies.

According to specific embodiments, the Fc domain is of an IgG antibody.

According to specific embodiments, the therapeutic composition is an Fc-fusion protein.

As used herein the term, "Fc-fusion protein" refers to a molecule comprising an amino acid sequence capable of binding a pathologic cell (i.e. an antigen overexpressed or only expressed on a pathologic cell) combined with an Fc domain of an antibody.

Selection of the Fc-fusion protein used is well within the capability of those skilled in the art, and depends on the type of the disease and the antigens expressed by the pathologic cells associated with the pathology.

Non-limiting examples of Fc-fusion proteins that can be used with specific embodiments are disclosed in Weidle et al. Cancer Genomics and Proteomics (2012) 9(6): 357-372; and Sioud et al. Molecular Therapy—Methods & Clinical Development (2015) 2, 15043, the contents of which is fully incorporated herein by reference.

According to specific embodiments, the therapeutic composition is an antibody.

Selection of the therapeutic antibody used is well within the capability of those skilled in the art, and depends on the type of the disease and the antigens expressed by the pathologic cells associated with the pathology.

According to specific embodiments, the therapeutic antibody binds an antigen overexpressed or only expressed by tumor cells. Non-limiting examples of tumor antigens are further described hereinabove.

According to specific embodiments, the antibody is an IgG antibody (e.g. IgG1, IgG2, IgG3, IgG4).

According to a specific embodiment the antibody isotype is IgG1 or IgG3.

According to specific embodiments, the therapeutic antibody is an anti-TRP-1 or an anti-CD44 antibody.

According to some embodiments of the invention, the therapeutic antibody is selected from the group consisting of Atezolizumab, Avelumab, Alemtuzumab, Cetuximab, Panitumumab, Nimotuzumab, Rituximab, Gatipotuzumab (previously known as PankoMab-GEX®), Trastuzumab, Alemtuzumab, Bevacizumab, Ofatumumab, Pertuzumab, ofatumumab, obinutuzumab and IVIG.

According to specific embodiments, the therapeutic antibody is selected from the group consisting of Atezolizumab, Rituximab, Cetuximab, Gatipotuzumab and IVIG.

According to specific embodiments, the therapeutic antibody is an anti-PDL-1.

According to specific embodiments, the cancerous cell expresses PDL-1 and the therapeutic antibody is an anti-PDL-1.

According to specific embodiments, the antibody is Atezolizumab.

According to an aspect of the present invention, there is provided a method of treating a disease associated with a pathologic cell in a subject in need thereof, the method comprising administering to the subject a therapeutically effective amount of:
(i) an antibody specific for said pathologic cell; and
(ii) T cells expressing a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain of CD64 capable of binding an Fc ligand, such that upon binding of said extracellular binding domain to said Fc ligand said activating signal is transmitted in said T cell, thereby treating the disease in the subject.

According to an additional or an alternative aspect of the present invention, there is provided a therapeutically effective amount of:
(i) an antibody specific for a pathologic cell; and
(ii) T cells expressing a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain of CD64 capable of binding an Fc ligand, such that upon binding of said extracellular binding domain to said Fc ligand said activating signal is transmitted in said T cell, for use in treating a disease associated with said pathologic cell in a subject in need thereof.

According to an additional or an alternative aspect of the present invention, there is provided a method of increasing the killing capacity of an antibody against a pathologic cell in a subject in need thereof, the method comprising administering to the subject a therapeutically effective amount of:
(i) an antibody specific for the pathologic cell; and
(ii) T cells expressing a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain of CD64 capable of binding an Fc ligand, such that upon binding of said extracellular binding domain to said Fc ligand said activating signal is transmitted in said T cell, thereby increasing the killing capacity of the antibody against the pathologic cell.

The administration of the immune cells and the administration of the therapeutic composition can be effected in the same route or in separate routes.

The administration of the immune cells may be following or concomitant with the therapeutic composition comprising the target.

According to specific embodiments, the immune cells disclosed herein are administered to the subject following treatment with the therapeutic composition comprising the target.

According to other specific embodiments, the immune cells disclosed herein are administered to the subject concomitantly with the therapeutic composition comprising the target.

Multiple rounds of administration of the immune cells and multiple doses of the therapeutic composition comprising the target can be administered. Thus, according to specific embodiments, administering the immune cells disclosed herein is effected following at least one administration of the therapeutic composition comprising the target. According to specific embodiments, administering the cells disclosed herein is effected in a sequential order with the treatment with the therapeutic composition comprising the target.

According to specific embodiments, the multi subunit protein module is more efficient (e.g. at least 1.5 fold, at least 2 fold, at least 3 fold, at least 4 fold) in activating an immune cell (e.g. T cell) expressing the module following binding to the target as compared to an immune cell of the same type expressing only a single polypeptide comprising the extracellular binding domain capable of binding the target and the amino acid sequence of FcRγ capable of transmitting the activating signal; or a peptide complex comprising a first polypeptide comprising the amino acid sequence of FcRγ capable of transmitting the activating signal; and a second polypeptide comprising the extracellular binding domain capable of binding the target which is devoid of the amino acid sequence of FcRγ capable of transmitting the activating signal.

According to specific embodiments, this increase in efficiency may be manifested by reduced ratio of effector immune cells:target cells (e.g. less than 4:1, less than 5:1, less than 6:1, less than 7:1, less than 8:1).

According to specific embodiments, this increase in efficiency may be manifested by reduced number of immune cells infused to the subject.

According to specific embodiments, the immune cells and the therapeutic compositions comprising the target disclosed herein can be administered to a subject in combination with other established or experimental therapeutic regimen to treat a disease associated with pathologic cells (e.g. cancer) including, but not limited to analgesics, chemotherapeutic agents, radiotherapeutic agents, cytotoxic therapies (conditioning), hormonal therapy and other treatment regimens (e.g., surgery) which are well known in the art.

According to specific embodiments, the method of treatment involves first using pre-conditioning for cell therapy. Thus, the method of some embodiments comprises administering a pre-conditioning agent prior to administering the immune cells (e.g. T cells). For example, pre-conditioning patients prior to T cell therapies typically improves the efficacy of the T cell therapy by reducing the number of endogenous lymphocytes and increasing the serum level of homeostatic cytokines and/or pro-immune factors present in the patient. This creates a more optimal microenvironment for the transplanted T cells to proliferate once administered to the patient, and reduces the number of endogenous lymphocytes. Non-limiting examples of pre-conditioning agents include cyclophosphamide and/or fludarabine.

The immune cells disclosed herein and/or the therapeutic compositions disclosed herein can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the immune cells and/or the therapeutic composition accountable for the biological effect.

According to specific embodiments, the immune cells are the active ingredient in the formulation.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, intradermal, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

According to a specific embodiment, the immune cells disclosed herein or the pharmaceutical composition comprising same is administered via an IV route.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Alternative embodiments include depots providing sustained release or prolonged duration of activity of the active ingredient in the subject, as are well known in the art.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to another aspect of the present invention there is provided an article of manufacture comprising a packaging material packaging the immune cells disclosed herein and a therapeutic composition comprising said target.

According to specific embodiments, the therapeutic composition is specific for a pathologic cell.

According to specific embodiments, the immune cell is a T cell and the therapeutic composition is an antibody.

According to an aspect of the present invention there is provided an article of manufacture comprising a packaging material packaging an antibody and T cells expressing a multi subunit protein module comprising at least three cell membrane polypeptides each comprising an amino acid sequence of an Fc receptor common γ chain (FcRγ), said amino acid sequence is capable of transmitting an activating signal; wherein at least one but not all of said at least three polypeptides comprises an extracellular binding domain of an Fcγ receptor (e.g. CD64) capable of binding an Fc ligand, such that upon binding of said extracellular binding domain to said Fc ligand said activating signal is transmitted in said T cell. According to specific embodiments, the article of manufacture is identified for the treatment of a disease associated with a pathologic cell (e.g. cancer).

According to specific embodiments, the immune cells (e.g. T cell) disclosed herein; and the therapeutic composition comprising the target (e.g. antibody) are packaged in separate containers.

According to specific embodiments, the immune cells (e.g. T cell) disclosed herein; and the therapeutic composition comprising the target (e.g. antibody) are packaged in a co-formulation.

According to specific embodiments, the article of manufacture further comprises a pre-conditioning agent. Further description and non-limiting exemplary agents are further provide hereinabove.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

Each patent, publication, and non-patent literature cited in the application is hereby incorporated by reference in its entirety as if each was incorporated by reference individually.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H.

Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Mice—Wild-type (WT) C57BL/6 mice or BALB/c mice were obtained from Envigo (Jerusalem, Israel), and from Jackson Laboratories (Bar-Harbor, ME, USA). All mice were housed in an American Association for the Accreditation of Laboratory Animal Care-accredited animal facility and maintained in specific pathogen-free conditions. Male and female 8-12 weeks old mice were used in all experiments. All animal experiments were approved by the Tel-Aviv University or the Stanford University Institutional Animal Care and Use Committees.

Cell lines—B16F10 cells (CRL-6475, ATCC), YUMM1.7 (CRL-3362, ATCC), HEK-293FT (Thermo Fisher Scientific, Waltham, MA), A20 cells (Nahmad et al. bioRxiv 2020.02.28.970822; doi: wwwdoi(dot)org/10.1101/2020.02.28.970822) Jurkat cells (Aqaue et al. Cancer Res. 2019 Aug. 1; 79(15):3862-3876)), 293GP (Burns J C et al. PNAS USA. 1993 Sep. 1; 90(17):8033-7) and HT-29 (human colon adenocarcinoma, HTB-38, ATCC), were cultured in DMEM (GIBCO) supplemented with 10% heat-inactivated FBS (Biological Industries, Israel), 2 mM L-glutamine, and 100 µg/mL penicillin/streptomycin (GIBCO) under standard conditions. Cells were routinely tested for *Mycoplasma* using EZ-PCR *Mycoplasma* Test Kit (Biological Industries, Israel) according to manufacturer's instructions. B16F10 and YUMM1.7 cells were infected by lentivirus containing pLVX-H2B-tdTomato, and were sorted by FACS (BD FACSAria™ III, BD Biosciences, Franklin Lakes, NJ) for the high-expressing tdTomato population. NK-92 cells (CRL-2407, ATCC) were cultured in RPMI supplemented with 200 U of human IL-2 (Peprotech).

Lentiviral infection—HEK-293FT cells were transfected with pLVX plasmids containing H2B-tdTomato under EF1 promoter together with psPAX2 (Addgene plasmid #12260) and pCMV-VSV-G (Addgene plasmid #8454). Media-containing viruses were collected following 24 and 48 hours. For infection, B16F10 or HT-29 cells were incubated with viruses and 100 µg/mL polybrene (Sigma Aldrich, Merck, Israel) for 30 minutes followed by 30 minutes centrifugation before medium was replaced. Following three days, cells that expressed tdTomato were sorted by FACSAriaII.

Constructs design—Several constructs were generated to express FcγRI and FcRγ (see FIGS. 1A, 1B and 8A), SEQ ID Nos: 1-8). Specifically, inserts of the fusion sequences were synthesized by GeneART (Thermo Fisher Scientific) into pMK vectors and were further cloned into pMIGII using EcoRI/XhoI sites upstream to IRES-GFP sequences or into pMSVG.1 vector cut with NcoI/NotI. Clones were verified by pBABE5' and IRES-Rev primers sequencing (HyLabs Israel). Histone H2B sequence was amplified with AATAACACTAGTGCCACCATGCCT-GAACCGGCAAAAT (SEQ ID NO: 9) and AACAACCCCGGGACTTGTCGTCATCGTCTTTGT (SEQ ID NO: 10) primers and cloned into pLVX vector (Clontech) containing EF1 promoter into SpeI/XmaI sites in frame with tdTomato. Sequence was verified by MSC\v forward and tdTomato reverse primers (HyLabs Israel). Extracellular and transmembrane and 7 residues of intracellular region of human HER2 or EGFR were cloned into pLVX vector using SpeI/NotI or EoRI/NotI respectively) sites.

Retroviral infection—Mouse total $CD3^+$ T cells or specific $CD4^+$ or $CD8^+$ T cells were isolated from mouse blood and infected with the above constructs as follows: Platinum E cells were plated on 10 cm culture plates and co-transfected with 2:1 molar ratio of $pMIGII^{45}$ and PCL-Eco plasmids using Polyplus jetPRIME® reagent (Polyplus transfections). Following 24 hours, media was replaced with complete DMEM supplemented with 0.075% Sodium Bicarbonate. Media-containing viruses were collected after 24 hours and 48 hours and centrifuged for 1 hour at 100,000 g. Pellet was resuspended gently in 1 mL media and let to recover overnight at 4° C. Prior to infection, splenic $CD4^+$ T cells or splenic $CD8^+$ T cells were incubated on plate pre-coated with anti-CD3 (0.5 µg/mL) in T cell media containing high-dose IL-2 (1,000 IU/ml). Next, 0.3 mL of concentrated retroviruses were added to every $2\times10^6$ $CD4^+$ or $CD8^+$ T cells with 10 µg/mL polybrene. Cells were incubated for 30 minutes in 37° C., 5% $CO_2$ and centrifuged at 37° C. 1,200 rpm for 1 hour. Following, 80% of medium was replaced and T cells were cultured for additional three days in T cell media containing high-dose IL-2. For infection of human cells (PBMC, NK-92 or γδ-T cells), $1.2\times10^6$ 293GP cells were cultured in PLL-coated 6 well plate, transfected using JetOptimus (Polyplus transfections) with 1.4 µg RD114 envelope plasmid and 2 µg pMIGII or pMSVG.1 plasmid. 48 hours later, supernatants were collected, filtered with 0.45 µM PVDF filter, and $1.5\times10^5$ cells were infected in 24 well suspension plate coated with Retronectin (Takara).

Primary human cells—Human PBMCs were collected from healthy donor, separated using Ficoll Histopaque-1077 HYBRI-MAX (Sigma aldrich), activated for 48 hours with Ultra-LEAF™ Purified anti-human CD3 Antibody (OKT3, Biolegend), together with 1000 U IL-2 (Peprotech), followed by retrovirus infection. For γδ T cells, human PBMCs from healthy donor were collected and cultured for 8 days with Zoledronate (5 uM, Novartis) and IL-2 (500 U, Peprotech), separated using EasySep™ Human Gamma/Delta T Cell Isolation Kit (StemCell technologies), and transduced with a retrovirus vector as described.

Confocal microscopy—Infected $CD3^+$ or $CD4^+$ and $CD8^+$ T cells were plated on glass-bottom confocal plates and stained using anti-CD3 (clone 17A2, BioLegend), anti-TCRβ (H57-597), anti-FcRI (X54-5/7.1, BioLegend). A20 cells were stained using anti-B220 antibody (RA-3-6B2, BioLegend). Human primary cells were stained with anti-human CD3 (HIT3a, BioLegend), Alexa Fluor® 647 anti-human TCR γ/δ (B1, BioLegend) APC-anti-human CD64 (10.1, BioLegend) APC anti-human CD56 (5.1H11, BioLegend). HT-29 were stained with Alexa Fluor® 488 anti-human CD340 (erbB2/HER-2, 24D2, BioLegend), Alexa Fluor® 488 anti-human EGFR Antibody (AY13, BioLegend). Images were collected using a Zeiss LSM800 confocal laser scanning microscope and analyzed using ZEN software (Carl Zeiss Microscopy).

Killing assay—IncuCyte imager killing assays were conducted by culturing $10^4$ H2B-tdTomato B16F10 or YUMM1.7-H2B target cells in 96 wells plate with uninfected or infected CD4$^+$ or CD8+ T cells at several effector:target ratios. Following 2 hours, where indicated, cells were added with 15 μg anti-TRP-1 (TA99, BioXcell) or anti-CD44 (IM7, BioLegend) antibodies in 200 μl medium. For human cells killing assays, $10^4$ HT-29 were cultured in 96 well plate; 24 hours later human effector cells were added in the specified ratios, with or without 60 μg/ml Trastuzumab (HY-P9907, MedChemExpress) or Cetuximab (HY-P9905, MedChemExpress). Cells were imaged by incuCyte S3 imager (Sartorius) for 24-60 hours. Images were then used to calculate numbers of target cells by incuCyte software. Human T cells activity was also evaluated by measuring the TNFα cytokine levels using Human TNF-alpha DuoSet ELISA (DY210, R&D Systems) and IFNγ levels using Human IFN-gamma DuoSet ELISA (DY285, R&D Systems). A20 killing was evaluated following 24 hours co-culture of A20 cells in a u-shaped 96 wells plate with infected CD8+ T cells isolated from BALB/c splenocytes, with or without 10 μg anti-CD20 antibody (18B12, Absolute antibody). Killing of A20 cells was determined by APC-Annexin V staining kit (BioLegend) in flow cytometer.

Flow cytometry—Purified T cells were analyzed using flow cytometry (CytoFLEX, Beckman Coulter, Lakeview Indianapolis, IA) for expressed GFP or by staining with Alexa Fluor® 647 anti-mouse CD64 (FcγRI) Antibody (X54-5/7.1, BioLegend), Brilliant Violet 421 or APC anti-human CD64 Antibody (10.1, BioLegend), Alexa Fluor® 488-anti-human CD3 (HIT3a, BioLegend). A20 cells were stained by PE-anti CD45R/B220 antibody (RA-3-6B2, BioLegend). Datasets were analyzed using FlowJo software (Tree Star).

In vivo tumor models—$2\times10^5$ B16F10 cells suspended in 50 μL DMEM were injected sub-cutaneously (s.c.) to C57BL/6 mice above the right flank and the size of growing tumors was measured twice a week using calipers. When tumors reached 120 mm$^2$, mice were sacrificed for ethical considerations. Animal were injected intravenously (i.v.) with $2\times10^6$ uninfected (sham) or retroviral infected with pMIGII-alpha-gamma-2A-Gamma (SEQ ID NO: 4) CD3+ T cells, with or without 300 μg anti-TRP1 antibody (clone TA99) s.c. Treatment was applied at days 7, 11 and 14 post tumor injection.

Statistical analyses—Each experiment was performed three times. Each experimental group consisted of at least three mice. Significance of results was determined using the nonparametric one-way ANOVA, when multiple groups are analyzed, or nonparametric Student's t-test.

Example 1

Exogenous Expression of FcRγ and FcγRI Fused to the Intracellular Domain of FcRγ in CD4+ and CD8+ T Cells Induces Effective Tumor Cell Lysis The following constructs were cloned: the extracellular, transmembrane and intracellular domains of FcγRI, T2A skipping peptide and FcRγ (SEQ ID NOs: 1-2), denoted herein as Alpha-2A-gamma (FIG. 1A); the extracellular and transmembrane domains of FcγRI fused to the intracellular domain of FcRγ, T2A skipping peptide and FcRγ (SEQ ID NOs: 3-4), denoted herein as Alpha-gamma-2A-gamma (FIG. 1B). These plasmids were packed into retrovirus, and used to infect CD4$^+$ and CD8$^+$ T cells. To ensure membrane localization of these constructs, cells were stained for TCRβ and CD3, and for FcRI alpha (FcγRI, CD64). Confocal analysis indicated that in both constructs FcRI was uniformly localized on T cell membrane (FIGS. 2A-B). As the therapeutic strategy of some embodiments is based on re-infusing autologous T cells expressing the above constructs along with a tumor-binding antibody, the killing activity of the transduced T cells was evaluated in-vitro on B16 cells which express histone H2B-tdTomato with or without aTRP-1 antibody, which binds the melanoma antigen gp75 on B16 cells. (FIGS. 4A-B and 5A-C).

Initially, B16-H2B-tdTomato were cultured in serial concentrations ranging from 24 cells to 50,000 per well, imaged in incuCyte and counted by incuCyte analysis tool which detect and count the red fluorescent nuclei in a field captured by the camera. The graph in FIG. 3 shows a direct correlation between the amount of cell cultured and numbers of cell counted in a field. Consequently, the incuCyte imaging system was used to evaluate killing of B16-H2B-tdTomato by anti-TRP-1 antibody and T cells expressing Alpha-2A-gamma or Alpha-gamma-2A-gamma cultured in different effector:target ratios, ranging from 0.5:1 to 16:1. Representative images (FIG. 4A) and target cells numbers (FIG. 4B) after 48 hours show that both CD8$^+$ and CD4$^+$ T cells infected with Alpha-2A-gamma killed the tumor cells when the effector:target ratio is 8 to 1, or higher. The Alpha-gamma-2A-Gamma construct was much more potent compared to Alph-2A-Gamma, and induced target cells killing in effector:target ratio of 2:1 (FIGS. 5A-C).

Taken together, these results demonstrate that concomitant signaling through FcγRI and the FcRγ signaling chain can exert killing capacities in conventional CD4$^+$ and CD8+ T cells whenever the target cells are coated with antibodies. In addition, a comparison shows the advantage of the Alpha-gamma-2A-Gamma construct over the Alpha-2A-gamma construct.

Since the B16-H2B-tdTomato target cells can be distinguished by their red nucleus and the infected cells express GFP originated from the pMIGII vector backbone, their activity could be monitored in real time. Indeed, the majority of tumor cell killing was mediated by the infected T cells as manifested by their GFP expression (FIG. 6A). In order to assess the exogenous expression of FcRI in the CD4+ and CD8+ T cells of mouse origin and in human Jurkat T cells infected with the Alpha-gamma-2A-Gamma, the cells were analyzed for GFP and FcRI (CD64) expression by flow cytometry (FIG. 6B). The analysis indicated that both mouse CD4+ and CD8+ cells and human Jurkat T cell line, have positive correlation between GFP levels and CD64 expression.

Following, the killing activity of Alpha-gamma-2A-Gamma infected CD4+ and CD8+ T cells, with or without anti-TRP-1 antibody was further evaluated in-vitro by counting the B16 tumor cell numbers following 60 hours of co-culturing (FIG. 7). The numbers of B16-H2B-tdTomato target cells counted by the incuCyte imager are shown in comparison to a control of B16 H2B-tdTomato target cells cultured alone. Most importantly, both CD4+ and CD8+ T cells exerted increased killing capacities compared to non-infected T cells.

In addition, the present inventors tested whether FcRI alpha fused to gamma chain can promote tumor cell killing, comparable to that observed when separating the gamma chain from the FcRI alpha chain (e.g. Alpha-2A-gamma and Alpha-gamma-2A-gamma). Therefore, FcRI alpha chain extracellular D1-D2 domains were cloned fused to CD8 hinge and transmembrane domains of CD8a together with signaling intracellular gamma (denoted herein as Alpha-CD8-gamma, SEQ ID NOs: 5-6) as illustrated in FIG. 8A. Furthermore, the present inventors tested if the gamma chain must form a dimer in Alpha-gamma-2A-Gamma by using a sequence with mutated cysteine residues in the transmembrane domain of the Gamma chain, denoted herein as Alpha-gamma-2A-Gamma(mut) (SEQ ID NOs: 7-8, FIG. 8A). Following, CD8+ T cell were infected with the Alpha-2A-Gamma construct (SEQ ID NO: 2), the Alpha-CD8-gamma construct (SEQ ID NO: 6), Alpha-gamma-2A-Gamma construct (SEQ ID NO: 4) or the Alpha-gamma-2A-Gamma(mut) construct (SEQ ID NO: 8) and were co-cultured with B16-H2B-tdTomato with or without an anti-TRP-1 antibody. Representative images are shown of B16-H2B-tdTomato target cells treated with an anti-TRP-1 antibody either alone or following co-culturing of T-cells that are unmodified CD8+ T-cells, CD8+ T cells transduced with Alpha-2A-Gamma, Alpha-CD8-Gamma, Alpha-gamma-2A-Gamma, or Alpha-gamma-2A-Gamma (mut) (FIG. 8B). Target cell numbers were estimated (FIG. 8C). While Alpha-2A-Gamma and Alpha-gamma-2A-Gamma infected T cells in combination with an anti-TRP-1 antibody induced tumor cell killing, Alpha-CD8-gamma and Alpha-gamma-2A-Gamma(mut) infected T cells were almost inert (FIGS. 8B-C). In addition, tumor cell killing was the most pronounced upon combined treatment with anti-TRP-1 and Alpha-gamma-2A-Gamma infected T cells. FIG. 8C indicates a value of around 750 B16 cells when a sham was used. In contrast, Alpha-2A-gamma resulted in a greater reduction, with around 575 B16 cells (FIG. 8C). Alpha-gamma-2A-Gamma had the greatest tumor cell killing, with around 460 B16 cells (FIG. 8C).

Subsequently, the ability of Alpha-gamma-2A-Gamma infected cells to kill another melanoma cell lines was evaluated. To this end, Yumm1.7 melanoma cells expressing H2B-tdTomato were incubated for 48 hours with CD8+ T cells expressing Alpha-gamma-2A-Gamma with or without an anti-TRP-1 antibody. Consistent with the results with the B16 cells, significant killing of Yumm1.7 tumor cells was observed upon addition of anti-TRP-1 (FIG. 9).

Following, the ability of Alpha-gamma-2A-Gamma infected cells to kill tumor cell types other than melanoma was evaluated. To this end, A20 B-cell lymphoma originated from BALB/C mice was incubated overnight with syngeneic CD8+ T cells infected with the Alpha-gamma-2A-Gamma construct and with an anti-CD20 antibody. FIG. 10A shows representative confocal microscopy of the co-culture where T cells are stained for TCRβ and A20 lymphoma cells are stained with B220. Analysis of A20 cell death by Annexin-V staining by flow cytometry showed about 20% killing upon culturing with Alpha-gamma-2A-Gamma infected T cells and anti-CD20 antibody (FIG. 10B).

In addition, the ability of tumor-binding antibody other than anti-TRP-1 to mediate tumor cell killing by the Alpha-gamma-2A-Gamma infected T cells was evaluated. To this end, CD8+ T cells expressing the Alpha-gamma-2A-gamma construct were cultured with B16 cells along with an anti-CD44 antibody which binds the tumor cells. Indeed, anti-CD44 induced tumor cell killing, comparable to that induced by an anti-TRP1 antibody (FIG. 11).

In the same manner, human T cells obtained from healthy donor PBMCs that were infected with Alpha-2A-Gamma or Alpha-gamma-2A-Gamma in pMIGII vector (FIGS. 14A-B) were co-cultured with HT-29 H2B-tdTomato target cells (4:1 effector:target ratio) that express HER2 or EGFR on their membrane (FIG. 14C) with an anti-HER2 antibody Trastuzumab (FIGS. 14E-F). Both Alpha-2A-Gamma and Alpha-gamma-2A-Gamma showed killing activity when Trastuzumab was added to the HER2-expressing cells (FIG. 14E) compared to the EGFR-expressing cells (FIG. 14F), in which no killing activity was observed. However, Alpha-gamma-2A-Gamma showed stronger activity than Alpha-2A-Gamma, as can be seen by the numbers of the live target cells along 48 hours co-culture. Next, human T cells were infected with retrovirus carrying Alpha-gamma-2A-Gamma in pMSVG.1 vector (FIG. 15A). The Alpha-gamma-2A-Gamma infected cells were compared for their killing activity to sham-infected cells, when added to HT-29 H2B tdTomato cells expressing HER2 with or without Trastuzumab (FIG. 15B) or HT-29 H2B tdTomato cells expressing EGFR with or without Cetuximab (FIG. 15C). In both cases Alpha-gamma-2A-Gamma and not sham-infected cells were able to elicit killing activity only when the tumor-binding antibody was added. In addition to the killing activity, the activity of the Alpha-gamma-2A-Gamma expressing T cells was evaluated by cytokines release. To this end, the Alpha-gamma-2A-Gamma or sham-infected cells were co-cultured with HT-29 H2B tdTomato expressing HER2 together with Trastuzumab in different effector:target ratios, and TNFα (FIG. 15D) and IFNγ (FIG. 15E) were measured by ELISA. The results show a correlation between the numbers of Alpha-gamma-2A-Gamma effector to target cells and the levels of cytokines released, while co-culturing sham-infected cells with the target cells did not result in cytokines release. Following, in order to evaluate the specificity of the Alpha-gamma-2A-Gamma activity to the antibody targeting the target cells, Alpha-gamma-2A-Gamma expressing human T cells were co-cultured with HT-29 H2B tdTomato HER2 expressing cells together with relevant or irrelevant antibodies (FIG. 15F). Following 48 hours of co-culture, only the HER-2 binding antibody, Trastuzumab, but not Cetuximab or Retuximab elicited killing of target cells. Taken together, these results further validate that concomitant signaling through FcγRI and the FcRγ signaling chain can exert killing capacities in T cells whenever the target cells are coated with antibodies; and that the Alpha-gamma-2A-Gamma construct is more potent and efficacious compared to the Alpha-2A-gamma construct.

Example 2

T Cells Exogenously Expressing FcRγ and FcγRI Fused to the Intracellular Domain of FcRγ Have In-Vivo Anti-Tumor Effects To test the anti-tumor activity of T cells infected with Alpha-gamma-2A-Gamma in vivo, $2 \times 10^5$ B16 cells were injected sub-cutaneously to C57BL/6 mice. Once tumors reached palpable size, mice were injected with 300 μg anti-TRP-1 antibody sub-cutaneously and $2 \times 10^6$ CD3+ cells infected with Alpha-gamma-2A-Gamma intravenously. As controls, tumor bearing mice were either left untreated, treated with the antibody plus non-infected CD3+ T cells, or with Alpha-gamma-2A-Gamma infected CD3+ T cells without anti-TRP-1 antibody. The results showed no increase in tumor volume only in mice treated with both Alpha-gamma-2A-Gamma infected CD3+ T cells and anti-TRP-1 antibody (FIG. 12).

To demonstrate the anti-tumor activity of the T cells infected with Alpha-gamma-2A-Gamma in human subjects, PBMC are isolated from the apheresis product by density gradient with Ficoll-Hypaque (Lymphocyte Separation Medium, Axis-Shield Diagnostics, Scotland). Following, cells are cultured in a medium containing human serum, IL-2 and anti-CD3 monoclonal antibody OKT-3. Following few days of proliferation, the cells are transduced with the Alpha-gamma-2A-Gamma retroviral vector, followed by 1-2 weeks culturing of the transduced cells in complete medium supplemented with IL-2. These cell are then infused to a subject in need thereof in combination with an antibody targeting the pathologic cells.

Example 3

Exogenous Expression of FcRγ and Anti-EGFR scFv Fused to the Intracellular Domain of FcRγ in CD4+ and CD8+ T Cells Induces Effective Tumor Cell Lysis The following construct is cloned: an anti-EGFR scFv fused to the extracellular D3 domain and transmembrane domain of FcγRI fused to the intracellular domain of FcRγ, T2A skipping peptide and FcRγ (SEQ ID NOs: 37-38), denoted herein as scFv-alpha-gamma-2A-gamma (FIG. 13). The plasmids are packed into retroviruses, and used to infect CD4+ and CD8+ T cells. Following, the killing activity of the transduced T cells is evaluated in-vitro on EGFR expressing tumor cells, for examples H29 colon cancer cells which express histone H2B-tdTomato. Co-culture and killing is evaluated following imaging by incuCyte imager.

Example 4

Exogenous Expression of FcRγ and FcγRI Fused to the Intracellular Domain of FcRγ in γδT Cells and NK Cells Effector cells other than αβ T cells, such as γδ T cells or NK cells can also be genetically-engineered to express Alpha-gamma-2A-Gamma. In order to demonstrate expression in γδ T cells, PBMC's from a healthy donor were incubated with IL-2 and Zoledronic acid in order to expand the γδ T cells population. Following 8 days in culture, cells were separated using EasySep™ Human Gamma/Delta T Cell Isolation Kit, and transduced with Alpha-gamma-2A-Gamma pMIGII construct. The infected cells were imaged by confocal microscopy (FIG. 17). γδ T cells were identified by the specific anti-γδ TCR antibody, and only the transduced cells showed GFP expression originated from the pMIGII vector. The GFP expression was correlated with CD64 staining on the cell membrane. In order to demonstrate expression in NK cells, NK-92 cells were infected with retrovirus carrying Alpha-gamma-2A-Gamma in pMSVG.2 vector. Only infected cells showed high levels of CD64 in flow cytometry analysis (FIG. 18A). Following, the cells were stained for the NK marker CD56 and for CD64 originated from the Alpha-gamma-2A-Gamma and were imaged by confocal microscopy (FIG. 18B).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A recombinant multi subunit protein module comprising at least three recombinant cell membrane polypeptides each comprising an amino acid sequence of an Fc receptor common γ chain (FcRγ), wherein said amino acid sequence is capable of transmitting an activating signal; wherein at least one but not all of said at least three recombinant polypeptides comprises an extracellular binding domain capable of binding a target that is presented on a cell surface of a target cell of an immune cell, such that upon binding of said extracellular binding domain to said target said activating signal is transmitted in an immune cell expressing said multi subunit protein module.

2. The recombinant multi subunit protein module of claim 1, wherein said extracellular binding domain is of an Fcγ receptor and said target is an Fc ligand.

3. The recombinant multi subunit protein module of claim 1, being devoid of an scFv.

4. The recombinant multi subunit protein module of claim 1, wherein said at least one polypeptide comprising said extracellular binding domain comprises an amino acid sequence capable of recruiting polypeptides of said at least three recombinant polypeptides comprising said amino acid sequence of FcRγ comprised in said multi subunit protein module upon binding of said extracellular binding domain to said target.

5. The recombinant multi subunit protein module of claim 4, wherein said amino acid sequence capable of recruiting said other polypeptides comprises the transmembrane domain of an Fc receptor.

6. The recombinant multi subunit protein module of claim 5, wherein said Fc receptor is Fcγ receptor.

7. The recombinant multi subunit protein module of claim 6, wherein said Fcγ receptor is CD64.

8. The recombinant multi subunit protein module of claim 1, wherein said polypeptides comprising said amino acid sequence of FcRγ and not comprising said extracellular binding domain comprise a dimerizing moiety.

9. The recombinant multi subunit protein module of claim 8, wherein said dimerizing moiety comprises an amino acid sequence of a transmembrane domain of said FcRγ.

10. The recombinant multi subunit protein module of claim 1, wherein said extracellular binding domain is of CD64 and said target is an Fc ligand; wherein said at least one polypeptide comprising said extracellular binding domain comprises a transmembrane domain of CD64; and wherein said polypeptides comprising said amino acid sequence of FcRγ and not comprising said extracellular binding domain comprise as a dimerizing moiety an amino acid sequence of a transmembrane domain of said FcRγ.

11. A polynucleotide comprising a heterologous promoter; a nucleic acid sequence encoding a first polypeptide comprising an extracellular and a transmembrane domain of an Fcγ receptor and an intracellular domain of FcRγ; and a nucleic acid sequence encoding a second polypeptide comprising an extracellular, a transmembrane and an intracellular domain of FcRγ.

12. An immune cell comprising an exogenous multi subunit protein module comprising at least three cell membrane polypeptides each comprising an amino acid sequence of an Fc receptor common γ chain (FcRγ), wherein said amino acid sequence is capable of transmitting an activating signal; wherein at least one but not all of said at least three polypeptides comprises an extracellular binding domain capable of binding a target that is presented on a cell surface of a target cell of an immune cell, such that upon binding of said extracellular binding domain to said target said activating signal is transmitted in an immune cell expressing said multi subunit protein module.

13. A method of expressing a multi subunit protein module in an immune cell, the method comprising introducing into an immune cell an exogenous polynucleotide encoding at least three cell membrane polypeptides each comprising an amino acid sequence of an Fc receptor common γ chain (FcRγ), wherein said amino acid sequence is capable of transmitting an activating signal; wherein at least one but not all of said at least three polypeptides comprises an extracellular binding domain capable of binding a target that is presented on a cell surface of a target cell of an immune cell, such that upon binding of said extracellular binding domain to said target said activating signal is transmitted in an immune cell expressing said multi subunit protein module, under conditions which allow expression of said multi subunit protein module.

14. The immune cell of claim 12, wherein said immune cell is a T cell or a NK cell.

15. An article of manufacture comprising a packaging material packaging the immune cell of claim 12 and a therapeutic composition comprising said target.

16. A method of increasing the killing capacity of an antibody against a pathologic cell in a subject in need thereof, the method comprising administering to the subject a therapeutically effective amount of:
   (i) an antibody specific for the pathologic cell; and
   (ii) the immune cell of claim 12, wherein said immune cell is a T cell; wherein said extracellular binding domain is of CD64 and said target is an Fc ligand; thereby increasing the killing capacity of the antibody against the pathologic cell.

17. The recombinant multi subunit protein module of claim 1, wherein said amino acid sequence capable of transmitting an activating signal comprises an intracellular domain of FcRγ.

18. The recombinant multi subunit protein module of claim 1, further comprising a self-cleavable peptide.

19. The recombinant multi subunit protein module of claim 18, wherein said self-cleavable peptide comprises P2A, T2A, or E2A peptide.

20. The immune cell of claim 12, wherein said immune cell is a T-cell.

21. The immune cell of claim 20, wherein said T cell is an αβ T-cell.

22. The polynucleotide of claim 11, wherein said first polypeptide comprises a fusion protein.

23. The polynucleotide of claim 11, further comprising a nucleic acid sequence encoding a self-cleavable peptide.

24. The polynucleotide of claim 23, wherein said nucleic acid sequence encoding said self-cleavable peptide is between said nucleic acid sequence encoding said first polypeptide and said nucleic acid sequence encoding said second polypeptide.

25. The polynucleotide of claim 23, wherein said self-cleavable peptide comprises a 2A skipping peptide.

26. The polynucleotide of claim 23, wherein said self-cleavable peptide comprises P2A, T2A, or E2A peptide.

\* \* \* \* \*

SEQUENCE LISTING

```
Sequence total quantity: 77
SEQ ID NO: 1           moltype = AA  length = 508
FEATURE                Location/Qualifiers
REGION                 1..508
                       note = Alpha-2A-gamma construct aa sequence (mouse origin)
source                 1..508
                       mol_type = protein
                       organism = synthetic construct
SEQUENCE: 1
MILTSFGDDM WLLTTLLLWV PVGGEVVNAT KAVITLQPPW VSIFQKENVT LWCEGPHLPG  60
DSSTQWFING TAVQISTPSY SIPEASFQDS GEYRCQIGSS MPSDPVQLQI HNDWLLLQAS  120
RRVLTEGEPL ALRCHGWKNK LVYNVVFYRN GKSFQFSSDS EVAILKTNLS HSGIYHCSGT  180
GRHRYTSAGV SITVKELFTT PVLRASVSSP FPEGSLVTLN CETNLLLQRP GLQLHFSFYV  240
GSKILEYRNT SSEYHIARAE REDAGFYWCE VATEDSSVLK RSPELELQVL GPQSSAPVWF  300
HILFYLSVGI MFSLNTVLYV KIHRLQREKK YNLEVPLVSE QGKKANSFQQ VRSDGVYEEV  360
TATASQTTPK EAPDGPRSSV GDCGPEQPEP LPPSDSTGAQ TSQSEGRGSL LTCGDVEENP  420
GPMISAVILF LLLLVEQAAA LGEPQLCYIL DAVLFLYGIV LTLLYCRLKI QVRKAAIASR  480
EKADAVYTGL NTRSQETYET LKHEKPPQ                                    508
```

```
SEQ ID NO: 2              moltype = DNA   length = 1527
FEATURE                   Location/Qualifiers
misc_feature              1..1527
                          note = Alpha-2A-gamma construct NA sequence (mouse origin)
source                    1..1527
                          mol_type = other DNA
                          organism = synthetic construct
SEQUENCE: 2
atgattctta ccagctttgg agatgacatg tggcttctaa caactctgct actttgggtt   60
ccagtcggtg gggaagtggt taatgccacc aaggctgtga tcaccttgca gcctccatgg  120
gtcagtattt ccagaagga aaatgtcact ttatggtgtg aggggcctca cctgcctgga   180
gacagttcca cacaatggtt tatcaacgga acagccgttc agatctccac gcctagttat  240
agcatcccag aggccagttt tcaggacagt ggcgaataca ggtgtcagat aggttcctca  300
atgccaagtg accctgtgca gttgcaaatc cacaatgatt ggctgctact ccaggcctcc  360
cgcagagtcc tcacagaagg agaacccctg gccttgaggt gtcacggatg gaagaataaa  420
ctggtgtaca atgtggtttt ctatagaaat ggaaaatcct ttcagttttc ttcagattcg  480
gaggtcgcca ttctgaaaac caacctgagt cacagcggca tctaccactg tcaggcacg  540
ggaagacacc gctacacatc tgcaggagtg tccatcacgg tgaaagagct gtttaccacg  600
ccagtgctga gcatccgt gtcatctccc ttcccggagg ggagtctggt caccctgaac  660
tgtgagacga atttgctcct gcagagaccc ggcttacagc ttcacttctc cttctacgtg  720
ggcagcaaga tcctggagta caggaacaca tcctcagagt accatatagc aagggcggaa  780
agagaagatg ctggattcta ctggtgtgag gtagccacgg aggacagcag tgtccttaag  840
cgcagccctg agtggagct ccaagtgctt ggtcccagt catcagctcc tgtctggttt  900
cacatcctgt tttatctgtc agtgggaata atgtttcgt tgaacacggt tctctatgtg  960
aaaatacaca ggctgcagag agagaagaaa tacaacttag aagtcccttt ggtttctgaa 1020
cagggaaaga aagcaaattc ctttcagcaa gttagaagcg atggcgtgta tgaagaagta 1080
acagccactg cgagccagac acaccaaaa gaagcgcccg atggacctcg aagctcagtg 1140
ggtgactgtg gacccgagca gcctgaaccc cttcctccca gtgacagtac tggggcacaa 1200
acttcccaaa gtgagggcag aggaagtctg ctaacatgcg gagatgaatc ct         1260
ggcccaatga tctcagccgt gatcttgttc ttgctcctt tggtggaaca agcagccgcc 1320
ctgggagagc cgcagctctg ctatatcctg gatgctgtcc tgtttttgta tggtattgtc 1380
cttaccctac tctactgtcg actcaagatc caggtccgaa aggcagctat agccagccgt 1440
gagaaagcag atgctgtcta cacgggcctg aacacccgga gccaggagac atatgagact 1500
ctgaagcatg agaaaccacc ccagtag                                     1527

SEQ ID NO: 3              moltype = AA   length = 466
FEATURE                   Location/Qualifiers
REGION                    1..466
                          note = Alpha-gamma 2A-gamma construct aa sequence (mouse
                          origin)
source                    1..466
                          mol_type = protein
                          organism = synthetic construct
SEQUENCE: 3
MILTSFGDDM WLLTTLLLWV PVGGEVVNAT KAVITLQPPW VSIFQKENVT LWCEGPHLPG   60
DSSTQWFING TAVQISTPSY SIPEASFQDS GEYRCQIGSS MPSDPVQLQI HNDWLLLQAS  120
RRVLTEGEPL ALRCHGWKNK LVYNVVFYRN GKSFQFSSDS EVAILKTNLS HSGIYHCSGT  180
GRHRYTSAGV SITVKELFTT PVLRASVSSP FPEGSLVTLN CETNLLLQRP GLQLHFSFYV  240
GSKILEYRNT SSEYHIARAE REDAGFYWCE VATEDSSVLK RSPELELQVL GPQSSAPVWF  300
HILFYLSVGI MFSLNTVLYV RLKIQVRKAA IASREKADAV YTGLNTRSQE TYETLKHEKP  360
PQEGRGSLLT CGDVEENPGP MISAVILFLL LLVEQAAALG EPQLCYILDA VLFLYGIVLT  420
LLYCRLKIQV RKAAIASREK ADAVYTGLNT RSQETYETLK HEKPPQ                 466

SEQ ID NO: 4              moltype = DNA   length = 1398
FEATURE                   Location/Qualifiers
misc_feature              1..1398
                          note = Alpha-gamma 2A-gamma construct na sequence (mouse
                          origin)
source                    1..1398
                          mol_type = other DNA
                          organism = synthetic construct
SEQUENCE: 4
atgattctta ccagctttgg agatgacatg tggcttctaa caactctgct actttgggtt   60
ccagtcggtg gggaagtggt taatgccacc aaggctgtga tcaccttgca gcctccatgg  120
gtcagtattt ccagaagga aaatgtcact ttatggtgtg aggggcctca cctgcctgga   180
gacagttcca cacaatggtt tatcaacgga acagccgttc agatctccac gcctagttat  240
agcatcccag aggccagttt tcaggacagt ggcgaataca ggtgtcagat aggttcctca  300
atgccaagtg accctgtgca gttgcaaatc cacaatgatt ggctgctact ccaggcctcc  360
cgcagagtcc tcacagaagg agaacccctg gccttgaggt gtcacggatg gaagaataaa  420
ctggtgtaca atgtggtttt ctatagaaat ggaaaatcct ttcagttttc ttcagattcg  480
gaggtcgcca ttctgaaaac caacctgagt cacagcggca tctaccactg tcaggcacg  540
ggaagacacc gctacacatc tgcaggagtg tccatcacgg tgaaagagct gtttaccacg  600
ccagtgctga gcatccgt gtcatctccc ttcccggagg ggagtctggt caccctgaac  660
tgtgagacga atttgctcct gcagagaccc ggcttacagc ttcacttctc cttctacgtg  720
ggcagcaaga tcctggagta caggaacaca tcctcagagt accatatagc aagggcggaa  780
agagaagatg ctggattcta ctggtgtgag gtagccacgg aggacagcag tgtccttaag  840
cgcagccctg agtggagct ccaagtgctt ggtcccagt catcagctcc tgtctggttt  900
cacatcctgt tttatctgtc agtgggaata atgtttcgt tgaacacggt tctctatgtg  960
```

```
cgactcaaga tccaggtccg aaaggcagct atagccagcc gtgagaaagc agatgctgtc  1020
tacacgggcc tgaacacccg gagccaggag acatatgaga ctctgaagca tgagaaacca  1080
ccccaggagg gcagaggaag tctgctaaca tgcggtgacg tcgaggagaa tcctgggcca  1140
atgatctcag ccgtgatctt gttcttgctc cttttggtgg aacaagcagc cgccctggga  1200
gagccgcagc tctgctatat cctggatgct gtccctgttt tgtatggtat tgtccttacc  1260
ctactctact gtcgactcaa gatccaggtc cgaaaggcag ctatagccag ccgtgagaaa  1320
gcagatgctg tctacacggg cctgaacacc cggagccagg agacatatga gactctgaag  1380
catgagaaac cacccccag                                                1398

SEQ ID NO: 5            moltype = AA   length = 405
FEATURE                 Location/Qualifiers
REGION                  1..405
                        note = Alpha-CD8-gamma construct aa sequence (mouse origin)
source                  1..405
                        mol_type = protein
                        organism = synthetic construct
SEQUENCE: 5
MILTSFGDDM WLLTTLLLWV PVGGEVVNAT KAVITLQPPW VSIFQKENVT LWCEGPHLPG   60
DSSTQWFING TAVQISTPSY SIPEASFQDS GEYRCQIGSS MPSDPVQLQI HNDWLLLQAS  120
RRVLTEGEPL ALRCHGWKNK LVYNVVFYRN GKSFQFSSDS EVAILKTNLS HSGIYHCSGT  180
GRHRYTSAGV SITVKELFTT PVLRASVSSP FPEGSLVTLN CETNLLLQRP GLQLHFSFYV  240
GSKILEYRNT SSEYHIARAE REDAGFYWCE VATEDSSVLK RSPELELQVL GPQSSAPTTT  300
KPVLRTPSPV HPTGTSQPQR PEDCRPRGSV KGTGLDFACD IYIWAPLAGI CVALLLSLII  360
TLIRLKIQVR KAAIASREKA DAVYTGLNTR SQETYETLKH EKPPQ                   405

SEQ ID NO: 6            moltype = DNA   length = 1218
FEATURE                 Location/Qualifiers
misc_feature            1..1218
                        note = Alpha-CD8-gamma construct aa sequence (mouse origin)
source                  1..1218
                        mol_type = other DNA
                        organism = synthetic construct
SEQUENCE: 6
atgattctta ccagctttgg agatgacatg tggcttctaa caactctgct actttggggtt   60
ccagtcggtg gggaagtggt taatgccacc aaggctgtga tcaccttgca gcctccatgg  120
gtcagtattt tccagaagga aaatgtcact ttatggtgtg aggggcctca cctgcctgga  180
gacagttcca cacaatggtt tatcaacgga acagccgttc agatctccac gcctagttat  240
agcatcccag aggccagttt tcaggacagt ggcgaataca ggtgtcagat aggttcctca  300
atgccaagtg accctgtgca gttgcaaatc acaatgattg gctgctact ccaggcctcc  360
cgcagagtcc tcacagaagg agaacccctg gccttgaggg gtcacggatg aagaataaa  420
ctggtgtaca atgtggtttt ctatagaaat ggaaaatcct ttcagttttc ttcagattcg  480
gaggtcgcca tttctgaaaac caacctgagt cacagcggca tctaccactg ctcaggcacg  540
ggaagacacc gctacacatc tgcaggagtg tccatcaagt gaaagagct gtttaccacg  600
ccagtgctga gagcatccgt gtcatctccc ttcccggagg ggagtctggt caccctgaac  660
tgtgagacga atttgctcct gcagagaccc ggcttacagc ttcactttc cttctacgtg  720
ggcagcaaga tcctggagta caggaacaca tcctcagagt accatatagc aagggcgaa  780
agagaagatg ctggattcta ctggtgtgag gtagccaggg aagacagcag tgtccttaag  840
cgcagccctg agttggagct ccaagtgctt ggtccccagt catcagctcc tactactacc  900
aagccagtgc tgcgaactcc ctcacctgtg caccctaccg gacatctca gccccagaga  960
ccagaagatt gtcggccccg tggctcagtg aaggggaccg gattggactt cgcctgtgat  1020
atttacatct gggcacccctt ggccgaaatc tgcgtgctgt ttctgctgtc cttgatcatc  1080
actctcatcc gactcaagat ccaggtccga aaggcagcta tagccagccg tgagaaagca  1140
gatgctgtct acacgggcct gaacacccgg agccaggaga catatgagac tctgaagcat  1200
gagaaaccac cccagtag                                                 1218

SEQ ID NO: 7            moltype = AA   length = 466
FEATURE                 Location/Qualifiers
REGION                  1..466
                        note = Alpha-gamma-2A-Gamma(mut) construct AA sequence
                          (mouse origin)
source                  1..466
                        mol_type = protein
                        organism = synthetic construct
SEQUENCE: 7
MILTSFGDDM WLLTTLLLWV PVGGEVVNAT KAVITLQPPW VSIFQKENVT LWCEGPHLPG   60
DSSTQWFING TAVQISTPSY SIPEASFQDS GEYRCQIGSS MPSDPVQLQI HNDWLLLQAS  120
RRVLTEGEPL ALRCHGWKNK LVYNVVFYRN GKSFQFSSDS EVAILKTNLS HSGIYHCSGT  180
GRHRYTSAGV SITVKELFTT PVLRASVSSP FPEGSLVTLN CETNLLLQRP GLQLHFSFYV  240
GSKILEYRNT SSEYHIARAE REDAGFYWCE VATEDSSVLK RSPELELQVL GPQSSAPVWF  300
HILFYLSVGI MFSLNTVLYV RLKIQVRKAA IASREKADAV YTGLNTRSQE TYETLKHEKP  360
PQEGRGSLLT CGDVEENPGP MISAVILFLL LLVEQAAALG EPQLGYILDA VLFLYGIVLT  420
LLYGRLKIQV RKAAIASREK ADAVYTGLNT RSQETYETLK HEKPPQ                 466

SEQ ID NO: 8            moltype = DNA   length = 1656
FEATURE                 Location/Qualifiers
misc_feature            1..1656
                        note = Alpha-gamma-2A-Gamma(mut) construct NA sequence
                          (mouse origin)
source                  1..1656
```

```
                        mol_type = other DNA
                        organism = synthetic construct
SEQUENCE: 8
atgattctta ccagctttgg agatgacatg tggcttctaa caactctgct actttgggtt     60
ccagtcggtg gggaagtggt taatgccacc aaggctgtga tcaccttgca gcctccatgg    120
gtcagtattt tccagaagga aaatgtcact ttatggtgtg aggggcctca cctgcctgga    180
gacagttcca cacaatggtt tatcaacgga acagccgttc agatctccac gcctagttat    240
agcatcccag aggccagttt tcaggacagt ggcgaataca ggtgtcagat aggttcctca    300
atgccaagtg accctgtgca gttgcaaatc cacaatgatt ggctgctact ccaggcctcc    360
cgcagagtcc tcacagaagg agaaccctg gccttgaggt gtcacggatg gaagaataaa    420
ctggtgtaca atgtggtttt ctatagaaat ggaaaatcct ttcagttttc ttcagattcg    480
gaggtcgcca ttctgaaaac caacctgagt cacagcggca tctaccactg ctcaggcacg    540
ggaagacacc gctacacatc tgcaggagtg tccatcacgg tgaagagct gtttaccacg    600
ccagtgctga gagcatccgt gtcatctccc ttcccggagg ggagtctggt caccctgaac    660
tgtgagacga atttgctcct gcagagaccc ggcttacagc ttcacttctc cttctacgtg    720
ggcagcaaga tcctggagta caggaacaca tcctcagagt accatatagc aagggcggaa    780
agagaagatg ctggattcta ctggtgtgag gtagccacgg aggacagcag tgtccttaag    840
cgcagccctg agttggagct ccaagtgctt ggtccccagt catcagctcc tgtctggttt    900
cacatcctgt tttatctgtc agtgggaata atgttttcgt tgaacacggt tctctatgtg    960
cgactcaaga tccaggtccg aaaggcagct atagccagcc gtgagaaagc agatgctgtc   1020
tacacgggcc tgaacacccg gagccaggag acatatgaga ctctgaagca tgagaaacca   1080
ccccaggagg gcagagaaag tctgctaaca tgcggtgacg tcgaggagaa tcctggccca   1140
atgatctcag ccgtgatctt gttcttgctc cttttggtgg aacaagcagc cgccctggga   1200
gagccgcagc tcggctatat cctggatgct gtcctgtttt tgtatggtat tgtccttacc   1260
ctactctacg gtcgactcaa gatccaggtc cgaaaggcag ctatagccag ccgtgagaaa   1320
gcagatgctg tctacacggg cctgaacacc cggagccagg agacatatga gactctgaag   1380
catgagaaac accccagat gatctcagcc gtgatcttgt tcttgctcct tttggtggaa   1440
caagcagccg ccctgggaga gccgcagctc tgctatatcc tggatgctgt cctgtttttg   1500
tatggtattg tccttaccct actctactgt cgactcaaga tccaggtccg aaaggcagct   1560
atagccagcc gtgagaaagc agatgctgtc tacacgggcc tgaacacccg gagccaggag   1620
acatatgaga ctctgaagca tgagaaacca ccccag                             1656

SEQ ID NO: 9           moltype = DNA   length = 37
FEATURE                Location/Qualifiers
misc_feature           1..37
                        note = Single strand DNA oligonucleotide
source                 1..37
                        mol_type = other DNA
                        organism = synthetic construct
SEQUENCE: 9
aataacacta gtgccaccat gcctgaaccg gcaaaat                              37

SEQ ID NO: 10          moltype = DNA   length = 33
FEATURE                Location/Qualifiers
misc_feature           1..33
                        note = Single strand DNA oligonucleotide
source                 1..33
                        mol_type = other DNA
                        organism = synthetic construct
SEQUENCE: 10
aacaaccccg ggacttgtcg tcatcgtctt tgt                                  33

SEQ ID NO: 11          moltype = AA   length = 86
FEATURE                Location/Qualifiers
source                 1..86
                        mol_type = protein
                        organism = Homo sapiens
SEQUENCE: 11
MIPAVVLLLL LLVEQAAALG EPQLCYILDA ILFLYGIVLT LLYCRLKIQV RKAAITSYEK     60
SDGVYTGLST RNQETYETLK HEKPPQ                                          86

SEQ ID NO: 12          moltype = AA   length = 42
FEATURE                Location/Qualifiers
source                 1..42
                        mol_type = protein
                        organism = Mus musculus
SEQUENCE: 12
RLKIQVRKAA IASREKADAV YTGLNTRSQE TYETLKHEKP PQ                        42

SEQ ID NO: 13          moltype = DNA   length = 126
FEATURE                Location/Qualifiers
source                 1..126
                        mol_type = genomic DNA
                        organism = Mus musculus
SEQUENCE: 13
cgactcaaga tccaggtccg aaaggcagct atagccagcc gtgagaaagc agatgctgtc     60
tacacgggcc tgaacacccg gagccaggag acatatgaga ctctgaagca tgagaaacca    120
ccccag                                                               126
```

```
SEQ ID NO: 14              moltype = AA   length = 273
FEATURE                    Location/Qualifiers
source                     1..273
                           mol_type = protein
                           organism = Mus musculus
SEQUENCE: 14
EVVNATKAVI TLQPPWVSIF QKENVTLWCE GPHLPGDSST QWFINGTAVQ ISTPSYSIPE    60
ASFQDSGEYR CQIGSSMPSD PVQLQIHNDW LLLQASRRVL TEGEPLALRC HGWKNKLVYN   120
VVFYRNGKSF QFSSDSEVAI LKTNLSHSGI YHCSGTGRHR YTSAGVSITV KELFTTPVLR   180
ASVSSPFPEG SLVTLNCETN LLLQRPGLQL HFSFYVGSKI LEYRNTSSEY HIARAEREDA   240
GFYWCEVATE DSSVLKRSPE LELQVLGPQS SAP                                273

SEQ ID NO: 15              moltype = DNA  length = 819
FEATURE                    Location/Qualifiers
source                     1..819
                           mol_type = genomic DNA
                           organism = Mus musculus
SEQUENCE: 15
gaagtggtta atgccaccaa ggctgtgatc accttgcagc ctccatgggt cagtattttc    60
cagaaggaaa atgtcacttt atggtgtgag gggcctcacc tgcctggaga cagttccaca   120
caatggttta tcaacggaac agccgttcag atctccacgc ctagttatag catcccagag   180
gccagttttc aggacagtgg cgaatacagg tgtcagatag gttcctcaat gccaagtgac   240
cctgtgcagt tgcaaatcca caatgattgg ctgctactcc aggcctcccg cagagtcctc   300
acagaaggag aacccctggc cttgaggtgt cacggatgga agaataaact ggtgtacaat   360
gtggtttttct atagaaatgg aaaatccttt cagttttctt cagattcgga ggtcgccatt   420
ctgaaaacca acctgagtca cagcggcatc taccactgct catggaagta ccactgctcc   480
tacacatctg caggagtgtc catcacggtg aaagagctgt ttaccacgcc agtgctgaga   540
gcatccgtgt catctccctt cccggagggg agtctggtca ccctgaactg tgagacgaat   600
ttgctcctgc agagacccgg cttacagctt cacttctcct tctacgtggg cagcaagatc   660
ctggagtaca ggaacacatc ctcagagtac catatagcaa gggcggaaag agaagatgct   720
ggattctact ggtgtgaggt agccacggag gacagcagtg tccttaagcg cagccctgag   780
ttggagctcc aagtgcttgg tccccagtca tcagctcct                          819

SEQ ID NO: 16              moltype = AA   length = 23
FEATURE                    Location/Qualifiers
source                     1..23
                           mol_type = protein
                           organism = Mus musculus
SEQUENCE: 16
VWFHILFYLS VGIMFSLNTV LYV                                            23

SEQ ID NO: 17              moltype = DNA  length = 69
FEATURE                    Location/Qualifiers
source                     1..69
                           mol_type = genomic DNA
                           organism = Mus musculus
SEQUENCE: 17
gtctggtttc acatcctgtt ttatctgtca gtgggaataa tgttttcgtt gaacacggtt    60
ctctatgtg                                                            69

SEQ ID NO: 18              moltype = AA   length = 296
FEATURE                    Location/Qualifiers
source                     1..296
                           mol_type = protein
                           organism = Mus musculus
SEQUENCE: 18
EVVNATKAVI TLQPPWVSIF QKENVTLWCE GPHLPGDSST QWFINGTAVQ ISTPSYSIPE    60
ASFQDSGEYR CQIGSSMPSD PVQLQIHNDW LLLQASRRVL TEGEPLALRC HGWKNKLVYN   120
VVFYRNGKSF QFSSDSEVAI LKTNLSHSGI YHCSGTGRHR YTSAGVSITV KELFTTPVLR   180
ASVSSPFPEG SLVTLNCETN LLLQRPGLQL HFSFYVGSKI LEYRNTSSEY HIARAEREDA   240
GFYWCEVATE DSSVLKRSPE LELQVLGPQS SAPVWFHILF YLSVGIMFSL NTVLYV       296

SEQ ID NO: 19              moltype = AA   length = 338
FEATURE                    Location/Qualifiers
source                     1..338
                           mol_type = protein
                           organism = Mus musculus
SEQUENCE: 19
EVVNATKAVI TLQPPWVSIF QKENVTLWCE GPHLPGDSST QWFINGTAVQ ISTPSYSIPE    60
ASFQDSGEYR CQIGSSMPSD PVQLQIHNDW LLLQASRRVL TEGEPLALRC HGWKNKLVYN   120
VVFYRNGKSF QFSSDSEVAI LKTNLSHSGI YHCSGTGRHR YTSAGVSITV KELFTTPVLR   180
ASVSSPFPEG SLVTLNCETN LLLQRPGLQL HFSFYVGSKI LEYRNTSSEY HIARAEREDA   240
GFYWCEVATE DSSVLKRSPE LELQVLGPQS SAPVWFHILF YLSVGIMFSL NTVLYVRLKI   300
QVRKAAIASR EKADAVYTGL NTRSQETYET LKHEKPPQ                           338

SEQ ID NO: 20              moltype = DNA  length = 1014
FEATURE                    Location/Qualifiers
source                     1..1014
                           mol_type = genomic DNA
```

```
                   organism = Mus musculus
SEQUENCE: 20
gaagtggtta atgccaccaa ggctgtgatc accttgcagc ctccatgggt cagtattttc    60
cagaaggaaa atgtcacttt atggtgtgag gggcctcacc tgcctggaga cagttccaca   120
caatggttta tcaacggaac agccgttcag atctccacgc ctagttatag catcccagag   180
gccagttttc aggacagtgg cgaatacagg tgtcagatag gttcctcaat gccaagtgac   240
cctgtgcagt tgcaaatcca caatgattgg ctgctactcc aggcctcccg cagagtcctc   300
acagaaggag aaccccctggc cttgaggtgt cacggatgga agaataaact ggtgtacaat   360
gtggttttct atagaaatgg aaaatccttt cagtttttct cagattcgga ggtcgccatt   420
ctgaaaacca acctgagtca cagcggcatc taccactgct caggcacggg aagacaccgc   480
tacacatctg caggagtgtc catcacggtg aaagagctgt ttaccacgcc agtgctgaga   540
gcatccgtgt catctccctt cccggagggg agtctggtca ccctgaactg tgagacgaat   600
ttgctcctgc agagacccgg cttacagctt cacttctcct tctacgtggg cagcaagatc   660
ctggagtaca ggaacacatc ctcagagtac catatagcaa gggcggaaag agaagatgct   720
ggattctact ggtgtgaggt agccacggag gacagcagtg tccttaagcg cagccctgag   780
ttggagctcc aagtgcttgg tccccagtca tcagctcctg tctggttca catcctgttt    840
tatctgtcag tgggaataat gttttcgttg aacacggttc tctatgtgcg actcaagatc   900
caggtccgaa aggcagctat agccagccgt gagaaagca atgctgtcta cacggccctg   960
aacaccccgga gccaggagac atatgagact ctgaagcatg agaaaccacc cag         1014

SEQ ID NO: 21          moltype = AA  length = 21
FEATURE                Location/Qualifiers
source                 1..21
                       mol_type = protein
                       organism = Mus musculus
SEQUENCE: 21
LCYILDAVLF LYGIVLTLLY C                                              21

SEQ ID NO: 22          moltype = DNA  length = 63
FEATURE                Location/Qualifiers
source                 1..63
                       mol_type = genomic DNA
                       organism = Mus musculus
SEQUENCE: 22
ctctgctata tcctggatgc tgtcctgttt ttgtatggta ttgtccttac cctactctac    60
tgt                                                                  63

SEQ ID NO: 23          moltype = AA  length = 63
FEATURE                Location/Qualifiers
source                 1..63
                       mol_type = protein
                       organism = Mus musculus
SEQUENCE: 23
LCYILDAVLF LYGIVLTLLY CRLKIQVRKA AIASREKADA VYTGLNTRSQ ETYETLKHEK    60
PPQ                                                                  63

SEQ ID NO: 24          moltype = DNA  length = 189
FEATURE                Location/Qualifiers
source                 1..189
                       mol_type = genomic DNA
                       organism = Mus musculus
SEQUENCE: 24
ctctgctata tcctggatgc tgtcctgttt ttgtatggta ttgtccttac cctactctac    60
tgtcgactca agatccaggt ccgaaaggca gctatagcca gccgtgagaa agcagatgct   120
gtctacacgg gcctgaacac ccggagccag gagacatatg agactctgaa gcatgagaaa   180
ccaccccag                                                            189

SEQ ID NO: 25          moltype = AA  length = 36
FEATURE                Location/Qualifiers
REGION                 1..36
                       note = OX40 intracellular domain AA sequence
source                 1..36
                       mol_type = protein
                       organism = synthetic construct
SEQUENCE: 25
RKAWRLPNTP KPCWGNSFRT PIQEEHTDAH FTLAKI                              36

SEQ ID NO: 26          moltype = AA  length = 48
FEATURE                Location/Qualifiers
REGION                 1..48
                       note = 41BB intracellular domain AA sequence
source                 1..48
                       mol_type = protein
                       organism = synthetic construct
SEQUENCE: 26
SVLKWIRKKF PHIFKQPFKK TTGAAQEEDA CSCRCPQEEE GGGGGYEL                 48

SEQ ID NO: 27          moltype = AA  length = 85
FEATURE                Location/Qualifiers
```

```
REGION                  1..85
                        note = IL-2R common gamma intracellular AA sequence
source                  1..85
                        mol_type = protein
                        organism = synthetic construct
SEQUENCE: 27
ERMPPIPPIK NLEDLVTEYQ GNFSAWSGVS KGLTESLQPD YSERFCHVSE IPPKGGALGE   60
GPGGSPCSLH SPYWPPPCYS LKPEA                                        85

SEQ ID NO: 28           moltype = AA   length = 186
FEATURE                 Location/Qualifiers
REGION                  1..186
                        note = TNFR2 intracellular signaling domain AA SEQUENCE
source                  1..186
                        mol_type = protein
                        organism = synthetic construct
SEQUENCE: 28
KKKPSCLQRD AKVPHVPDEK SQDAVGLEQQ HLLTTAPSSS SSSLESSASA GDRRAPPGGH   60
PQARVMAEAQ GFQEARASSR ISDSSHGSHG THVNVTCIVN VCSSSDHSSQ CSSQASATVG  120
DPDAKPSASP KDEQVPFSQE ECPSQSPCET TETLQSHEKP LPLGVPDMGM KPSQAGWFDQ  180
IAVKVA                                                            186

SEQ ID NO: 29           moltype = AA   length = 147
FEATURE                 Location/Qualifiers
REGION                  1..147
                        note = IL-12Rb1 intracellular AA SEQUENCE
source                  1..147
                        mol_type = protein
                        organism = synthetic construct
SEQUENCE: 29
NRAAWHLCPP LPTPCGSTAV EFPGSQGKQA WQWCNPEDFP EVLYPRDALV VEMPGDRGDG   60
TESPQAAPEC ALDTRRPLET QRQRQVQALS EARRLGLARE DCPRGDLAHV TLPLLLGGVT  120
QGASVLDDLW RTHKTAEPGP PTLGQEA                                     147

SEQ ID NO: 30           moltype = AA   length = 216
FEATURE                 Location/Qualifiers
REGION                  1..216
                        note = IL-12Rb2 intracellular AA SEQUENCE
source                  1..216
                        mol_type = protein
                        organism = synthetic construct
SEQUENCE: 30
RYFRQKAFTL LSTLKPQWYS RTIPDPANST WVKKYPILEE KIQLPTDNLL MAWPTPEEPE   60
PLIIHEVLYH MIPVVRQPYY FKRGQGFQGY STSKQDAMYI ANPQATGTLT AETRQLVNLY  120
KVLESRDPDS KLANLTSPLT VTPVNYLPSH EGYLPSNIED LSPHEADPTD SFDLEHQHIS  180
LSIFASSSLR PLIFGGERLT LDRLKMGYDS LMSNEA                           216

SEQ ID NO: 31           moltype = AA   length = 249
FEATURE                 Location/Qualifiers
REGION                  1..249
                        note = IL-23R intracellular AA SEQUENCE
source                  1..249
                        mol_type = protein
                        organism = synthetic construct
SEQUENCE: 31
NRSLRIGIKR KVLLMIPKWL YEDIPNMENS NVAKLLQEKS VFENDNASEQ ALYVDPVLTE   60
ISEISPLEHK PTDYKEERLT GLLETRDCPL GMLSTSSSVV YIPDLNTGYK PQVSNVPPGG  120
NLFINRDERD PTSLETTDDH FARLKTYPNF QFSASSMALL NKTLILDELC LVLNQGEFNS  180
LDIKNSRQEE TSIVLQSDSP SETIPAQTLL SDEFVSCLAI GNEDLPSINS YFPQNVLESH  240
FSRISLFQK                                                         249

SEQ ID NO: 32           moltype = AA   length = 202
FEATURE                 Location/Qualifiers
REGION                  1..202
                        note = IFNgR1 intracellular AA SEQUENCE
source                  1..202
                        mol_type = protein
                        organism = synthetic construct
SEQUENCE: 32
WYTKNNSFKR KSIMLPKSLL SVVKSATLET KPESKYSLVT PHQPAVLESE TVICEEPLST   60
VTAPDSPEAA EQEELSKETK ALEAGGSTSA MTPDSPPTPT QRRSFSLLSS NQSGPCSLTA  120
YHSRNGSDSG LVGSGSSISD LESLPNNNSE TKMAEHDPPP VRKAPMASGY DKPHMLVDVL  180
VDVGGKESLM GYRLTGEAQE LS                                          202

SEQ ID NO: 33           moltype = AA   length = 67
FEATURE                 Location/Qualifiers
REGION                  1..67
                        note = IFNgR2 intracellular AA SEQUENCE
source                  1..67
```

```
                        mol_type = protein
                        organism = synthetic construct
SEQUENCE: 33
LKYQSRVKYW FQAPPNIPEQ IEEYLKDPDQ FILEVLDKDG SPKEDSWDSV SIISSPEKER    60
DDVLQTP                                                              67

SEQ ID NO: 34           moltype = AA  length = 271
FEATURE                 Location/Qualifiers
REGION                  1..271
                        note = IL-2Rb intracellular AA SEQUENCE
source                  1..271
                        mol_type = protein
                        organism = synthetic construct
SEQUENCE: 34
KCRYLGPWLK TVLKCHIPDP SEFFSQLSSQ HGGDLQKWLS SPVPLSFFSP SGPAPEISPL    60
EVLDGDSKAV QLLLLQKDSA PLPSPSGHSQ ASCFTNQGYF FFHLPNALEI ESCQVYFTYD   120
PCVEEEVEED GSRLPEGSPH PPLLPLAGEQ DDYCAFPPRD DLLLFSPSLS TPNTAYGGSR   180
APEERSPLSL HEGLPSLASR DLMGLQRPLE RMPEGDGEGL SANSSGEQAS VPEGNLHGQD   240
QDRGQGPILT LNTDAYLSLQ ELQAQDSVHL I                                  271

SEQ ID NO: 35           moltype = AA  length = 217
FEATURE                 Location/Qualifiers
REGION                  1..217
                        note = IL-1R1 intracellular AA sequence
source                  1..217
                        mol_type = protein
                        organism = synthetic construct
SEQUENCE: 35
KVFKVDIVLW YRDSCSGFLP SKASDGKTYD AYILYPKTLG EGSFSDLDTF VFKLLPEVLE    60
GQFGYKLFIY GRDDYVGEDT IEVTNENVKK SRRLIIILVR DMGGFSWLGQ SSEEQIAIYN   120
ALIQEGIKIV LLELEKIQDY EKMPDSIQFI KQKHGVICWS GDFQERPQSA KTRFWKNLRY   180
QMPAQRRSPL SKHRLLTLDP VRDTKEKLPA ATHLPLG                            217

SEQ ID NO: 36           moltype = AA  length = 182
FEATURE                 Location/Qualifiers
REGION                  1..182
                        note = IL-1AcP intracellular AA sequence
source                  1..182
                        mol_type = protein
                        organism = synthetic construct
SEQUENCE: 36
YRAHFGTDET ILDGKEYDIY VSYARNVEEE EFVLLTLRGV LENEFGYKLC IFDRDSLPGG    60
IVTDETLSFI QKSRRLLVVL SPNYVLQGTQ ALLELKAGLE NMASRGNINV ILVQYKAVKD   120
MKVKELKRAK TVLTVIKWKG EKSKYPQGRF WKQLQVAMPV KKSPRWSSND KQGLSYSSLK   180
NV                                                                  182

SEQ ID NO: 37           moltype = AA  length = 526
FEATURE                 Location/Qualifiers
REGION                  1..526
                        note = scFv-alpha-gamma-2A-gamma construct aa sequence
                        (human origin)
source                  1..526
                        mol_type = protein
                        organism = synthetic construct
SEQUENCE: 37
MALPVTALLL PLALLLHAAR PQVQLKQSGP GLVQPSQSLS ITCTVSGFSL TNYGVHWVRQ    60
SPGKGLEWLG VIWSGGNTDY NTPFTSRLSI NKDNSKSQVF FKMNSLQSND TAIYYCARAL   120
TYYDYEFAYW GQGTLVTVSA ASGGGGSGGG GSGGGGSILL TQSPVILSVS PGERVSFSCR   180
ASQSIGTNIH WYQQRTNGSP RLLIKYASES ISGIPSRFSG SGSGTDFTLS INSVESEDIA   240
DYYCQQNNNW PTTFGAGTKL ELASVTSPLL EGNLVTLSCE TKLLLQRPGL QLYFSFYMGS   300
KTLRGRNTSS EYQILTARRE DSGLYWCEAA TEDGNVLKRS PELELQVLGL QLPTPVWFHV   360
LFYLAVGIMF LVNTVLWVTI RLKIQVRKAA ITSYEKSDGV YTGLSTRNQE TYETLKHEKP   420
PQEGRGSLLT CGDVEENPGP MIPAVVLLLL LLVEQAAALG EPQLCYILDA ILFLYGIVLT   480
LLYCRLKIQV RKAAITSYEK SDGVYTGLST RNQETYETLK HEKPPQ                  526

SEQ ID NO: 38           moltype = DNA  length = 1578
FEATURE                 Location/Qualifiers
misc_feature            1..1578
                        note = scFv-alpha-gamma-2A-gamma construct NA sequqence
                        (human origin)
source                  1..1578
                        mol_type = other DNA
                        organism = synthetic construct
SEQUENCE: 38
atggccttac cagtgaccgc cttgctcctg ccgctggcct tgctgctcca cgccgccagg    60
ccgcaagtac aacttaaaca gagcggtcct ggtctggtgc aacccctcca aagcctttca   120
atcacgtgta ccgtttccgg ttttcactt acgaattacg cgtccattg ggtgcggcaa    180
agtccaggca aggtctggag tggcttggc gtaatctggt caggaggtaa tacggactac   240
aacacacctt ttactagcag acttagcatc aacaaggata acagtaagag tcaggtcttc   300
```

```
ttcaagatga  atagtttgca  atccaatgat  acagctatct  actactgcgc  cagagctttg   360
acctactacg  attatgagtt  tgcatattgg  ggtcaaggaa  ctctggtaac  agtaagcgcc   420
gcttcaggtg  gaggtggttc  tggggggtggg ggctcaggtg  ggggaggtag  cattcttctc   480
acccagtcac  ccgttatact  ttccgtatct  ccgggagaaa  gggtctcttt  cagttgtcgc   540
gcgagtcaaa  gcataggcac  taatatccac  tggtaccaaa  aaagaacaaa  cggttcaccc   600
agactgttga  tcaaatatgc  gtcagagagt  attagcggga  tccctagcag  attttccgga   660
agcggaagcg  gtactgattt  tacactgagc  attaatagcg  ttgaaagtga  ggatattgcg   720
gactactact  gccaacaaaa  caataactgg  cctacaactt  tcggtgcagg  tacgaaattg   780
gagctcgcat  ctgtgacatc  cccactcctg  gaggggaatc  tggtcaccct  gactgtgtga   840
acaaagttgc  tcttgcagag  gcctgggttg  cagctttact  tctccttcta  catgggcagc   900
aagaccctgc  gaggcaggaa  cacatcctct  gaataccaaa  tactaactgc  tagaagagaa   960
gactctgggt  tatactggtg  cgaggctgcc  acagaggatg  aaatgtcct   taagcgcagc  1020
cctgagttgg  agcttcaagt  gcttggcctc  cagttaccaa  ctcctgtctg  gtttcatgtc  1080
cttttctatc  tggcagtggg  aataatgttt  ttagtgaaca  ctgttctctg  ggtgacaata  1140
cgactgaaga  tccaagtgcg  aaaggcagct  ataaccagct  atgagaaatc  agatggtgtt  1200
tacacgggcc  tgagcaccag  gaaccaggag  acttacgaga  ctctgaagca  tgagaaacca  1260
ccacaggagg  gcagaggaag  tctgctaaca  tgcggtgacg  tcgaggagaa  tcctggccca  1320
atgattccag  cagtggtctt  gctcttactc  cttttggttg  aacaagcagt  ggccctggga  1380
gagcctcagc  tctgctatat  cctggatgcc  atcctgtttc  tgtatggaat  tgtcctcacc  1440
ctcctctact  gtcgactgaa  gatccaagtc  gaaaggcag   ctataaccag  ctatgagaaa  1500
tcagatggtg  tttacacggg  cctgagcacc  aggaaccagg  agacttacga  gactctgaag  1560
catgagaaac  caccacag                                                    1578

SEQ ID NO: 39           moltype = AA  length = 42
FEATURE                 Location/Qualifiers
source                  1..42
                        mol_type = protein
                        organism = Homo sapiens
SEQUENCE: 39
RLKIQVRKAA ITSYEKSDGV YTGLSTRNQE TYETLKHEKP PQ                            42

SEQ ID NO: 40           moltype = DNA  length = 126
FEATURE                 Location/Qualifiers
source                  1..126
                        mol_type = genomic DNA
                        organism = Homo sapiens
SEQUENCE: 40
cgactgaaga tccaagtgcg aaaggcagct ataaccagct atgagaaatc agatggtgtt         60
tacacgggcc tgagcaccag gaaccaggag acttacgaga ctctgaagca tgagaaacca       120
ccacag                                                                   126

SEQ ID NO: 41           moltype = AA  length = 121
FEATURE                 Location/Qualifiers
REGION                  1..121
                        note = anti-EFGR variable heavy chain aa sequence
source                  1..121
                        mol_type = protein
                        organism = synthetic construct
SEQUENCE: 41
QVQLKQSGPG LVQPSQSLSI TCTVSGFSLT NYGVHWVRQS PGKGLEWLGV IWSGGNTDYN         60
TPFTSRLSIN KDNSKSQVFF KMNSLQSNDT AIYYCARALT YYDYEFAYWG QGTLVTVSAA       120
S                                                                        121

SEQ ID NO: 42           moltype = AA  length = 105
FEATURE                 Location/Qualifiers
REGION                  1..105
                        note = anti-EFGR variable light chain aa sequence
source                  1..105
                        mol_type = protein
                        organism = synthetic construct
SEQUENCE: 42
ILLTQSPVIL SVSPGERVSF SCRASQSIGT NIHWYQQRTN GSPRLLIKYA SESISGIPSR         60
FSGSGSGTDF TLSINSVESE DIADYYCQQN NNWPTTFGAG TKLEL                        105

SEQ ID NO: 43           moltype = AA  length = 241
FEATURE                 Location/Qualifiers
REGION                  1..241
                        note = Anti EGFR scFv aa sequence
source                  1..241
                        mol_type = protein
                        organism = synthetic construct
SEQUENCE: 43
QVQLKQSGPG LVQPSQSLSI TCTVSGFSLT NYGVHWVRQS PGKGLEWLGV IWSGGNTDYN         60
TPFTSRLSIN KDNSKSQVFF KMNSLQSNDT AIYYCARALT YYDYEFAYWG QGTLVTVSAA       120
SGGGGSGGGG SGGGGSILLT QSPVILSVSP GERVSFSCRA SQSIGTNIHW YQQRTNGSPR       180
LLIKYASESI SGIPSRFSGS GSGTDFTLSI NSVESEDIAD YYCQQNNNWP TTFGAGTKLE       240
L                                                                        241

SEQ ID NO: 44           moltype = AA  length = 277
```

```
FEATURE              Location/Qualifiers
source               1..277
                     mol_type = protein
                     organism = Homo sapiens
SEQUENCE: 44
QVDTTKAVIT LQPPWVSVFQ EETVTLHCEV LHLPGSSSTQ WFLNGTATQT STPSYRITSA   60
SVNDSGEYRC QRGLSGRSDP IQLEIHRGWL LLQVSSRVFT EGEPLALRCH AWKDKLVYNV  120
LYYRNGKAFK FFHWNSNLTI LKTNISHNGT YHCSGMGKHR YTSAGISVTV KELFPAPVLN  180
ASVTSPLLEG NLVTLSCETK LLLQRPGLQL YFSFYMGSKT LRGRNTSSEY QILTARREDS  240
GLYWCEAATE DGNVLKRSPE LELQVLGLQL PTPVWFH                           277

SEQ ID NO: 45        moltype = AA  length = 180
FEATURE              Location/Qualifiers
source               1..180
                     mol_type = protein
                     organism = Mus musculus
SEQUENCE: 45
EVVNATKAVI TLQPPWVSIF QKENVTLWCE GPHLPGDSST QWFINGTAVQ ISTPSYSIPE   60
ASFQDSGEYR CQIGSSMPSD PVQLQIHNDW LLLQASRRVL TEGEPLALRC HGWKNKLVYN  120
VVFYRNGKSF QFSSDSEVAI LKTNLSHSGI YHCSGTGRHR YTSAGVSITV KELFTTPVLR  180

SEQ ID NO: 46        moltype = AA  length = 180
FEATURE              Location/Qualifiers
source               1..180
                     mol_type = protein
                     organism = Homo sapiens
SEQUENCE: 46
QVDTTKAVIT LQPPWVSVFQ EETVTLHCEV LHLPGSSSTQ WFLNGTATQT STPSYRITSA   60
SVNDSGEYRC QRGLSGRSDP IQLEIHRGWL LLQVSSRVFT EGEPLALRCH AWKDKLVYNV  120
LYYRNGKAFK FFHWNSNLTI LKTNISHNGT YHCSGMGKHR YTSAGISVTV KELFPAPVLN  180

SEQ ID NO: 47        moltype = AA  length = 21
FEATURE              Location/Qualifiers
source               1..21
                     mol_type = protein
                     organism = Homo sapiens
SEQUENCE: 47
VLFYLAVGIM FLVNTVLWVT I                                             21

SEQ ID NO: 48        moltype = AA  length = 298
FEATURE              Location/Qualifiers
source               1..298
                     mol_type = protein
                     organism = Homo sapiens
SEQUENCE: 48
QVDTTKAVIT LQPPWVSVFQ EETVTLHCEV LHLPGSSSTQ WFLNGTATQT STPSYRITSA   60
SVNDSGEYRC QRGLSGRSDP IQLEIHRGWL LLQVSSRVFT EGEPLALRCH AWKDKLVYNV  120
LYYRNGKAFK FFHWNSNLTI LKTNISHNGT YHCSGMGKHR YTSAGISVTV KELFPAPVLN  180
ASVTSPLLEG NLVTLSCETK LLLQRPGLQL YFSFYMGSKT LRGRNTSSEY QILTARREDS  240
GLYWCEAATE DGNVLKRSPE LELQVLGLQL PTPVWFHVLF YLAVGIMFLV NTVLWVTI    298

SEQ ID NO: 49        moltype = AA  length = 340
FEATURE              Location/Qualifiers
source               1..340
                     mol_type = protein
                     organism = Homo sapiens
SEQUENCE: 49
QVDTTKAVIT LQPPWVSVFQ EETVTLHCEV LHLPGSSSTQ WFLNGTATQT STPSYRITSA   60
SVNDSGEYRC QRGLSGRSDP IQLEIHRGWL LLQVSSRVFT EGEPLALRCH AWKDKLVYNV  120
LYYRNGKAFK FFHWNSNLTI LKTNISHNGT YHCSGMGKHR YTSAGISVTV KELFPAPVLN  180
ASVTSPLLEG NLVTLSCETK LLLQRPGLQL YFSFYMGSKT LRGRNTSSEY QILTARREDS  240
GLYWCEAATE DGNVLKRSPE LELQVLGLQL PTPVWFHVLF YLAVGIMFLV NTVLWVTIRL  300
KIQVRKAAIT SYEKSDGVYT GLSTRNQETY ETLKHEKPPQ                        340

SEQ ID NO: 50        moltype = AA  length = 21
FEATURE              Location/Qualifiers
source               1..21
                     mol_type = protein
                     organism = Homo sapiens
SEQUENCE: 50
LCYILDAILF LYGIVLTLLY C                                             21

SEQ ID NO: 51        moltype = AA  length = 63
FEATURE              Location/Qualifiers
source               1..63
                     mol_type = protein
                     organism = Homo sapiens
SEQUENCE: 51
LCYILDAILF LYGIVLTLLY CRLKIQVRKA AITSYEKSDG VYTGLSTRNQ ETYETLKHEK   60
```

```
PPQ                                                                          63

SEQ ID NO: 52           moltype = AA  length = 401
FEATURE                 Location/Qualifiers
source                  1..401
                        mol_type = protein
                        organism = Homo sapiens
SEQUENCE: 52
QVQLKQSGPG LVQPSQSLSI TCTVSGFSLT NYGVHWVRQS PGKGLEWLGV IWSGGNTDYN   60
TPFTSRLSIN KDNSKSQVFF KMNSLQSNDT AIYYCARALT YDYEFAYWG QGTLVTVSAA   120
SGGGGSGGGG SGGGGSILLT QSPVILSVSP GERVSFSCRA SQSIGTNIHW YQQRTNGSPR   180
LLIKYASESI SGIPSRFSGS GSGTDFTLSI NSVESEDIAD YYCQQNNNWP TTFGAGTKLE   240
LASVTSPLLE GNLVTLSCET KLLLQRPGLQ LYFSFYMGSK TLRGRNTSSE YQILTARRED   300
SGLYWCEAAT EDGNVLKRSP ELELQVLGLQ LPTPVWFHVL FYLAVGIMFL VNTVLWVTIR   360
LKIQVRKAAI TSYEKSDGVY TGLSTRNQET YETLKHEKPP Q                       401

SEQ ID NO: 53           moltype = AA  length = 20
FEATURE                 Location/Qualifiers
REGION                  1..20
                        note = Linker amino acid sequence
REPEAT                  1..5
                        note = repeat sequence 1-4 times
REPEAT                  6..10
                        note = may be absent
REPEAT                  11..15
                        note = may be absent
REPEAT                  16..20
                        note = may be absent
source                  1..20
                        mol_type = protein
                        organism = synthetic construct
SEQUENCE: 53
GGGGSGGGGS GGGGSGGGGS                                                20

SEQ ID NO: 54           moltype = AA  length = 9
FEATURE                 Location/Qualifiers
REGION                  1..9
                        note = Linker amino acid sequence
source                  1..9
                        mol_type = protein
                        organism = synthetic construct
SEQUENCE: 54
GGGGSGGGG                                                            9

SEQ ID NO: 55           moltype = AA  length = 8
FEATURE                 Location/Qualifiers
REGION                  1..8
                        note = Linker amino acid sequence
source                  1..8
                        mol_type = protein
                        organism = synthetic construct
SEQUENCE: 55
GGGGGGGG                                                             8

SEQ ID NO: 56           moltype = AA  length = 6
FEATURE                 Location/Qualifiers
REGION                  1..6
                        note = Linker amino acid sequence
source                  1..6
                        mol_type = protein
                        organism = synthetic construct
SEQUENCE: 56
GGGGGG                                                               6

SEQ ID NO: 57           moltype = AA  length = 15
FEATURE                 Location/Qualifiers
REGION                  1..15
                        note = Linker amino acid sequence
REPEAT                  1..5
                        note = Repeat 1-3 times
REPEAT                  6..10
                        note = may be absent
REPEAT                  11..15
                        note = may be absent
source                  1..15
                        mol_type = protein
                        organism = synthetic construct
SEQUENCE: 57
EAAAKEAAAK EAAAK                                                     15
```

```
SEQ ID NO: 58            moltype = AA   length = 5
FEATURE                  Location/Qualifiers
REGION                   1..5
                         note = Linker amino acid sequence
source                   1..5
                         mol_type = protein
                         organism = synthetic construct
SEQUENCE: 58
PAPAP                                                                      5

SEQ ID NO: 59            moltype = AA   length = 15
FEATURE                  Location/Qualifiers
REGION                   1..15
                         note = Linker amino acid sequence
source                   1..15
                         mol_type = protein
                         organism = synthetic construct
SEQUENCE: 59
GGGGSGGGGS GGGGS                                                          15

SEQ ID NO: 60            moltype = AA   length = 93
FEATURE                  Location/Qualifiers
source                   1..93
                         mol_type = protein
                         organism = Mus musculus
SEQUENCE: 60
ASVSSPPFEG SLVTLNCETN LLLQRPGLQL HFSFYVGSKI LEYRNTSSEY HIARAEREDA          60
GFYWCEVATE DSSVLKRSPE LELQVLGPQS SAP                                       93

SEQ ID NO: 61            moltype = AA   length = 97
FEATURE                  Location/Qualifiers
source                   1..97
                         mol_type = protein
                         organism = Homo sapiens
SEQUENCE: 61
ASVTSPLLEG NLVTLSCETK LLLQRPGLQL YFSFYMGSKT LRGRNTSSEY QILTARREDS          60
GLYWCEAATE DGNVLKRSPE LELQVLGLQL PTPVWFH                                   97

SEQ ID NO: 62            moltype = DNA   length = 1395
FEATURE                  Location/Qualifiers
misc_feature             1..1395
                         note = Alpha-2A-gamma construct NA sequqence (HUMAN origin)
source                   1..1395
                         mol_type = other DNA
                         organism = synthetic construct
SEQUENCE: 62
atggccttac cagtgaccgc cttgctcctg ccgctggcct tgctgctcca cgccgccagg          60
ccgcaagtgg acaccacaaa ggcagtgatc actttgcagc ctccatgggt cagcgtgttc         120
caagaggaaa ccgtaacctt gcattgtgag gtgctccatc tgcctgggag cagctctaca         180
cagtggtttc tcaatggcac agccactcag acctcgaccc ccagctacag aatcacctct         240
gccagtgtca atgacagtgg tgaatacagg tgccagagag gtctctcagg gcgaagtgac         300
cccatacagc tggaaatcca cagaggctgg ctactactgc aggtctccag cagagtcttc         360
acggaaggag aacctctggc cttgaggtgt catgcgtgga aggataagct ggtgtacaat         420
gtgctttact atcgaaatgg caaagccttt aagttttttc actggaactc taacctcacc         480
attctgaaaa ccaacataag tcacaatggc acctaccatt gctcaggcat gggaaagcat         540
cgctacacat cagcaggaat atctgtcact gtgaaagagc tatttccagc tccagtgctg         600
aatgcatctg tgacatcccc actcctggag gggaatctgg tcaccctgag ctgtgaaaca         660
aagttgctct tgcagaggcc tggtttgcag ctttactttt ccttctacat gggcagcaag         720
accctgcgag gcaggaacac atcctctgaa taccaaatac taactgctag aagagaagac         780
tctgggttat actggtgcga ggctgccaca gaggatggaa atgtccttaa gcgcagccct         840
gagttggagc ttcaagtgct tggcctccag ttaccaactc ctgtctggtt tcatgtcctt         900
ttctatctgg cagtgggaat aatgttttta gtgaacactg ttctctgggt gacaatacga         960
ctgaagatcc aagtgcgaaa ggcagctata accagctatg agaaatcaga tggtgtttac        1020
acgggcctga gcaccaggaa ccaggagact tacgagactc tgaagcatga aaaccacca         1080
caggagggca gaggaagtct gctaacatgc ggtgacgtcg aggagaatcc tgcccaatg         1140
attccagcag tggtcttgct cttactcctt ttggttgaac aagcagcggc cctgggagag        1200
cctcagctct gctatatcct ggatgccatc ctgtttctgt atggaattgt cctcacccte        1260
ctctactgtc gactgaagat ccaagtgcga aaggcagcta taaccagcta tgagaaatca        1320
gatggtgttt acacgggcct gagcaccagg aaccaggaga cttacgagac tctgaagcat        1380
gagaaaccac cacag                                                        1395

SEQ ID NO: 63            moltype = AA   length = 465
FEATURE                  Location/Qualifiers
REGION                   1..465
                         note = Alpha-gamma 2A-gamma construct aa sequence (HUMAN
                         origin)
source                   1..465
                         mol_type = protein
```

```
                        organism = synthetic construct
SEQUENCE: 63
MALPVTALLL PLALLLHAAR PQVDTTKAVI TLQPPWVSVF QEETVTLHCE VLHLPGSSST     60
QWFLNGTATQ TSTPSYRITS ASVNDSGEYR CQRGLSGRSD PIQLEIHRGW LLLQVSSRVF    120
TEGEPLALRC HAWKDKLVYN VLYYRNGKAF KFFHWNSNLT ILKTNISHNG TYHCSGMGKH    180
RYTSAGISVT VKELFPAPVL NASVTSPLLE GNLVTLSCET KLLLQRPGLQ LYFSFYMGSK    240
TLRGRNTSSE YQILTARRED SGLYWCEAAT EDGNVLKRSP ELELQVLGLQ LPTPVWFHVL    300
FYLAVGIMFL VNTVLWVTIR LKIQVRKAAI TSYEKSDGVY TGLSTRNQET YETLKHEKPP    360
QEGRGSLLTC GDVEENPGPM IPAVVLLLLL LVEQAAALGE PQLCYILDAI LFLYGIVLTL    420
LYCRLKIQVR KAAITSYEKS DGVYTGLSTR NQETYETLKH EKPPQ                    465

SEQ ID NO: 64           moltype = AA   length = 277
FEATURE                 Location/Qualifiers
REGION                  1..277
                        note = Extracellular domain of CD64 (D1+D2+D3) AA sequence
                           (HUMAN)
source                  1..277
                        mol_type = protein
                        organism = synthetic construct
SEQUENCE: 64
QVDTTKAVIT LQPPWVSVFQ EETVTLHCEV LHLPGSSSTQ WFLNGTATQT STPSYRITSA     60
SVNDSGEYRC QRGLSGRSDP IQLEIHRGWL LLQVSSRVFT EGEPLALRCH AWKDKLVYNV    120
LYYRNGKAFK FFHWNSNLTI LKTNISHNGT YHCSGMGKHR YTSAGISVTV KELFPAPVLN    180
ASVTSPLLEG NLVTLSCETK LLLQRPGLQL YFSFYMGSKT LRGRNTSSEY QILTARREDS    240
GLYWCEAATE DGNVLKRSPE LELQVLGLQL PTPVWFH                             277

SEQ ID NO: 65           moltype = DNA   length = 831
FEATURE                 Location/Qualifiers
misc_feature            1..831
                        note = Extracellular domain of CD64 (D1+D2+D3) NA sequence
                           (HUMAN)
source                  1..831
                        mol_type = other DNA
                        organism = synthetic construct
SEQUENCE: 65
caagtggaca ccacaaaggc agtgatcact ttgcagcctc catgggtcag cgtgttccaa     60
gaggaaaccg taaccttgca ttgtgaggtg ctccatctgc ctgggagcag ctctacacag    120
tggtttctca atggcacagc cactcagacc tcgaccccca gctacagaat cacctctgcc    180
agtgtcaatg acagtggtga ataccggtgc cagagaggtc tctcagggcg aagtgacccc    240
atacagctgg aaatccacag aggctggcta ctactgcagg tctccagcag agtcttcacg    300
gaaggagaac tctggccttt gaggtgtcat gcgtggaagg ataagctggt gtacaatgtg    360
ctttactatc gaaatggcaa agcctttaag ttttcccact ggaactctaa cctcaccatt    420
ctgaaaacca acataagtca caatggcacc taccattgct caggcatggg aaagcatcgc    480
tacacatcag caggaatatc tgtcactgtg aaagagctat tccagctcc agtgctgaat     540
gcatctgtga catccccact cctggagggg aatctggtca ccctgagctg tgaaacaaag    600
ttgctcttga gaggcctggt tttgcagctt tacttctcct tctacatggg cagcaagacc    660
ctgcgaggca ggaacacatc ctctgaatac caaatactaa ctgctagaag agaagactct    720
gggttatact ggtgcgaggc tgccacagag gatggaaatg tccttaagcg cagccctgag    780
ttggagcttc aagtgcttgg cctccagtta ccaactcctg tctggtttca t             831

SEQ ID NO: 66           moltype = DNA   length = 63
FEATURE                 Location/Qualifiers
misc_feature            1..63
                        note = Transmembrane domain of CD64 NA sequence (HUMAN)
source                  1..63
                        mol_type = other DNA
                        organism = synthetic construct
SEQUENCE: 66
gtccttttct atctggcagt gggaataatg ttttagtga acactgttct ctgggtgaca      60
ata                                                                   63

SEQ ID NO: 67           moltype = DNA   length = 63
FEATURE                 Location/Qualifiers
misc_feature            1..63
                        note = FcR gamma chain TM nA SEQUENCE (HUMAN)
source                  1..63
                        mol_type = other DNA
                        organism = synthetic construct
SEQUENCE: 67
ctctgctata tcctggatgc catcctgttt ctgtatggaa ttgtcctcac cctcctctac      60
tgt                                                                   63

SEQ ID NO: 68           moltype = DNA   length = 15
FEATURE                 Location/Qualifiers
misc_feature            1..15
                        note = FcR gamma chain EC NA SEQUENCE (HUMAN)
source                  1..15
                        mol_type = other DNA
                        organism = synthetic construct
```

```
SEQUENCE: 68
ctgggagagc ctcag                                                    15

SEQ ID NO: 69          moltype = AA  length = 5
FEATURE                Location/Qualifiers
REGION                 1..5
                       note = FcR gamma chain EC AA SEQUENCE (HUMAN)
source                 1..5
                       mol_type = protein
                       organism = synthetic construct
SEQUENCE: 69
LGEPQ                                                                5

SEQ ID NO: 70          moltype = DNA  length = 204
FEATURE                Location/Qualifiers
misc_feature           1..204
                       note = FcR gamma chain EC+TM+IC NA SEQUENCE (HUMAN)
source                 1..204
                       mol_type = other DNA
                       organism = synthetic construct
SEQUENCE: 70
ctgggagagc ctcagctctg ctatatcctg gatgccatcc tgtttctgta tggaattgtc   60
ctcaccctcc tctactgtcg actgaagatc caagtgcgaa aggcagctat aaccagctat  120
gagaaatcag atggtgttta cacgggcctg agcaccagga accaggagac ttacgagact  180
ctgaagcatg agaaaccacc acag                                         204

SEQ ID NO: 71          moltype = AA  length = 68
FEATURE                Location/Qualifiers
REGION                 1..68
                       note = FcR gamma chain EC+TM+IC AA SEQUENCE (HUMAN)
source                 1..68
                       mol_type = protein
                       organism = synthetic construct
SEQUENCE: 71
LGEPQLCYIL DAILFLYGIV LTLLYCRLKI QVRKAAITSY EKSDGVYTGL STRNQETYET   60
LKHEKPPQ                                                            68

SEQ ID NO: 72          moltype = DNA  length = 63
FEATURE                Location/Qualifiers
misc_feature           1..63
                       note = CD8A signal peptide NA
source                 1..63
                       mol_type = other DNA
                       organism = synthetic construct
SEQUENCE: 72
atggccttac cagtgaccgc cttgctcctg ccgctggcct tgctgctcca cgccgccagg   60
ccg                                                                 63

SEQ ID NO: 73          moltype = AA  length = 21
FEATURE                Location/Qualifiers
REGION                 1..21
                       note = CD8A signal peptide AA
source                 1..21
                       mol_type = protein
                       organism = synthetic construct
SEQUENCE: 73
MALPVTALLL PLALLLHAAR P                                             21

SEQ ID NO: 74          moltype = DNA  length = 54
FEATURE                Location/Qualifiers
misc_feature           1..54
                       note = SIGNAL SEQUENCE NA
source                 1..54
                       mol_type = other DNA
                       organism = synthetic construct
SEQUENCE: 74
atgattccag cagtggtctt gctcttactc cttttggttg aacaagcagc ggcc         54

SEQ ID NO: 75          moltype = AA  length = 18
FEATURE                Location/Qualifiers
REGION                 1..18
                       note = SIGNAL SEQUENCE AA
source                 1..18
                       mol_type = protein
                       organism = synthetic construct
SEQUENCE: 75
MIPAVVLLLL LLVEQAAA                                                 18

SEQ ID NO: 76          moltype = DNA  length = 54
```

```
FEATURE             Location/Qualifiers
misc_feature        1..54
                    note = T2A peptide NA
source              1..54
                    mol_type = other DNA
                    organism = synthetic construct
SEQUENCE: 76
gagggcagag gaagtctgct aacatgcggt gacgtcgagg agaatcctgg ccca        54

SEQ ID NO: 77       moltype = AA  length = 18
FEATURE             Location/Qualifiers
REGION              1..18
                    note = T2A peptide AA
source              1..18
                    mol_type = protein
                    organism = synthetic construct
SEQUENCE: 77
EGRGSLLTCG DVEENPGP                                                18
```